(12) United States Patent
Kassatly et al.

(10) Patent No.: US 11,399,594 B2
(45) Date of Patent: Aug. 2, 2022

(54) FOOTWEAR AUXILIARIES FOR SYNCHRONOUSLY TONING LEG MUSCLES IN ORDER TO STRAIGHTEN BACK POSTURE

(71) Applicants: Danielle M Kassatly, San Jose, CA (US); Michelle M Kassatly, San Jose, CA (US); L Samuel A Kassatly, San Jose, CA (US); Gabrielle M Kassatly, San Jose, CA (US)

(72) Inventors: Danielle M Kassatly, San Jose, CA (US); Michelle M Kassatly, San Jose, CA (US); L Samuel A Kassatly, San Jose, CA (US); Gabrielle M Kassatly, San Jose, CA (US)

( * ) Notice: Subject to any disclaimer, the term of this patent is extended or adjusted under 35 U.S.C. 154(b) by 1233 days.

(21) Appl. No.: 15/453,993

(22) Filed: Mar. 9, 2017

(65) Prior Publication Data

US 2017/0172249 A1 Jun. 22, 2017

Related U.S. Application Data

(63) Continuation-in-part of application No. 13/889,316, filed on May 7, 2013, now Pat. No. 9,610,417.

(51) Int. Cl.
*A43B 13/20* (2006.01)
*A43B 7/00* (2006.01)
(Continued)

(52) U.S. Cl.
CPC .......... *A43B 13/20* (2013.01); *A43B 7/00* (2013.01); *A61M 16/0051* (2013.01); *A61M 16/0069* (2014.02); *A61M 16/024* (2017.08); *A61M 16/0493* (2014.02); *A61M 16/20* (2013.01); *H02J 7/35* (2013.01); *A61M 16/107* (2014.02); *A61M 2016/0021* (2013.01); *A61M 2016/0027* (2013.01); *A61M 2205/8256* (2013.01); *H01M 10/46* (2013.01); *H02J 7/34* (2013.01)

(58) Field of Classification Search
CPC ............................................. A43B 13/18–206
See application file for complete search history.

(56) References Cited

U.S. PATENT DOCUMENTS 4,247,962 A * 2/1981 Hall ...................... A47C 27/085
5/682
4,296,510 A * 10/1981 Phillips ................ A47C 27/085
5/682

(Continued)

*Primary Examiner* — Nyca T Nguyen
(74) *Attorney, Agent, or Firm* — Samuel A Kassatly

(57) ABSTRACT

A programmable memory device for incorporation within a medium to distribute a force or shock, F, within the medium. It includes a programmable combination of micro-levers that cooperate in order to selectively disperse, absorb, redirect, reorient, or displace, at least part of the force, F, in a customizable fashion. At least one of the micro-levers includes a platform that is supported on a top portion of a support, in order to enable a lever action or momentum of the platform within the medium. As the force, F, is applied on the micro-lever, a reactive force, R, is generated and causes any a movement of the platform relative to the support or a movement of the support relative to the platform, effectively dispersing, absorbing, redirecting, reorienting, or displacing the force, F, within the medium.

20 Claims, 49 Drawing Sheets

(51) Int. Cl.
*A61M 16/00* (2006.01)
*A61M 16/04* (2006.01)
*A61M 16/20* (2006.01)
*H02J 7/35* (2006.01)
*H02J 7/34* (2006.01)
*H01M 10/46* (2006.01)
*A61M 16/10* (2006.01)

(56) References Cited

U.S. PATENT DOCUMENTS

| | | | | |
|---|---|---|---|---|
| 4,319,412 A * | 3/1982 | Muller | ............... | A43B 23/20 36/29 |
| 4,399,575 A * | 8/1983 | Hall | ............... | A47C 27/085 5/682 |
| 4,411,033 A * | 10/1983 | Morgan | ............... | A47C 27/085 428/12 |
| 4,655,213 A * | 4/1987 | Rapoport | ............... | A61M 16/0063 128/205.25 |
| 4,663,789 A * | 5/1987 | Smith | ............... | A47C 27/088 5/683 |
| 4,864,737 A * | 9/1989 | Marrello | ............... | A43B 13/20 36/29 |
| 5,152,020 A * | 10/1992 | Sobie | ............... | A47C 27/085 156/300 |
| 5,152,081 A * | 10/1992 | Hallenbeck | ............... | A43B 1/0009 36/114 |
| 5,176,618 A * | 1/1993 | Freedman | ............... | A61F 5/56 600/12 |
| 5,224,278 A * | 7/1993 | Jeon | ............... | A43B 13/203 36/27 |
| 5,238,006 A * | 8/1993 | Markowitz | ............... | A61N 1/0519 600/377 |
| 5,466,193 A * | 11/1995 | Hixson | ............... | A63D 1/04 473/115 |
| 5,595,003 A * | 1/1997 | Snow | ............... | A43B 13/181 36/27 |
| 6,029,962 A * | 2/2000 | Shorten | ............... | B29C 66/54 267/145 |
| 6,385,864 B1 * | 5/2002 | Sell, Jr | ............... | A43B 13/20 36/29 |
| 6,457,261 B1 * | 10/2002 | Crary | ............... | A43B 13/181 36/114 |
| 6,530,564 B1 * | 3/2003 | Julien | ............... | A43B 13/186 267/147 |
| 6,568,102 B1 * | 5/2003 | Healy | ............... | A43B 13/187 36/27 |
| 6,968,636 B2 * | 11/2005 | Aveni | ............... | A43B 7/1465 36/114 |
| 7,353,826 B2 * | 4/2008 | Sleeper | ............... | A61M 16/0833 128/207.18 |
| 7,481,224 B2 * | 1/2009 | Nelson | ............... | A61N 2/004 128/897 |
| 7,487,777 B2 * | 2/2009 | Gunaratnam | ............... | A61M 16/0057 128/206.24 |
| D589,140 S * | 3/2009 | Guney | ............... | D24/110.5 |
| 7,518,294 B2 * | 4/2009 | Umetsu | ............... | H03H 3/02 29/25.35 |
| 7,581,542 B2 * | 9/2009 | Abramson | ............... | A61F 5/566 128/848 |
| 7,608,314 B2 * | 10/2009 | Plant | ............... | A41D 31/285 428/86 |
| 8,756,834 B1 * | 6/2014 | Halberstadt | ............... | A43B 13/04 36/59 R |
| 10,232,221 B1 * | 3/2019 | Grayston | ............... | A43B 13/185 |
| 10,293,565 B1 * | 5/2019 | Tran | ............... | A43B 3/0005 |
| 2002/0073579 A1 * | 6/2002 | Lombardino | ............... | A43B 13/182 36/28 |
| 2003/0104164 A1 * | 6/2003 | Wu | ............... | A43B 13/182 428/102 |
| 2004/0068892 A1 * | 4/2004 | Wang | ............... | A43B 13/182 36/28 |
| 2004/0171321 A1 * | 9/2004 | Plant | ............... | A41D 31/285 442/64 |
| 2006/0234012 A1 * | 10/2006 | Wang | ............... | A43B 13/20 428/188 |
| 2007/0039204 A1 * | 2/2007 | Wyszynski | ............... | A43B 13/181 36/28 |
| 2007/0256326 A1 * | 11/2007 | Jarvis | ............... | A43B 13/226 36/28 |
| 2007/0277401 A1 * | 12/2007 | Young-Chul | ............... | A43B 13/186 36/30 R |
| 2008/0263894 A1 * | 10/2008 | Nakano | ............... | A43B 21/26 36/28 |
| 2011/0131831 A1 * | 6/2011 | Peyton | ............... | A43B 13/18 36/29 |
| 2012/0260524 A1 * | 10/2012 | Izquieta Anaut | ............... | B29D 35/142 36/28 |
| 2013/0061495 A1 * | 3/2013 | Lubart | ............... | A43B 23/222 36/103 |
| 2013/0160324 A1 * | 6/2013 | Peyton | ............... | A43B 13/203 36/83 |
| 2013/0160329 A1 * | 6/2013 | Peyton | ............... | A43B 13/28 36/105 |
| 2014/0130269 A1 * | 5/2014 | Dabah | ............... | A43B 13/181 12/142 R |
| 2014/0202031 A1 * | 7/2014 | Seo | ............... | A43B 13/026 36/28 |
| 2014/0250726 A1 * | 9/2014 | Meschter | ............... | A43B 13/20 36/102 |
| 2014/0331517 A1 * | 11/2014 | Seo | ............... | A43B 13/20 36/28 |
| 2015/0113828 A1 * | 4/2015 | Yang | ............... | A43B 13/18 36/28 |
| 2016/0192739 A1 * | 7/2016 | Hoffer | ............... | A43B 13/122 36/28 |
| 2016/0242502 A1 * | 8/2016 | Spanks | ............... | B33Y 80/00 |
| 2016/0270477 A1 * | 9/2016 | Kurosaki | ............... | A43B 13/181 |
| 2016/0295960 A1 * | 10/2016 | Rushbrook | ............... | A43C 15/161 |
| 2016/0331077 A1 * | 11/2016 | Park | ............... | A43B 7/144 |
| 2016/0360830 A1 * | 12/2016 | Mitsui | ............... | A43B 5/00 |
| 2017/0071289 A1 * | 3/2017 | Auyang | ............... | A43B 13/188 |
| 2017/0135439 A1 * | 5/2017 | Davis | ............... | A43B 13/12 |
| 2017/0231322 A1 * | 8/2017 | Gheorghian | ............... | A43B 13/125 267/141 |
| 2018/0213886 A1 * | 8/2018 | Connell | ............... | A43B 13/125 |
| 2018/0368514 A1 * | 12/2018 | Nishiwaki | ............... | A43B 7/32 |
| 2018/0368516 A1 * | 12/2018 | Mason | ............... | A43B 13/04 |

* cited by examiner

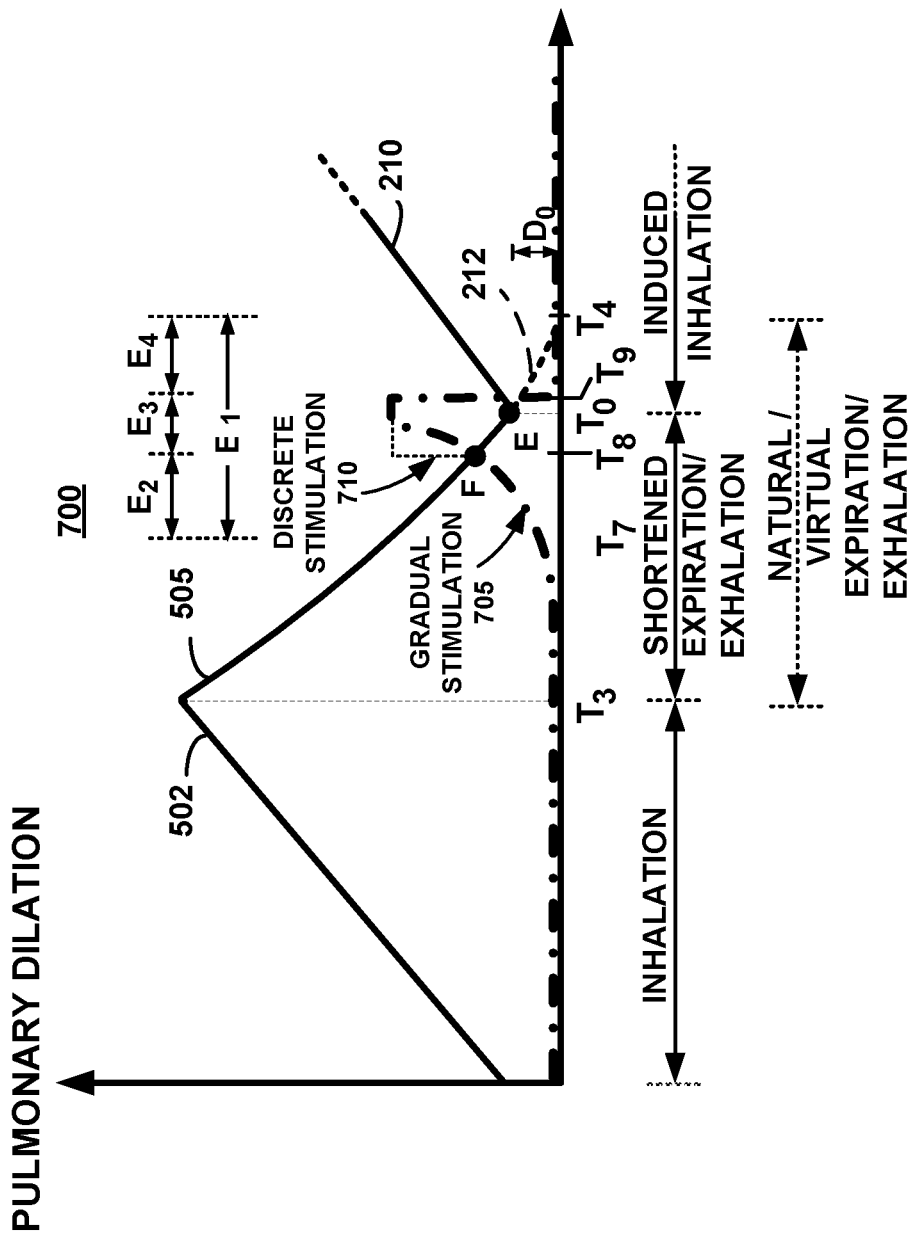

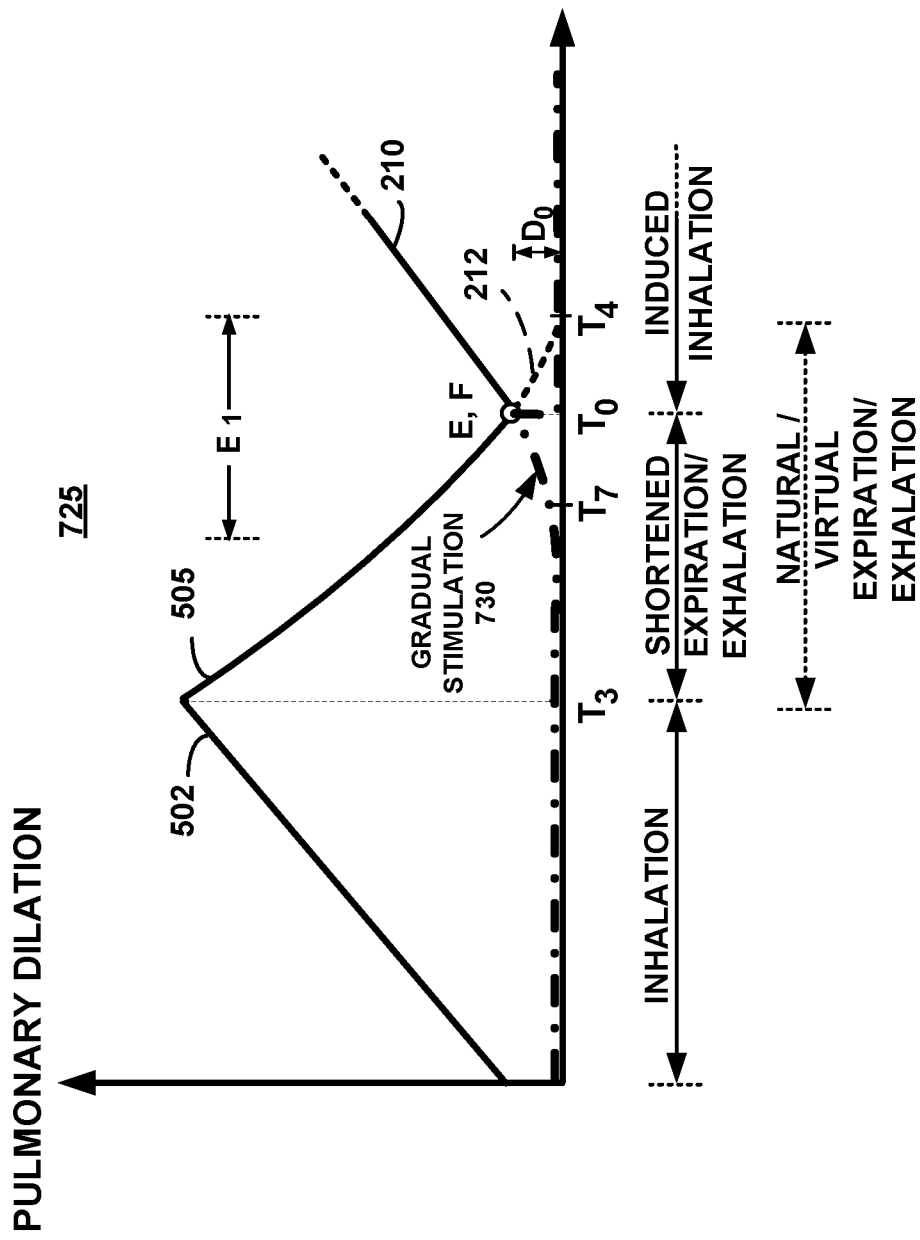

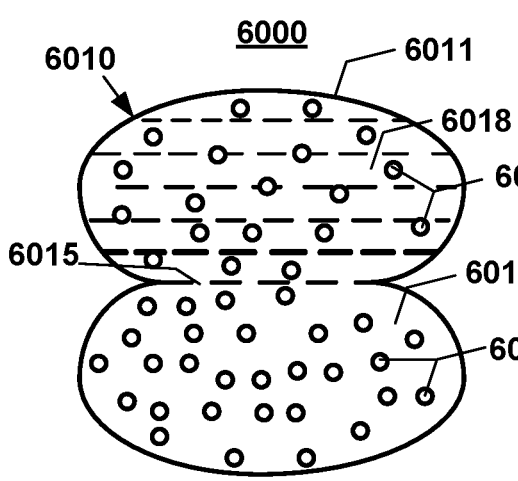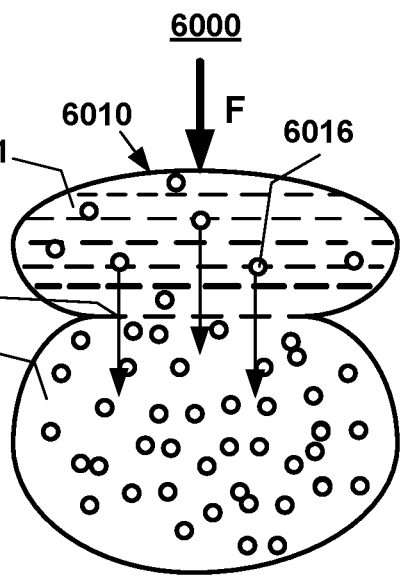
FIG. 60  FIG. 61
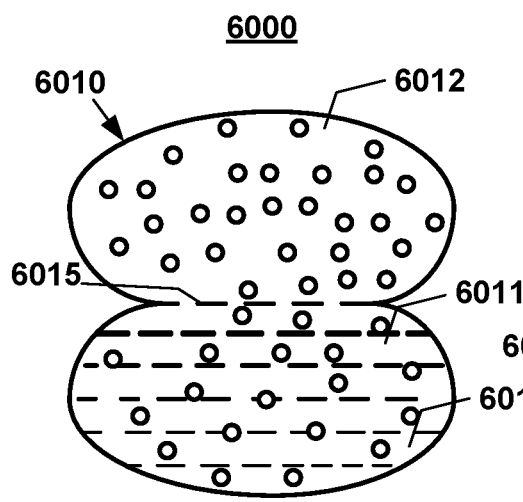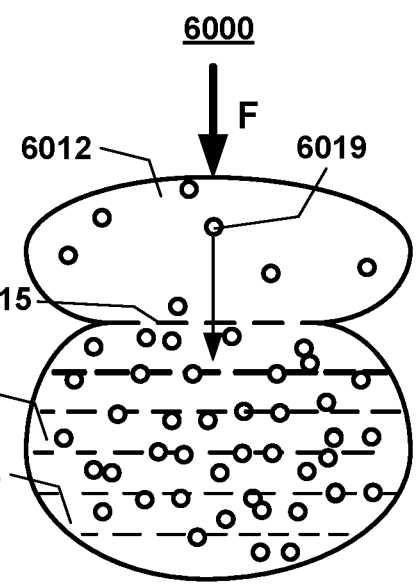
FIG. 62  FIG. 63

FOOTWEAR AUXILIARIES FOR SYNCHRONOUSLY TONING LEG MUSCLES IN ORDER TO STRAIGHTEN BACK POSTURE

PRIORITY AND RELATED APPLICATION

The present application is a continuation-in-part of co-pending U.S. patent application Ser. No. 13/889,316, filed on May 7, 2013, which is incorporated herein by this reference in its entirety.

FIELD OF THE INVENTION

The present invention generally relates to footwear, and more particularly to footwear auxiliaries that synchronously tone the leg muscles in order to straighten the back posture.

BACKGROUND

Shoe insoles and various sole designs have been used to provide shock absorbing features and thus reduce fatigue. With the miniaturization of electronic devices and the popularization of light emitting diodes (LEDs), shoe manufacturers have been trying to incorporate these electronics and LEDs in the shoe design for marketing purposes. An example of miniaturized electronics being incorporated within the shoe design is described in U.S. patent application Ser. No. 15/288,472 filed on Oct. 7, 2016, and generally describes a sensor system for transferring performance data.

However, the conventional footwear designs do not effectively target the toning of the leg muscles in order to effect straightening of the back posture.

Sleep apnea is a breathing disorder characterized by brief disruptions of breathing during sleep. When a person stops breathing during sleep due to sleep apnea, the balance of oxygen and carbon dioxide in the blood is upset. This imbalance stimulates the brain to restart the breathing process. The brain signals the person to wake up so that the muscles of the tongue and throat can increase the size of the airway, by allowing carbon dioxide to escape and oxygen to enter the airway. These waking episodes are necessary to restart breathing, disrupt sleep, and may cause daytime exhaustion.

There are two types of sleep apnea: central and obstructive. Obstructive Sleep Apnea (OSA) and Central Sleep Apnea (CSA). OSA is the most common type of sleep apnea. It is caused by a breathing obstruction, which stops the airflow in the nose and mouth. CSA is less common than OSA, and is manifested as a central nervous system disorder that occurs when the brain signal telling the body to breathe is delayed. CSA can be caused by disease or injury involving the brainstem, such as a stroke, a brain tumor, a viral brain infection, or a chronic respiratory disease.

While the causes of apnea are different in CSA and OSA, the symptoms and results are generally similar, namely a deprivation of oxygen and poor sleep. The treatments for CSA include medications that stimulate the need to breathe and administration of oxygen. As used herein, sleep apnea includes either CSA or OSA.

Normally, the muscles of the upper part of the throat keep the airway open to permit airflow into the lungs. When the muscles of the upper airway relax and sag, the relaxed tissues may vibrate as air flows past the tissues during breathing, resulting in snoring.

When a person has OSA, the throat collapses during sleep, blocking the airway and preventing air from getting to the lungs. Generally, the throat muscles keep the throat and airway open. The resulting effect of OSA could become serious.

Exemplary sleep apneas treatment devices are described in the following publications: U.S. Pat. Nos. 4,655,213; 5,176,618; 5,238,006; 5,466,193; 7,353,826; 7,481,224; 7,487,777; 7,578,013; 7,578,294; 7,581,542; and D589140. Although several treatment devices have been described, the most common devices are classified into three categories: CPAP; dental appliances, oral devices, and lower jaw adjustment devices; and surgery.

CPAP (Continuous Positive Airway Pressure) is widely recommended for moderate to severe obstructive sleep apnea. CPAP entails wearing a mask-like device (or nose pillows) during sleep, in order to provide continuous, positive, pressurized air to prevent the airway from collapsing. While CPAP has proven to be effective for numerous patients, many people find the apparatus uncomfortable and awkward to use, particularly due to air leaks at higher pressures. Some improvements to the CPAP technology include options such as: "bilevel PAP," which switches from higher to lower air pressure during the expiration; and "AutoPAP," which uses an internal regulator that adjusts pressure rather than remaining at one fixed setting. Nonetheless, CPAP, as its name indicates, still uses "continuous" positive pressure.

Dental appliances, oral devices, and lower jaw adjustment devices may be made of acrylic and fit inside the mouth. Two oral devices that are commonly used are the mandibular repositioning device and the tongue-retaining device. These oral devices open the airway by bringing the lower jaw or tongue forward during sleep. While oral devices are more convenient to use than CPAP, they are generally more effective for mild to moderate sleep apnea cases. A number of side effects may result from the use of the dental appliances, such as soreness, and damage to, or permanent change in position of the jaw, teeth, and mouth; saliva build-up; and nausea.

Surgery can increase the size of the patient's airway. The surgeon may remove tonsils, adenoids, or excess tissue at the back of the throat or inside the nose. The surgeon may reconstruct the jaw to enlarge the upper airway. Surgery may be an effective option for some patients; however, surgery carries the risks of surgical complications and infections.

While the foregoing treatment devices are useful for their intended purposes, there remains an unsatisfied need for a simple, cost-effective device, system, and method for reducing sleep disordered breathing events.

In addition to the foregoing sleep disorder related concerns, another problem arises for patients who use current respiratory devices, namely the portability of the CPAP machines. A representative portable CPAP machine is the Transcend CPAP, which is described at the following web site: http://www.mytranscend.com/patients/why-transcend/, as having the following dimensions: 6.1"×3.5"×2.8". Although this device is relatively small, an extended use of this product may require an external battery, which adds to the size and weight of the CPAP machine. In addition, some of the limitations to the miniaturization of the Transcend CPAP may be: the continuous operation of the pump, the power supply, the pump design, and the electronic circuitry.

Therefore, there still remains an unsatisfied need for a simple, cost-effective portable breathing aid device, system, and method for more efficiently and economically providing added comfort to the users.

BRIEF SUMMARY

The present disclosure presents footwear designs and various auxiliaries that effectively target the toning of the leg muscles in order to straighten the back posture. To this end, a shoe sole is provided with a redress mechanism comprised of devices for redressing the positions of the shoe soles, in order to adjust the corresponding feet positions.

One of the main goals of the redress mechanism is to cause the constituent devices to force the sole axes to rotate by appropriate angles, so that they become aligned with the respective redress axes. In addition, the redress devices will exert the necessary attraction forces to maintain the shoe soles in the redress positions, for an extended period of time in order to cause the complimentary skeletal muscles to be toned and consequently assume the redress action on their own. According to another embodiment, the redress mechanism does not provide the attraction forces, but rather provides the user with a feedback signal or message when the shoe soles become misaligned (within a certain range) relative to the redress axes, to advise the user that an adjustment is needed.

According to the latter embodiment, the constituent devices of the redress mechanism include sensors that operate in conjunction with each other to generate a feedback signal whenever the two soles are not within the parameters of a predetermined redress position. One or more processors may be integrated as part of the constituent devices to evaluate the feedback signals generated by the sensors, and to forward the appropriate warning signal to a user feedback device, via one or more transceiver.

In a more simplified design, only one processor and one transceiver may be used. In an alternative embodiment, the processors are eliminated altogether, and the raw signals are transmitted directly to an external feedback device for processing and determination of the proximity of the two constituent devices relative to each other. These raw signals may be transmitted, wirelessly through one or more transceivers to either the user through the external feedback device, or to one or more posture adjustment mechanisms that provide automatic redress.

A rechargeable power cell may be used within each constituent device to power the sensors, the transceivers, and the posture adjustment mechanisms. A separate rechargeable power cell may be used to power the feedback device. Some or all of the rechargeable power cells may be of the type described herein, using the body's own temperature heat, foot pressure, or any other source described herein.

The present disclosure further describes shock absorbent "pebbles" that can be incorporated or formed within a medium or used separately, according to one embodiment of the present disclosure. An exemplary pebble is generally formed of an elastic membrane that deforms under pressure, and that defines two (or more) chambers that are connected with a gas permeable membrane. The membrane is permeable to air (or gas) but not to liquid. In a resting position, the first chamber is filled with a mixture of gas along with liquid. The second chamber is filled with the same (similar or dissimilar) gas as the gas. Both chambers remain at equilibrium until an external force is applied to the first chamber and/or to the second chamber. In one embodiment, the fluid may be agrose gel.

As an external force is applied to the first chamber, the fluid contained therewithin may not be compressed, but the gas may be compressed. As a result, at least some of the gas molecules are forced into the second chamber, inflating it until such time as the external force is balanced by the gas pressure in the second chamber, at which time the flow of the gas molecules from the first chamber to the second chamber stops. In consequence, the external force is absorbed by the pebble. The pebble may be micro-sized (as a micro-capsule) for distribution over a large area, or sized according to the desired application.

The present invention satisfies the foregoing need, and presents a device, system, and method for reducing sleep disordered breathing events (collectively referred to herein as "DPAP device", "the present DPAP device", or "Discontinuous Positive Airway Pressure Device").

The present DPAP device provides selective excitation to the pharyngeal conduit or another muscle or cartilage along the respiratory path, a predetermined period of time before the end of the expiration stage, in order to prematurely reverse the respiratory cycle before the total collapse of the pharyngeal conduit, thus enabling the inhalation stage to reopen and refill the pharyngeal conduit.

According to other embodiments of the present invention, the excitation source includes a puff of positive air pressure, oxygen, another gas, electrical, and/or an audible (or sound) vibratory wave.

According to still other embodiments, the excitation source is applied to pharyngeal conduit, the tongue, the palate, the epiglottis, salivary glands, and/or other muscles or cartilages that can cause the premature reversal of the respiratory cycle.

According to yet another embodiment, the DPAP device is a relatively small, portable, user-wearable, rechargeable, and cost-effective breathing aid (or assist) device that efficiently and economically provides added comfort to the user. The DPAP device induces a premature inhalations cycle, as needed, to avoid having the brain signal the user to wake up so that the muscles of the tongue and throat can increase the size of the airway.

To this end, the DPAP device includes a sensor that identifies a breathing back pressure below a predetermined threshold, as the exhalation cycle approaches its virtual end.

The stimulation provided by the DPAP device can be either gradual (i.e., soft) or stepped (i.e., hard). When using the gradual stimulation, if after a predetermined time period the induced (or natural) inhalation cycle does not start, then the DPAP device has the following two alternative options:
  The first option is for the DPAP device to continue the course of the gradual stimulation until it reaches a sufficient stimulation level.
  The second option is for the DPAP device to apply a discrete stimulation that induces the premature inhalation.

According to a preferred embodiment, the DPAP device uses a dental appliance. The dental appliance may be made integrally with, and of the same material as the oral tube. The dental appliance includes a formable or compliant section that fits over the user's teeth or gum, and an internal extension. The dental appliance includes an opening that enables the stimulation to be nozzled out of an outlet opening, directionally toward an intended target stimulation area.

According to a specific embodiment, the DPAP device establishes a wireless (or remote) communication with an external communication device, such as a smart phone and/or an external processor.

During regular breathing events, the teeth slightly pressed against the pliable section and deform it slightly so that it forms a resting seat for the upper teeth. During regular breathing events, the pliable section of the resting seat does not restrict the flow of fluid within the oral tube. The dental appliance maintains the upper and lower teeth slightly separated.

The dental appliance includes a valve is normally closed as long as the user does not grind the upper and lower teeth. The grinding motion closes the pliable section of the resting seat, and a backpressure is built within the dental appliance. This back pressure causes the valve to open and to direct the stimulation toward the teeth. Once the grinding action stops, the flow through the nozzled opening resumes and the valve is closed.

According to another embodiment, the DPAP device is used with a nasal tube. The nasal tube is typically looped around the user's ears and delivers the stimulation to the nasal cavity. As the stimulation enters the nasal cavity, it expands and vaporizes into particles that stimulate the user's olfactory senses and cause a reaction of the uvula, thus clearing the airways for breathing.

According to another embodiment it would be possible to incite the desired breathing response of a user, by stimulating various parts of the user's body, for example, the user's ear, the top of the head, or the scalp. The stimulation can be done by means of one or a plurality of holes, openings, or nozzles disposed along the nasal tube in order to allow at least some of the stimulation to escape and stimulate the target area.

According to another embodiment, one such opening is positioned in close proximity to the user's ears to generate an auditory stimulation, such as a high frequency pitch that causes the desired respiratory response.

Another DPAP device according to an alternative embodiment of the present invention, can be used as a retrofit to an existing CPAP device. The DPAP device makes use of the pumping force of the conventional CPAP device. The DPAP device includes a respiration sensor that can be worn by the user like a necklace due to its miniaturized size, as explained earlier. The respiration sensor senses the onset of the exhalation stage and the approach of the stimulation point, E. To this end, the sensor is connected to the nasal tube and is also connected to a valve via a fluid tube. The valve controls the flow of air from the CPAP device so that the DPAP device operates similarly to the DPAP device. The valve is connected at its other end, to the hose. The valve can include a flow reducer that controls the rate of flow, the volume, and the pressure of the stimulation.

According to another design, the sensor is connected to the control circuitry of the CPAP device. Alternatively, the operation of the CPAP device can be reprogrammed to respond to the sensor and to operate the CPAP device according to the teachings of the present invention.

According to a specific embodiment, the DPAP device includes an infusion pump with one or more inlet port and one or more outlet port that permit the exchange of fluid. The inlet port and the outlet port are concentric. In one specific embodiment, the infusion pump is a dual-spiral infusion pump In the latter embodiment, the DPAP device includes a power cell that comprises a rechargeable battery charged by two or more charging devices, such as a Seebeck charger and a solar charger.

According to another embodiment, the DPAP device is used with a smart phone and/or an external processor. The DPAP device includes the power cell that supplies the necessary power to a stimulation source, a respiration sensor, and a transceiver. The power cell further includes an additional charging element, namely a piezoelectric vibration element that converts the vibrations of the DPAP device into electrical current that further charges the rechargeable battery. The vibration frequency of the piezoelectric vibration element can be set to a predetermined resonance frequency that maximizes the resonance, and thus maximizes the energy conversion from vibration to electrical.

The power cell of the DPAP device may further include a heat absorbent surface or heat sink that absorbs externally generated heat.

The power cell of the DPAP device may further be provided with an inductive element that inductively interacts with a similarly and generally oppositely situated inductive element, to provide vibration to the piezoelectric vibration element, to heat the Seebeck charger, and wherein excess heat is absorbed by the heat absorbent surface, thus minimizing energy loss.

The DPAP device may be provided with a dual-spiral infusion pump. Alternatively, the DPAP device may be provided with an expansion dual-spiral pump.

According to another embodiment, the DPAP device may be provided with a dual function infusion/expansion pump. In operation, during the inhalation stage, the pump intakes air and compresses it for exhaust through the nasal tube. During the expiration stage, the exhaled carbon dioxide is pulled into the pump and expanded for exhaust.

According to still another embodiment, the DPAP device uses a pressurized cartridge as a stimulation source.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

FIGS. 3 and 4 are flow charts illustrating the process of using the DPAP device of FIG. 1 for reducing sleep disordered breathing events, as shown in the chart of FIG. 2, wherein FIG. 3 illustrates the general steps of a method for initializing the DPAP device of FIGS. 1 and 2, and further wherein FIG. 4 illustrates the general steps of a method using the DPAP device of FIGS. 1 and 2;

FIGS. 60, 61, 62, 63, 64, 65 illustrate alternative shock absorbent "pebbles" that can be incorporated or formed within the sole of FIG. 55, according to one embodiment of the present disclosure.

It should be understood that the sizes of the chart and the different components in the figures might not be in exact proportion, and are shown for visual clarity and for the purpose of explanation.

DETAILED DESCRIPTION OF PREFERRED EMBODIMENTS

Reference is made herein to two related U.S. Pat. Nos. 5,578,077 and 8,215,302, both of which are incorporated herein by this reference, in their entirety.

Figure 1:
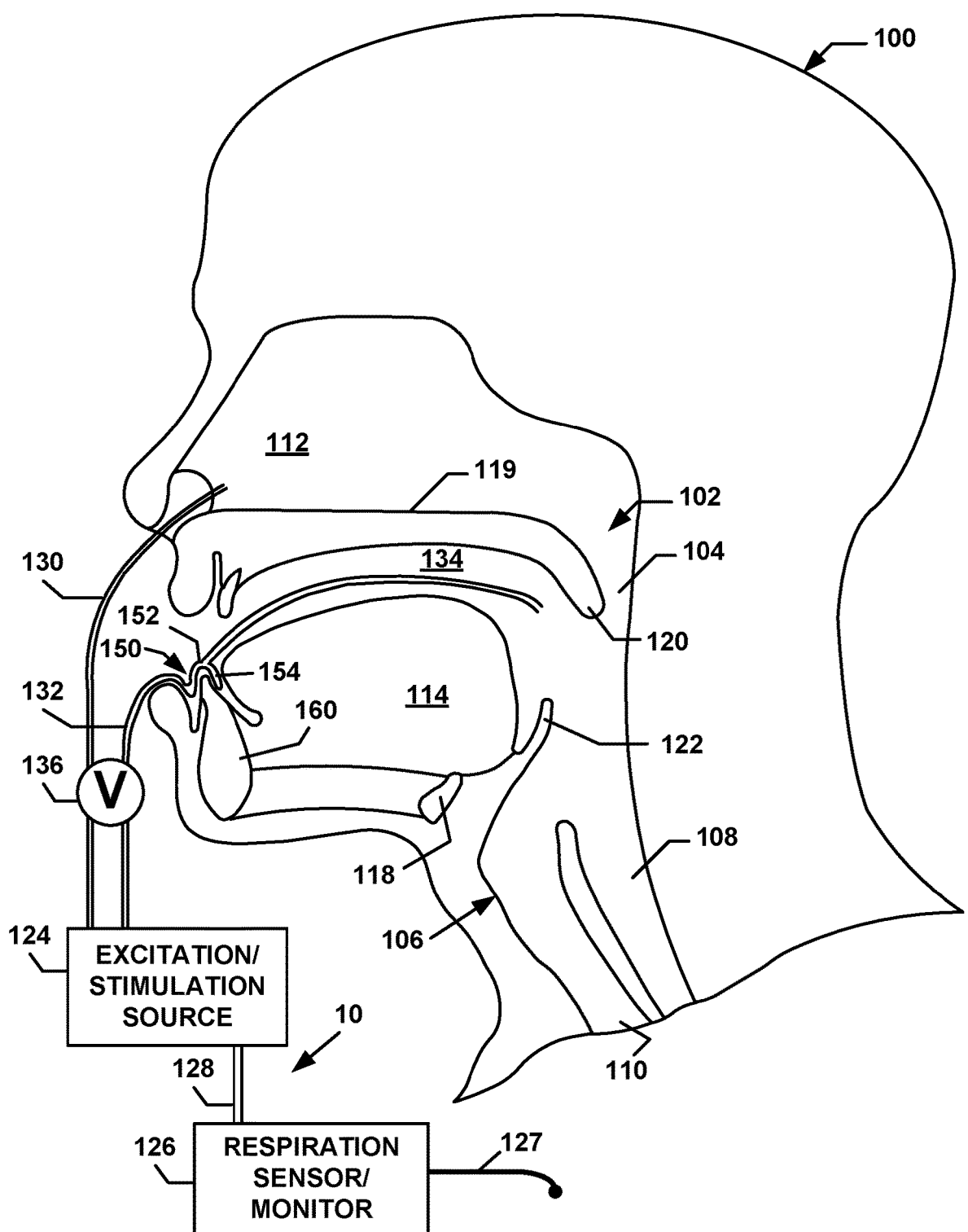
FIG. 1 is a side, cross-sectional, elevational view of a person's head showing a DPAP device according to the present invention.

FIG. 1 is a side view of a person's head 100 showing the placement of a DPAP device 10 according to the present invention. The person's upper airway 102 includes the pharynx 104 that splits into the larynx/trachea 106 and the esophagus 108. Although the tissue along this airway is responsive to the respiratory cycle, only the pharyngeal conduit 110, that includes the tissues in the region of the upper airway 102 that starts behind the nasal cavity 112 and ends in its connections to the larynx 106, is totally collapsible.

The pharyngeal structure and individual anatomic components within the upper airway 102 include the pharyngeal walls; the base of the tongue 114; the vallecula (or epiglottic vallecula); the hyoid bone 118 and its attachments; the soft palate 119 with uvula 120, the palatine tonsils with associated pillar tissue; and the epiglottis 122.

Figure 2:
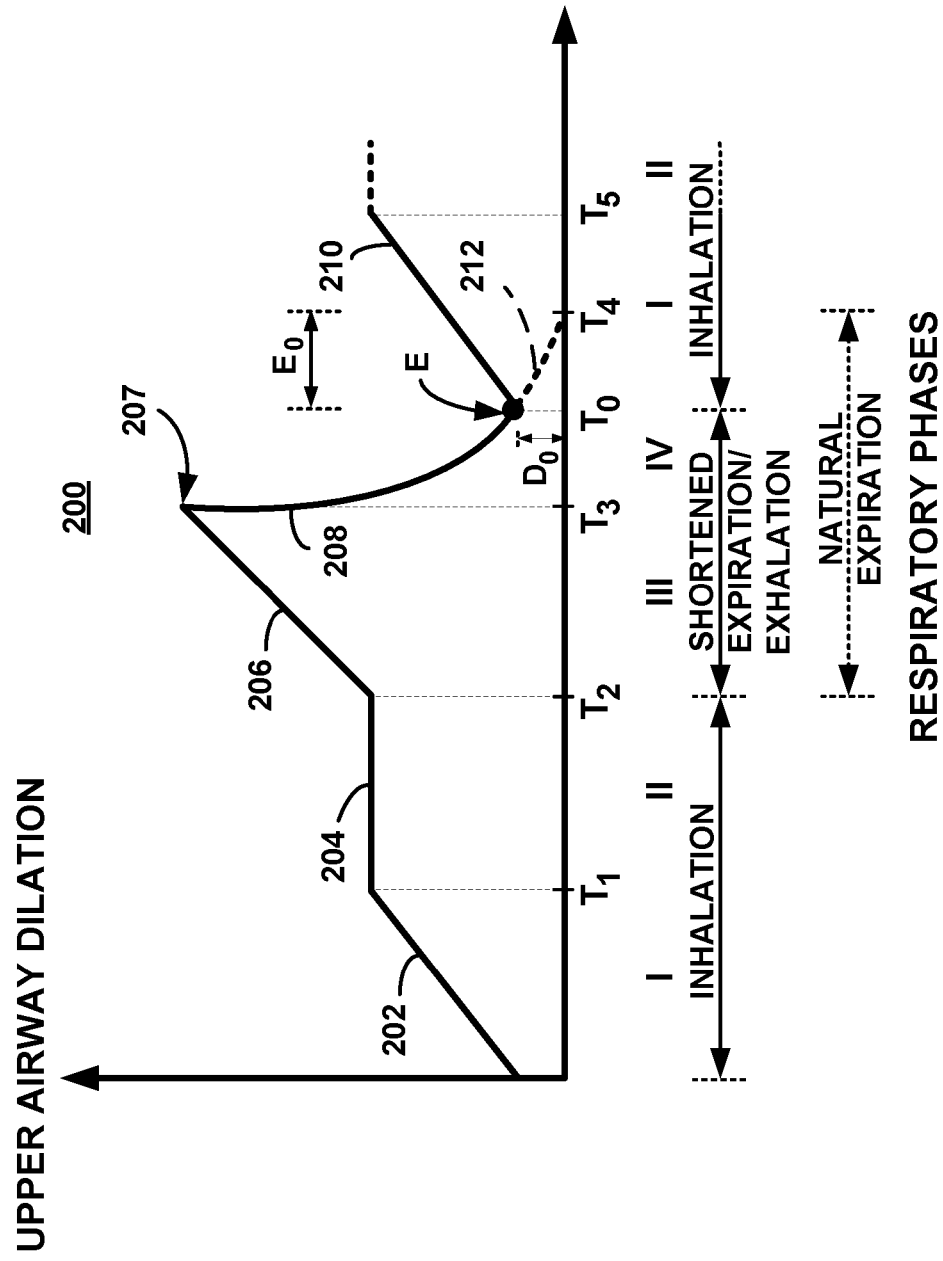
FIG. 2 is a graph illustrating the respiratory cycle using the DPAP device of FIG. 1.

FIG. 2 is a chart that illustrates an exemplary respiratory cycle 200 using the DPAP device 10 of FIG. 1 according to the present invention. This chart illustrates the variation (or dilation) of the cross-sectional area of the upper airway 102, with respect to the various phases of the respiratory cycle 200. At the initiation of inspiration (Phase I), and as illustrated by the segment 202, which ends at $T_1$, the upper airway 102 begins to dilate. Thereafter, and as illustrated by the segment 204, that ends at $T_2$, the upper airway 102 remains relatively constant through the remainder of inspiration (Phase II).

At the onset of expiration (Phase III), and as illustrated by the segment 206, that ends at $T_3$, the upper airway 102 begins to enlarge or dilate, reaching a maximum diameter at point 207. The upper airway 102 then starts to diminish in size, as illustrated by the segment 208, so that at the end of the natural expiration, without the corrective excitation of the present invention), it is at its narrowest, corresponding to the time $T_4$ when the upper airway (102) dilator muscles are least active, and positive intraluminal pressure is lowest.

The pharyngeal conduit 110 has the greatest potential for collapse and closure at the end of the expiration stage (at time $T_4$). The dilator muscle activation is directly related to airway narrowing and reduces resistance across patients with obstructive sleep apnea. R. Pierce, et al., "Upper Airway Collapsibility, Dilator Muscle Activation And Resistance In Sleep Apnoea," European Respiratory Journal, Volume 30, Number 2, pages 345-353 (2007).

Sleep is characterized by a reduction in upper airway dilator muscle activity. For the person with obstructive sleep apnea (OSA), it is believed that this change in muscle function causes pharyngeal narrowing and collapse. Current studies seem to support that OSA patients have an intrinsically structurally narrowed and more collapsible pharynx. Isono S., et al., "Anatomy of Pharynx in Patients with Obstructive Sleep Apnea and in Normal Subjects," J Appl. Physiol. 1997: 82:1319-1326.

Although anatomic closure is often accentuated at specific sites, such as the velopharyngeal level, studies of closing pressures show that the narrowing and collapse usually occurs along the entire length of the pharynx 104. Shellock F. G., et al., "Occlusion and Narrowing of the Pharyngeal Airway in Obstructive Sleep Apnea: Evaluation by Ultrafast Spoiled GRASS MR Imaging," Am J of Roentgenology 1992:158:1019-1024.

The DPAP device 10 reduces sleep disordered breathing events by selectively providing excitation to the pharyngeal conduit 110 or another muscle, cartilage, or element along the respiratory path of the upper airway 102 (collectively referred to herein as "selective elements of the pharyngeal conduit"). This excitation is introduced at an optimal excitation point, E, at time $T_0$, which is selected at a predetermined, but short, excitation period of time (or stimulation zone) $E_0$, before the virtual end, $T_4$, of the natural expiration stage. $T_0$-$T_4$ [$T_4$] is also referred to herein as "the virtual period".

The application of the excitation can also be quantified as a measure of the dilation of the pharyngeal conduit 110. In a preferred embodiment, the excitation (or stimulation) is applied as the dilation of the pharyngeal conduit 110 reaches approximately $D_0$. As a result, the excitation point E could be determined as a function of two parameters, the dilation $D_0$ and the excitation period $E_0$: $E(D_0, E_0)$.

These two parameters ($D_0$, $E_0$) vary for each individual, and are thus personalized. The selection of the excitation point E enables the premature reversal of the respiratory cycle before the total collapse of the pharyngeal conduit 110, and shortens the natural occurrence of the expiration or exhalation stage. As a result of such reversal, the inhalation stage is prematurely introduced, at about substantially the optimal excitation period $E_0$ prior to its natural initiation. The premature initiation of the inhalation phase (Phase I) prematurely reopens and commences the inflation of the pharyngeal conduit 110, prior to the expected total or substantial collapse of the pharyngeal conduit 110. The premature inflation of the pharyngeal conduit 110 prevents the occurrence of the apneic events.

More specifically, and still with reference to FIG. 2, the expiration stage is cut off at time $T_0$. Rather than allowing the pharyngeal conduit 110 to follow its natural course and dilate, or more accurately deflate, following the path 212 (shown in dotted lines), the pharyngeal conduit 110 is forced to be inflated along the path 210 (that ends at $T_5$). Consequently, according to the present invention, the expiration stage (phases III and IV) is shortened relative to the natural, uncorrected, expiration cycle, in order to provide the corrective treatment.

If the pharyngeal conduit 110 were allowed to collapse totally or substantially, then it would require air at higher pressure to cause it to open. However, if the pharyngeal conduit 110 were allowed to partially collapse, the pressure required to open it and to inflate it would be significantly less than that required under the total collapse. As a result, the timing of the excitation according to the present invention is important to reduce the magnitude or amplitude of the excitation.

To this end, the DPAP device 10 includes an excitation (or stimulation) source 124 that is connected to a respiration sensor (or monitor) 126 via cables or fluid conduits 128 (that conduct a fluid or a gas). The respiration sensor 126 is provided with electrodes 127 that collect the desired respiration parameters, in order to allow the practitioner to personalize the optimal excitation point E for each individual.

One (or two) nasal tube (mask or wire) 130 is connected to the excitation source 124 at one end, with its other end partly inserted in (or covering) the nasal cavity 112. According to another preferred embodiment, an oral tube or an electrical wire 132, or a dental appliance 150, is connected to the excitation source 124 at one end, with its other end partly inserted in (or covering) the mouth 134. According to still another embodiment, both the nasal tube 130 and oral tube 132 are connected to the excitation source 124, by means of a valve 136.

Considering now the respiration sensor/monitor 126, its main functions are: (1) upon initialization of the DPAP device 10 for the first time, the respiration sensor/monitor 126 assists the practitioner to determine the optimal excitation point E for the particular use of the DPAP device 10; and (2) for the normal use of the device, the respiration sensor/ monitor 126 confirms the occurrence or presence of the excitation point E, and upon such confirmation it provides the necessary excitation to the user of the DPAP device 10.

The respiration sensor/monitor 126 uses the electrodes 127 to monitor the respiratory cycle 200, and the progress of its four phases (I, II, III, IV), as is known or available in the field. As an example, the respiration sensor/monitor 126 monitors the variations in the relative position of the chest (as is currently done in a sleep study) in order to calculate the occurrence of the parameters of the excitation point E: the dilation $D_0$ and the excitation period $E_0$: $E(D_0, E_0)$.

According to another embodiment of the present invention, the respiration sensor/monitor 126 provides a feedback as to the efficacy of the excitation provided by the DPAP device 10 so as to vary the dilation $D_0$ and the excitation period $E_0$: $E(D_0, E_0)$ of the excitation point E.

As an example, under certain conditions, such as when the individual or user is sick and his/her respiration cycle does not follow the normal respiratory cycle. As an illustration, if the respiration sensor/monitor 126 determines the virtual time $T_4$, when the upper airway (102) dilator muscles are expected to be least active, and the positive intraluminal pressure is the lowest (from previous measurements during respiratory cycles), and further determines that this virtual time $T_4$ is different from the usual or normal virtual time $T_4$ that was determined at the initialization stage, then the respiration sensor/monitor 126 could automatically adjust the dilation parameter $D_0$ of the pharyngeal conduit 110 accordingly.

As another illustration, the respiration sensor/monitor 126 determines variations from the norm of the dilation parameter $D_0$ of the pharyngeal conduit 110, then it could automatically adjust the virtual time $T_4$, could accordingly. In a preferred embodiment, the dilation $D_0$ exceeds approximately 1 mm and the excitation period $E_0$ exceeds approximately 1 millisecond.

Considering now the excitation source 124 could provide a variety of excitations, some of which are: a puff of positive air pressure, oxygen, another gas, electrical, and/or an audible (or sound) vibratory wave. To this end, in order for the excitation source 124 to provide a short puff of air or gas (i.e., oxygen or another gas), the excitation source 124 includes a pump similar to that used in the CPAP device.

One distinction between the common CPAP device and the DPAP device 10 of the present invention is that in the present DPAP device 10 the puff of positive air is discontinuous, that is a puff of air is delivered at the desired pressure but only for a very short period of time, such as 0.5 second. Another desirable feature of the present DPAP device 10 is that the air puff pressure that this delivered intermittently (or periodically) could be lower than the pressure at which air is continuously delivered by the CPAP device, in that the air puff is delivered at the optimal excitation point E, prior to the collapse of the pharyngeal conduit 110.

According to another embodiment, in order for the excitation source 124 to provide an electrical excitation, the excitation source 124 includes an electrical stimulation device, such as those used, for example, in cardiac pacemakers or tachycardia devices.

According to still another embodiment, in order for the excitation source 124 to provide an audible (or sound) vibratory wave, the excitation source 124 includes a sound pressure pump capable of generating vibratory waves, such as sound waves or other audible waves that are not limited to the audible frequency spectrum. The vibratory frequencies of the waves are selected to selectively cause selected elements, muscles, ligaments, cartilage, or cavities to vibrate or resonate.

For example, the excitation source delivers a wave at, or about, the resonance or vibration frequency of the nasal cavity 112, at the excitation point E. According to still other embodiments, the excitation source 124 delivers a wave at, or about, the resonance or vibration of the pharyngeal conduit 110, the tongue 114, the palate 119, the epiglottis, the uvula 120, the salivary glands, the larynx/trachea 106, the esophagus 108, and/or other muscles or cartilages, including the hyoid bone 118, that can cause the premature reversal of the respiratory cycle 200, as described earlier.

In a specific preferred embodiment where the dental appliance 150 is used in conjunction with the oral tube 132 for delivering the puff of gas, the dental appliance 150 may be made of the same material as the oral tube 132 for allowing the gas to pass therethrough. It includes a formable or compliant section 152 that fits over the user's teeth or gum 160, and an internal extension 154. An oral extension extends from, and is in fluidic communication with the oral tube 132 via the compliant section 152, into the user's mouth 134.

Figure 3:
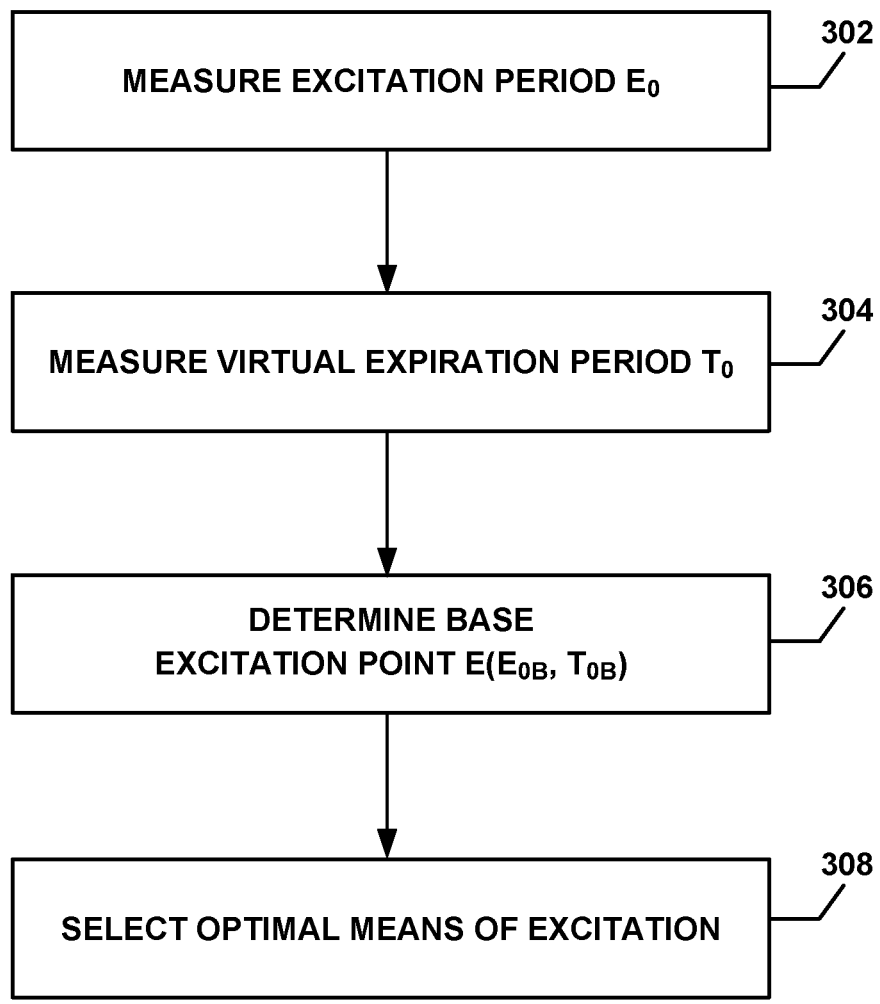
Figure 4:
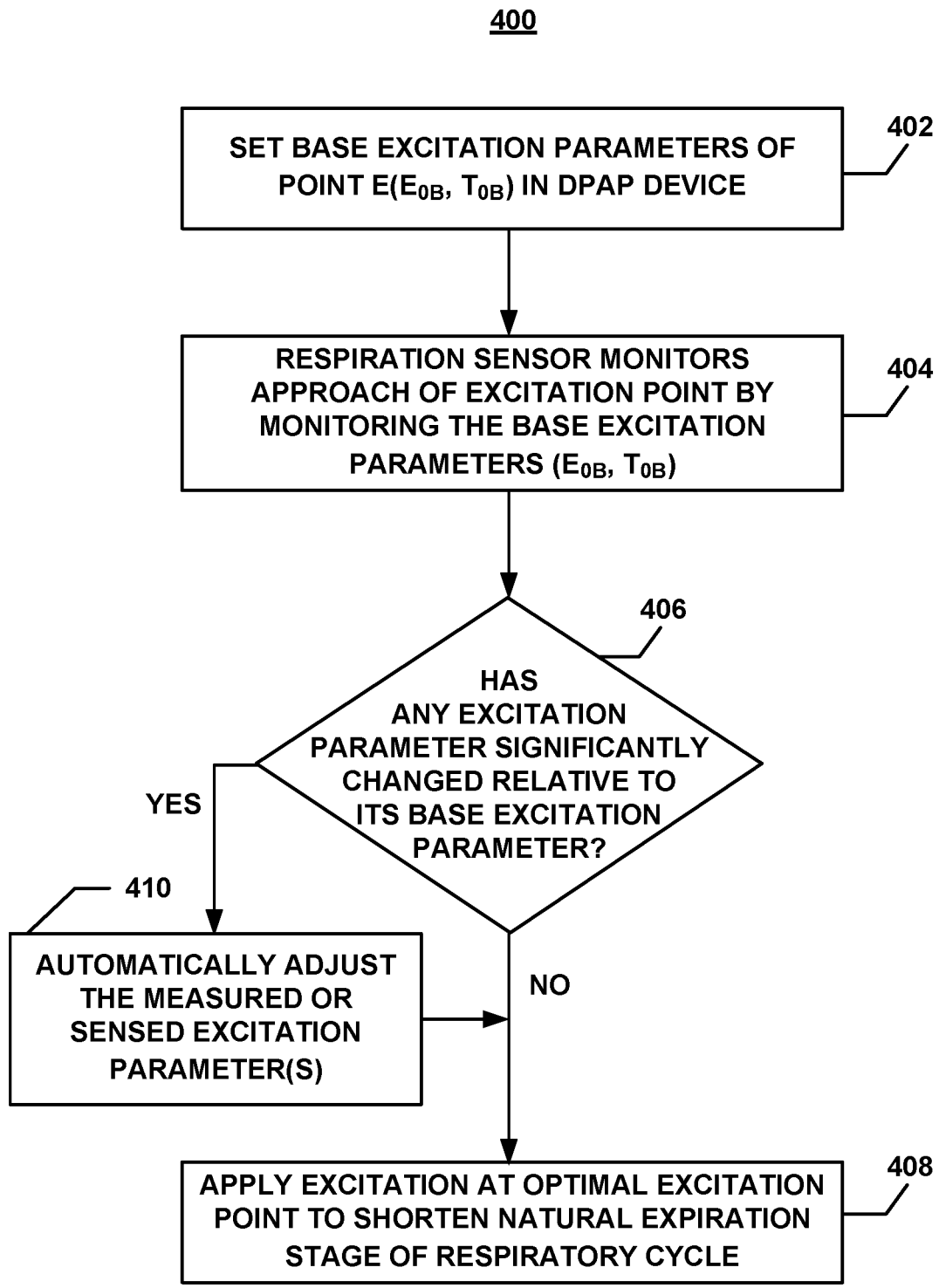

FIGS. 3 and 4 are flow charts illustrating the process of using the DPAP device 10 of FIG. 1 for reducing sleep disordered breathing events, as shown in the chart of FIG. 2. More specifically, FIG. 3 illustrates a method 300 for initializing the DPAP device of FIGS. 1 and 2.

At step 302, method 300 measures the base excitation period $E_{OB}$, pursuant to the chart of the respiratory cycle 200 of FIG. 2. At step 304, method 300 measures the base virtual period $T_{4B}$. Based on these parameters of the base excitation period $E_{OB}$ and the base virtual period $T_{4B}$, method 300 determines the optimal excitation point E for the particular user.

Considering now FIG. 4, it illustrates the general steps of a method 400 using the DPAP device 10 of FIG. 1 that has been initialized according to method 300 of the present invention. At step 402, method 400 sets the base excitation parameters ($E_{OB}$, $T_{4B}$) of the excitation point E that were determined pursuant to method 300 of FIG. 3.

At step 404, the respiration sensor 126 (FIG. 1) monitors the approach of the excitation parameters ($E_0$, $T_4$) of the excitation point E to their respective base values ($E_{OB}$, $T_{4B}$). At step 406, as soon as the excitation parameters reach, or closely approach, their respective base values ($E_{OB}$, $T_{4B}$), method 400 inquires if any of the excitation parameters ($E_0$, $T_4$) of the excitation point E has significantly changed relative to its respective base value ($E_{OB}$, $T_{4B}$), i.e., within an acceptable range, for instance 1% to 15%.

If method 400 determines that any of the excitation parameters ($E_0$, $T_4$) of the excitation point E has not significantly changed relative to its respective base values ($E_{OB}$, $T_{4B}$), then method 400 proceeds to step 408. At step 408, method 400 applies the excitation at the excitation point E, in order to shorten the natural excitation stage.

If method 400 determines at step 406 that one or both of the excitation parameters ($E_0$, $T_4$) of the excitation point E has significantly changed relative to its respective base values ($E_{OB}$, $T_{4B}$), then method 400 proceeds to step 410. At step 410, method 400 automatically adjusts the unchanged parameter and thus adjusts the occurrence of the excitation point E. Method 400 then proceeds to step 408 and applies the excitation at the excitation point E, in order to shorten the natural excitation stage.

It is to be understood that the specific embodiments of the invention that have been described are merely illustrative of certain application of the principle of the present invention. Numerous modifications may be made to the description herein, without departing from the spirit and scope of the present invention. More specifically, while the present embodiments of the invention refer to an exemplary medical oxygen cylinder, it should be clear that the present respiratory gas delivery device may be used in conjunction (or be integrated) with other systems, such as: chemical oxygen generators, emergency oxygen systems provided for example, on submarines and airplanes, self-contained breathing apparatus (SCBA), diving breathing systems, breathing masks for firefighters, breathing masks during surgery, and in every situation or system that could benefit for the discontinuous gas delivery system described herein.

Figure 5:
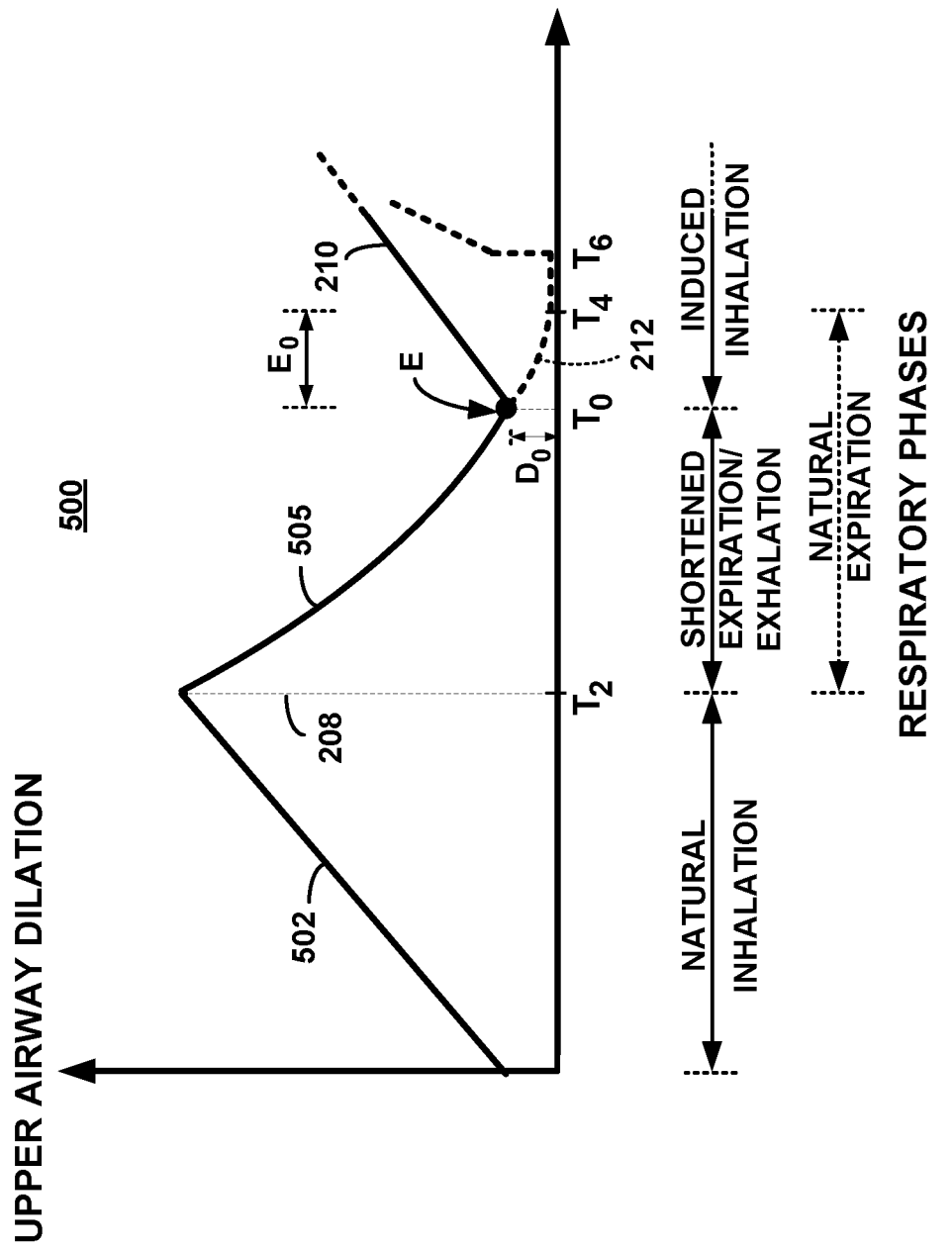
FIG. 5 is a graph that illustrates a simplified respiratory cycle, similar to that shown in FIG. 2, showing an exemplary virtual behavior, at $T_6$, when the brain signals the person who does not use the DPAP device, to wake up so that the muscles of the tongue and throat can increase the size of the airway.

FIG. 5 is a graph 500 that illustrates a simplified respiratory cycle, similar to that shown in FIG. 2, where the inhalation graph portion 502 replaces the graph sections 202, 204, and 206 (FIG. 2). Graph 500 illustrates an exemplary behavior, at time $T_6$, following the end of the expiration stage (at time $T_4$). At time $T_6$, the brain interprets the relatively flat line (shown in dotted line) of the graph 500, between $T_4$ and $T_6$, as the patient's inability to breathe, and signals the patient to wake up, so that the muscles of the tongue and throat can increase the size of the airway. The use of the DPAP device described herein introduces the stimulation, prior to time $T_4$ in order to induce a premature inhalation, thereby avoiding the brain induced event at $T_6$.

As stated earlier, the application of the excitation can be quantified as a measure of the dilation of the pharyngeal conduit 110. According to another embodiment of the present invention, the stimulation is applied when and if the sensor 126 identifies a breathing back pressure below a predetermined threshold, as the exhalation cycle approaches its virtual end at $T_4$.

According to still another embodiment of the present invention, the sensor 126 measures the rate of change of the exhalation graph, i.e., the derivative relative to time or instantaneous slope, of the exhalation graph portion 505. If, at any time, during the stimulation period $E_0$ the absolute value of the rate of change of the exhalation graph portion 505 is greater than a predetermined value for this particular patient, then a premature stimulation is introduced at E, in order to induce a premature inhalation. As a result, stimulation is delivery upon need, when necessary, in an attempt to anticipate and to prevent an apnea event.

Figure 6:
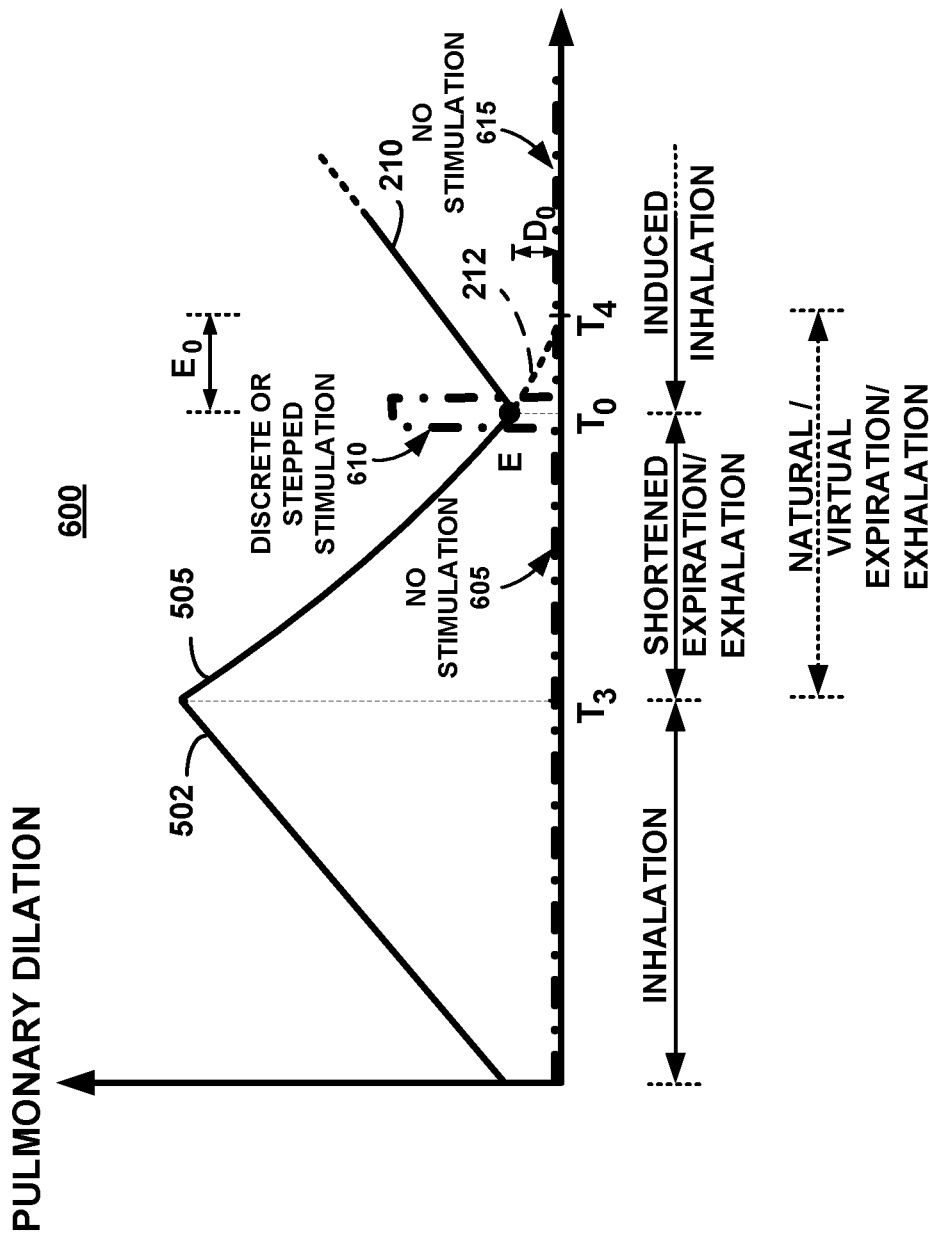
FIG. 6 is another graph that illustrates a simplified respiratory cycle, similar to that of FIG. 5, showing a discrete or stepped stimulation at the excitation point, E.

FIG. 6 is another graph 600 that illustrates a simplified respiratory cycle, similar to that of FIG. 5, showing the stimulation at the excitation point, E, or within the stimulation zone, $E_0$, as a discrete or stepped stimulation 610 that is preceded and succeeded by a lack of stimulation 605, 615, respectively, in order to induce a premature inhalation.

With reference to FIG. 7, FIG. 7A represents a graph 700 that illustrates a simplified respiratory cycle, similar to that of FIG. 5, showing a gradual (or soft) stimulation 705 during an extended stimulation period, $E_1$. The stimulation period, $E_1$, extends beyond the stimulation period $E_0$, so that the gradual stimulation 705 starts prematurely, at around time $T_7$, as shown, rather than around time $T_0$.

If after approximately a time period $E_2$, for example, at time $T_8$, either the natural or the induced inhalation cycle does not start (or is not induced), then the DPAP of the present invention has the following two alternative options:

The first option is for the DPAP to continue, at time $T_8$, the course of the gradual stimulation 705 until it reaches a sufficient stimulation level at time $T_0$ that corresponds to point E.

The second option is for the DPAP to apply, at a point F, that corresponds to time $T_8$, a discrete (or hard) stimulation 710 (shown in dotted line) that induces the premature inhalation 210 at approximately point E and that terminates at time $T_9$.

It should be noted that time $T_8$ may, but not necessarily, correspond to point F on the exhalation graph portion 505. In other terms, the gradual stimulation 705 in combination with the natural exhalation, are expected to induce a predetermined pulmonary (or pharyngeal) dilation at time $T_8$. If the latter dilation is not naturally attained at time $T_8$, then the stimulation is applied. Otherwise, neither the gradual stimulation 705 nor the discrete stimulation 710 is applied.

The advantage of this embodiment is that it minimizes the unnecessary application of stimulations, such as when the gradual stimulation 705 in combination with the patient's natural expiration induce an inhalation, prior to a safety time zone $E_4$. The safety time zone $E_4$ is defined as the difference between the extended stimulation period, $E_1$, and the sum of periods $E_1$ and $E_2$, as set forth in the following equation:

$$E_4 = E_1 - (E_2 + E_3),$$

Where $E_3$ represents the time period allocated to the application to either the gradual stimulation 705 or the discrete stimulation 710.

According to still another embodiment of the present invention, the soft stimulation or the hard stimulation following time $T_8$ are of different types. As an exemplary illustration only, the soft stimulation 705 prior to point F may be air, but the soft or hard stimulation following point F may be pure oxygen (or a different type of stimulation).

FIG. 7B illustrates another graph 725, wherein point F coincides approximately with point E, and the gradual stimulation 730 induces a premature inhalation, or the patient's natural inhalation is initiated on its own, then the stimulation 730 will no longer be allowed to unnecessarily increase, and will thus be interrupted.

This embodiment addresses the fact that current CPAP devices unnecessarily, continuously force air, and thus require continuous power even if the patient's own inhalation cycle starts naturally. As a result of the present reduction of power consumption during the inhalation stage and further during most of the exhalation stage, the power requirement to operate the present DPAP is significantly reduced, thus reducing the pump and battery sizes, rendering the DPAP amenable to being miniaturized, as it will be shown and explained herein.

Figure 7C:
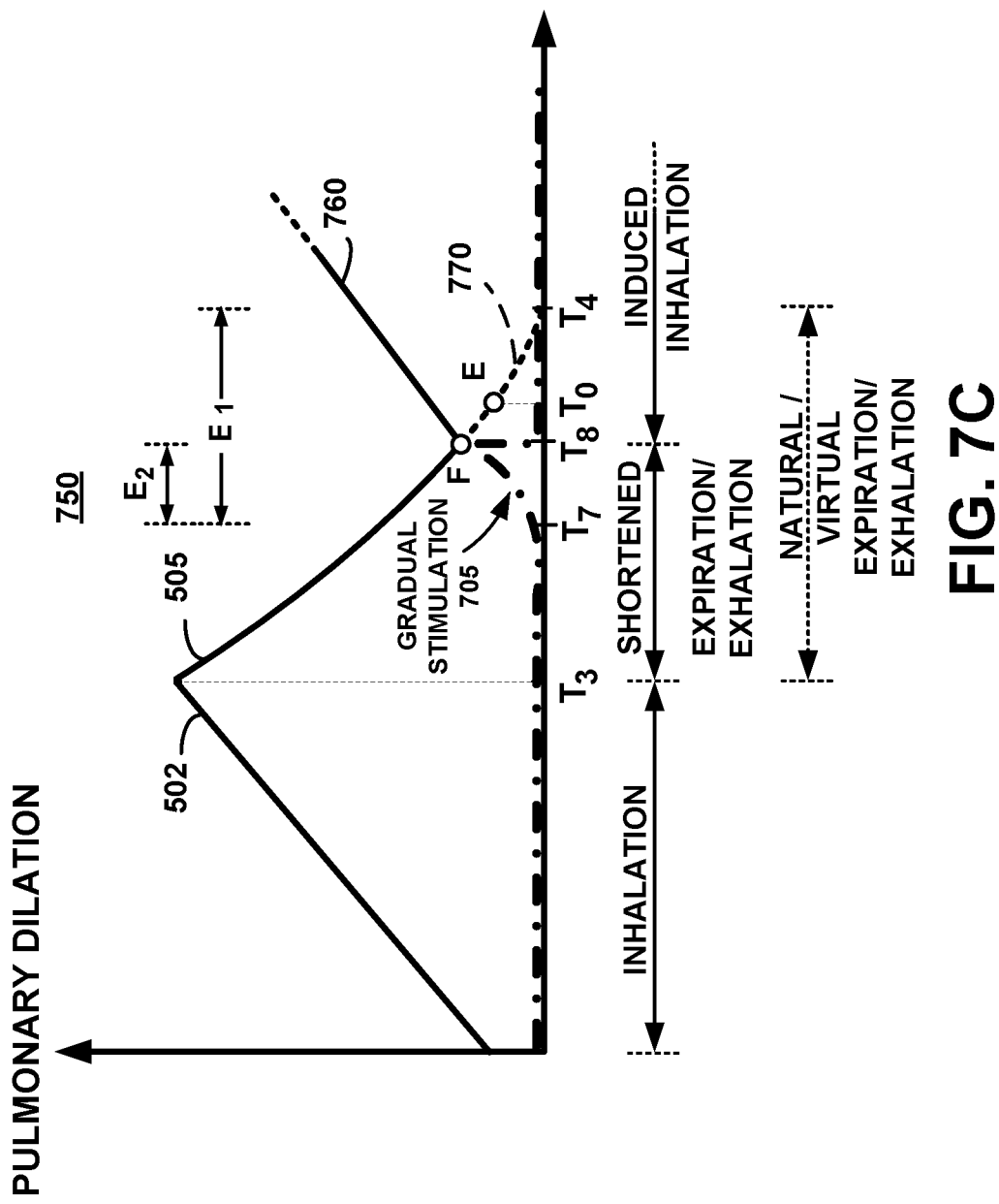
FIG. 7 is comprised of FIGS. 7A, 7B, and 7C, and illustrates three graphs of a simplified respiratory cycle, similar to that of FIG. 5, showing a gradual stimulation during the shortened expiration stage.

FIG. 7C illustrates yet another graph 750, that is similar to FIG. 7A, wherein the gradual stimulation 705 induces a premature inhalation, or the patient's natural inhalation 760 is initiated on its own, at or around point F (time $T_8$). In which event, the stimulation 705 will no longer be allowed to unnecessarily increase, and will thus be interrupted. The dashed line 770 illustrates the virtual pulmonary (or pharyngeal) dilation, had the inhalation 760 not taken place.

Figure 8:
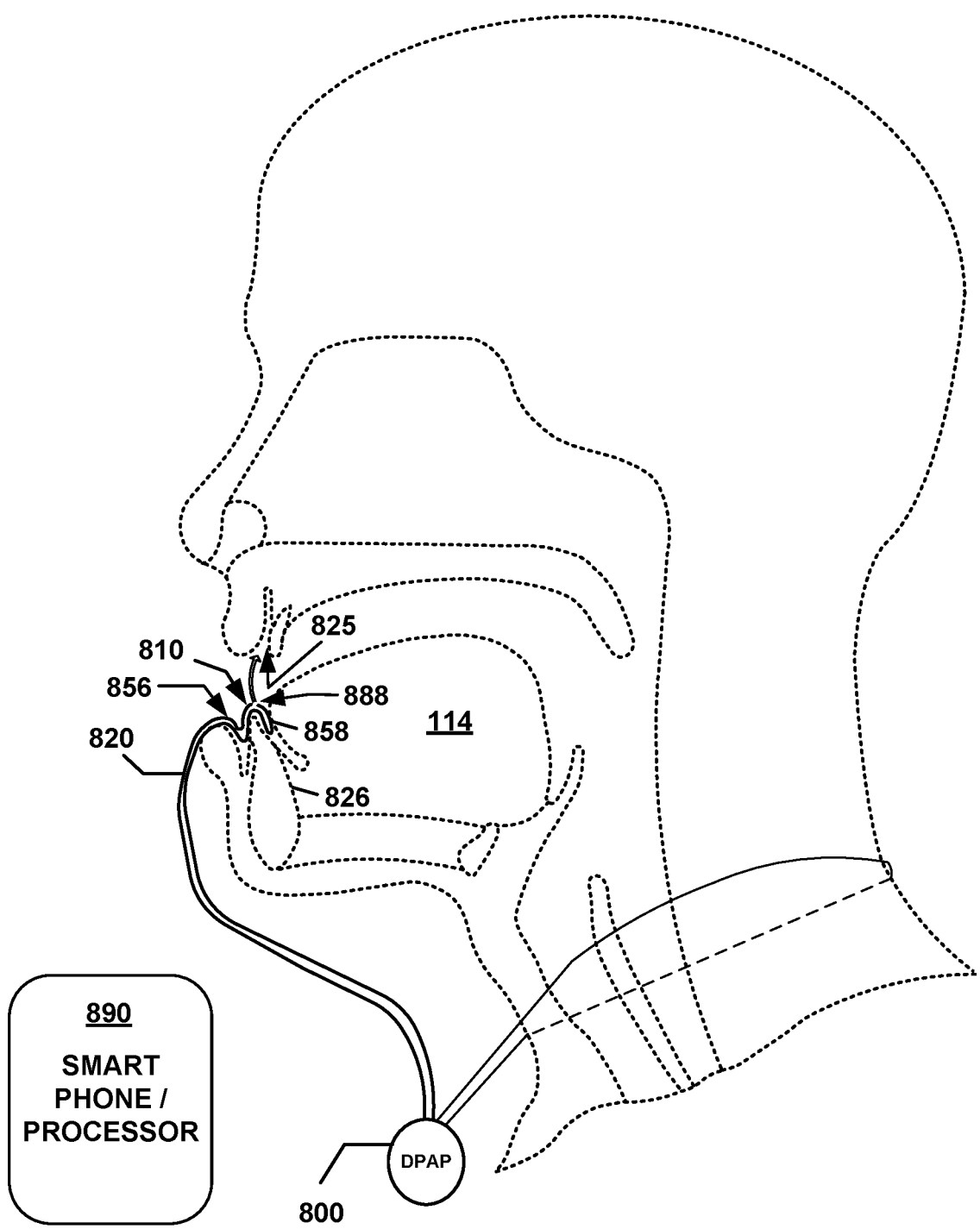
FIG. 8 illustrates another DPAP embodiment according to the present invention, that can be worn by a user, as a necklace, and that uses a dental appliance.

The significant reduction in the power requirement to operate the present DPAP device, enables the miniaturization of the DPAP device to such a size that enables it to be wearable or portable by the user, and not just simply transportable. One such DPAP 800 is illustrated in FIG. 8 that shows the DPAP 800 being worn by a user as a necklace or pendant.

According to a preferred embodiment, the DPAP 800 uses a dental appliance 810 that fluidly communicates with the DPAP 800 by means of an oral tube 820, which delivers the stimulation to the airways or more specifically, as shown in this embodiment, to the user's front mouth, upper gum or teeth 825 (FIG. 8), lower gum or teeth 826 (FIG. 9), or the underside of the tongue 114 (FIG. 9).

In a specific preferred embodiment where the dental appliance 810 is used in conjunction with the oral tube 820 for delivering the intake puff of gas, the dental appliance 810 may be made integrally with, and of the same material as the oral tube 820 for allowing the gas to pass therethrough. The dental appliance 810 includes a formable or compliant section 856 that fits over the user's teeth or gum 825, and an internal extension 858.

The dental appliance 810 includes an opening 888 that enables the stimulation, such as a gas puff, to be nozzled out of the dental applicant 810, directionally, toward the intended target stimulation area. In FIG. 8, the opening 888 is positioned so that the stimulation is directed toward the upper teeth or gum 825.

In this particular embodiment, the DPAP 800 is shown in communication with an external communication device 890, such as a smart phone and/or an external processor over a wireless communication channel, such as Blue Tooth, Wi-Fi, or another available or known wireless protocol. The external communication device 890 provides a variety of functions to the DPAP device 800, including but not limited to processing power for performing calculations, thus reducing the components that would have otherwise been added to the DPAP 800. This will reduce the power consumption of the DPAP 800 as well as its overall weight.

Figure 9A:
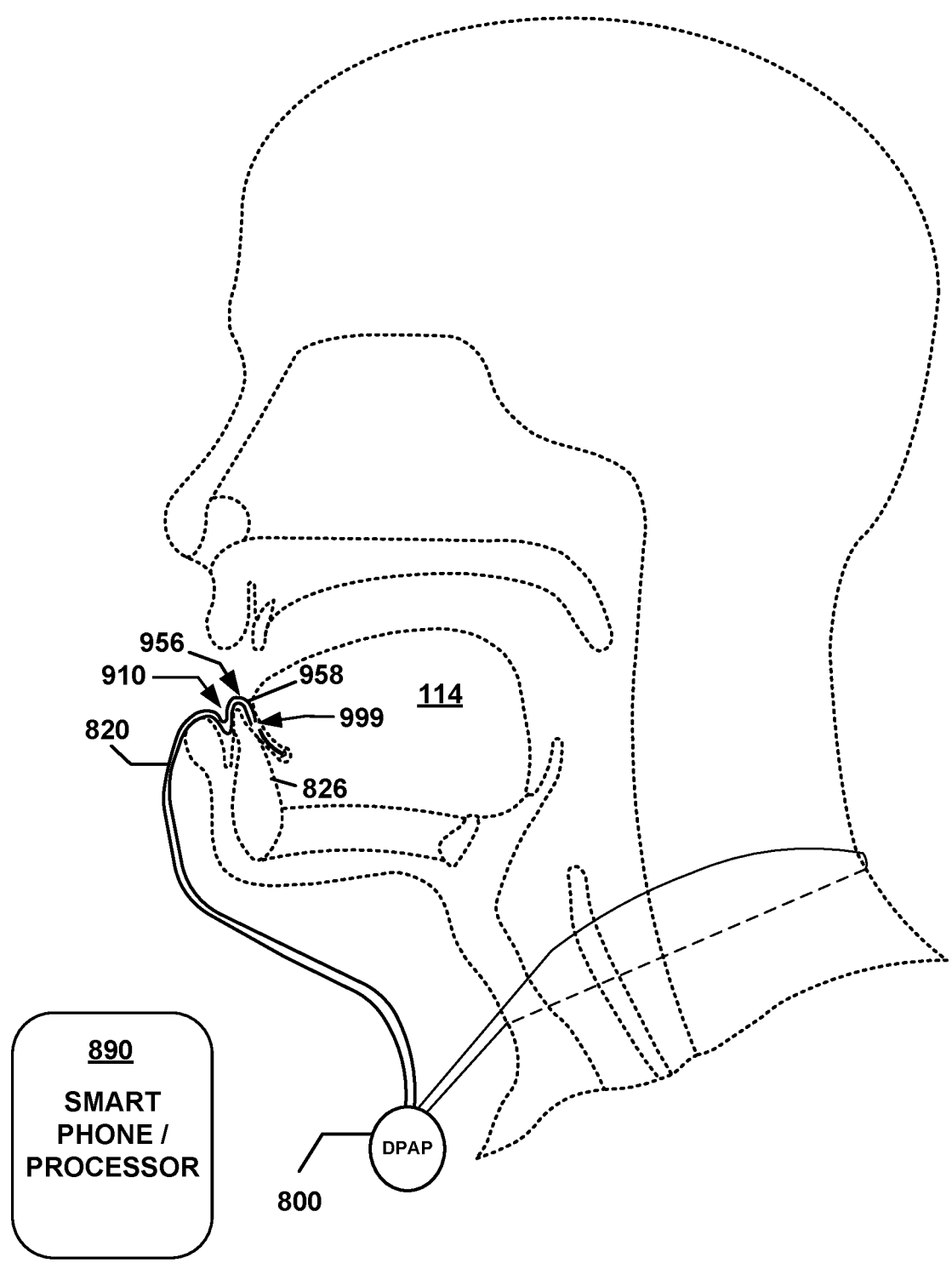
FIG. 9 is comprised of FIGS. 9A, 9B, and 9C, and illustrates the DPAP device of FIG. 8, in use with a variety of dental appliances.

In FIG. 9A, the opening 999 is positioned so that the stimulation is directed toward the lower teeth or gum 826 or the underside of the tongue 114. The dental appliance 910 is used in conjunction with the oral tube 820 for delivering the puff of gas (or stimulation). Similar to the dental appliance 810, the dental appliance 910 may be made integrally with, and of the same material as the oral tube 820 for allowing the gas to pass therethrough. The dental appliance 910 includes a formable or compliant section 956 that fits over the user's teeth or gum 826, and an internal extension 958.

The internal extension 958 includes an opening 999 that enables the stimulation to be nozzled out of the dental applicant 910, directionally, toward the intended target stimulation area, such as the lower teeth or gum 825 or the underside of the tongue 114.

According to yet another embodiment of the present invention, the internal extension 958 or the compliant section 956 may include a combination of nozzles that are positioned to selectively direct and distribute the stimulation to several target regions of the mouth.

Figure 9B:
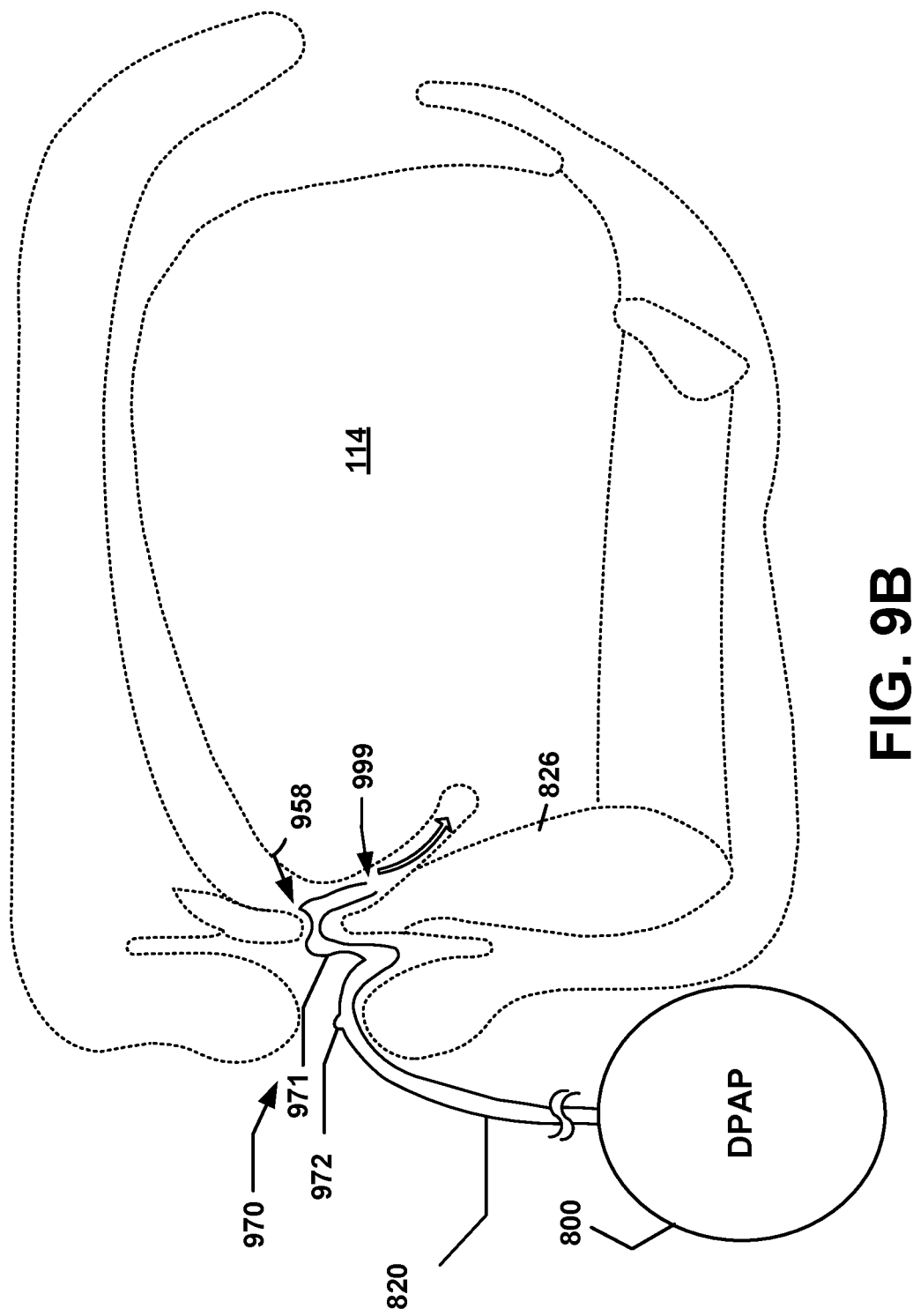
Figure 9C:
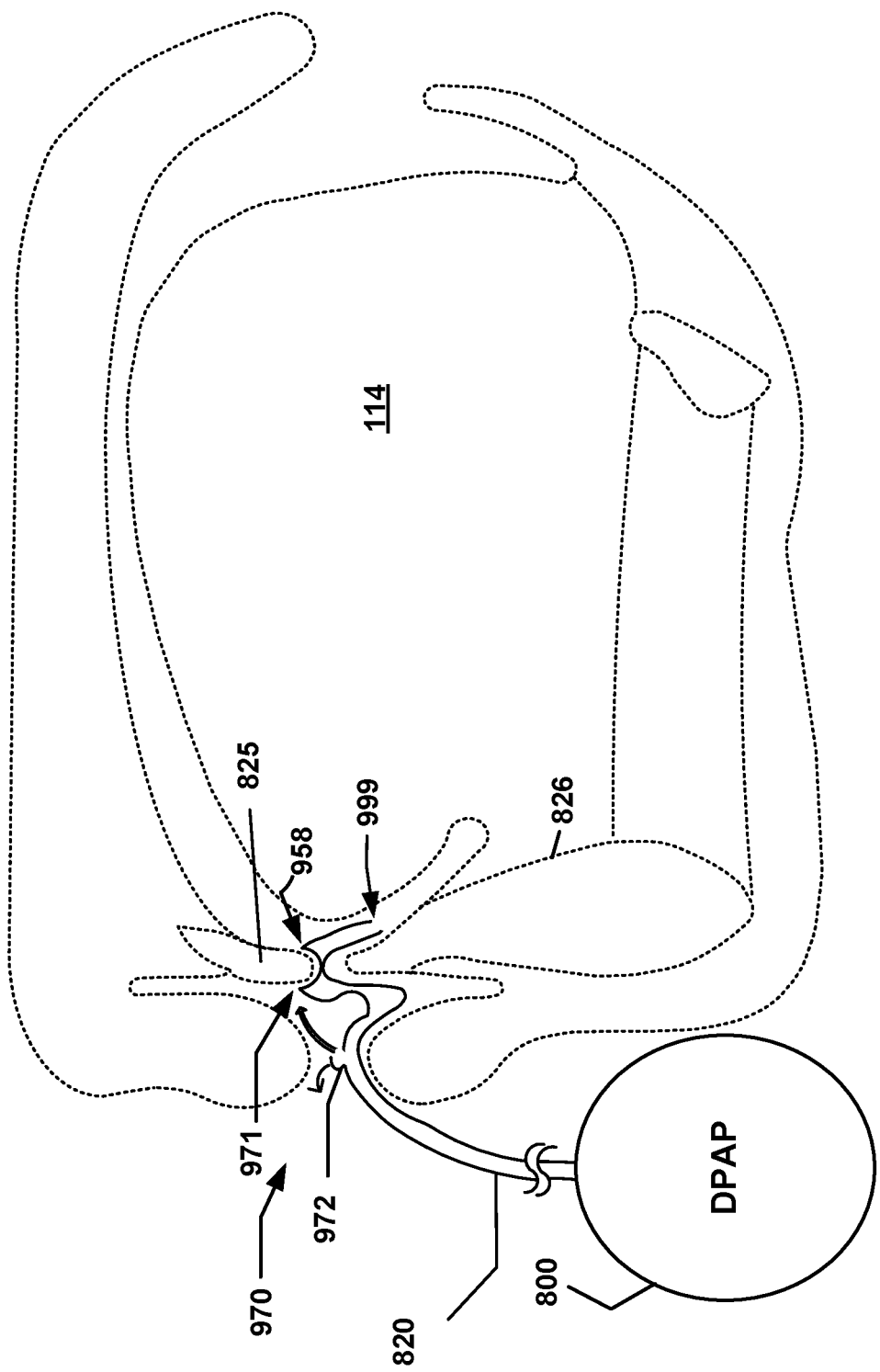

As further illustrated in FIGS. 9B, 9C, the dental appliance 970 presents an additional advantage to the user. The compliant section 971 of the dental appliance 970 includes two additional features. The first feature is a soft or pliable section 958 that fits between the upper and lower teeth 825, 826. During regular breathing events, the teeth 925, 926 slightly pressed against the pliable section 958 and deform it slightly so that it forms a resting seat for the teeth. During regular breathing events, the pliable section of seat 958 does not restrict the flow of fluid within the oral tube 820.

The dental appliance 970 maintains the upper and lower teeth 925, 926, slightly separated. The variation of the thickness of the dental appliance 970 may even provide some repositioning to the jaws to assist in maintaining the airway passages open.

The second feature of the dental appliance 970 is the valve 972 that is preferably positioned on the tube 820 or the compliant section 970. As long as the user does not grind the upper and lower teeth 825, 826, the valve 972 is normally closed, as shown in FIG. 9B.

However, with reference to FIG. 9C, since teeth grinding is believed to be associated with sleep disorder, when the user starts to grind his/her teeth 925, 926, then the grinding motion closes the pliable section of seat 958, and a back-pressure is built within the tube 820. This back pressure (or another feedback) causes the valve 972 to open and to direct the stimulation toward the teeth 825 and/826, as explained earlier. Once the grinding action stops, the flow through the nozzled opening 999 resumes and the valve 972 is closed.

It should be noted that the DPAP 800 can measure the back pressure resulting from the exhalation and from the closure of the pliable section 958, to determine the onset of the exhalation, the stimulation point E, and the delivery and timing of the stimulation.

Figure 10:
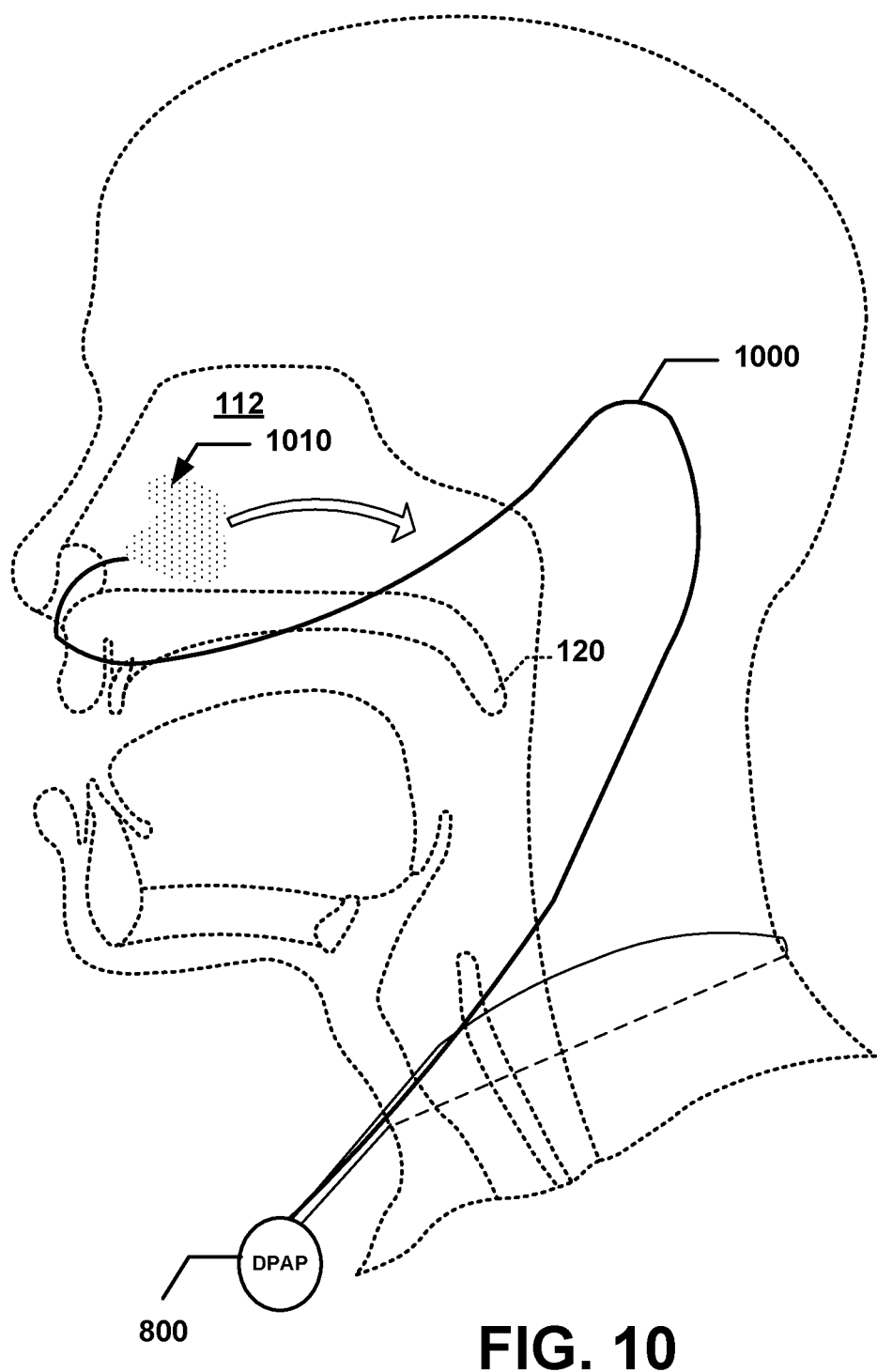
FIG. 10 illustrates the DPAP device of FIG. 8, in use with a nasal tube.

FIG. 10 illustrates the DPAP device 800 of FIG. 8, in use with a nasal tube 1000. The design and operation of the DPAP 800 enables its use with a simple nasal tube 1000 that is currently used in clinics and hospitals. Contrary to the conventional CPAP devices, the nasal tube 1000 does not restrict natural breathing. In other terms, if the DPAP 800 is turned off, the user will still be able to breathe. This is not typically the case with conventional CPAP devices. As a result, the DPAP 800 is a true assist device for breathing in that it selectively supplements natural breathing and does not regulate it completely.

The nasal tube 1000 is typically looped around the user's ears and delivers the stimulation to the nasal cavity 112. As the stimulation, such as a puff of gas enters the nasal cavity 112, it expands and may, in certain events, vaporize into particles 1010. These particles stimulate the user's olfactory senses and cause a reaction of the uvula 120, thus clearing the airways for breathing.

Figure 11:
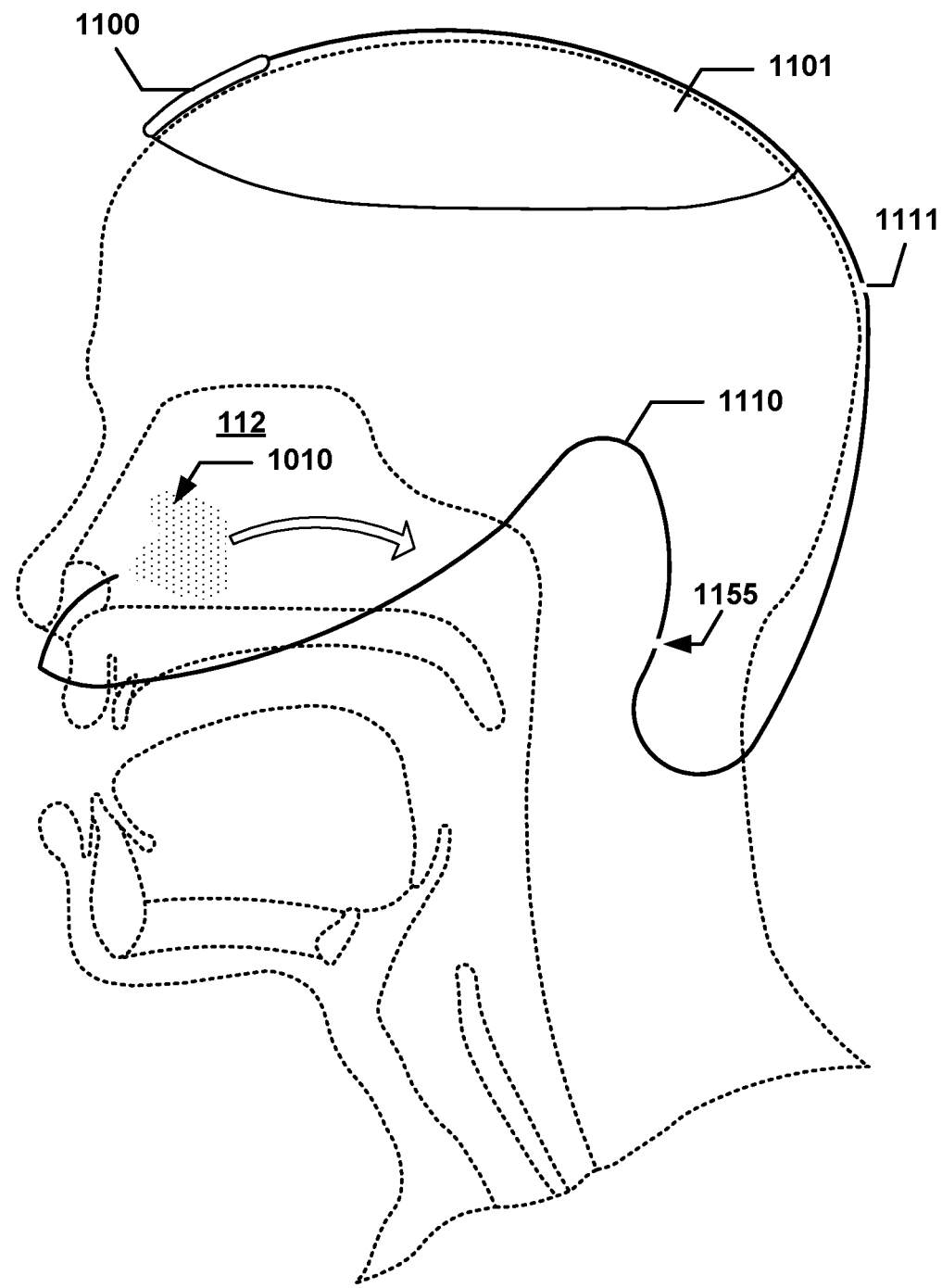
FIG. 11 illustrates the DPAP device of FIG. 8, that can be worn by the user, by means of a head gear.

FIG. 11 illustrates another way of donning the DPAP device 1100. The DPAP 1100 can be worn by the user, by means of a head gear or a strap 1101, and is connected to a nasal tube 1110, as explained earlier. The DPAP device 1100 and the tube 1110 do not interfere with the user's sleep positions, contrary to the conventional tubes that connect the conventional masks to the CPAP devices.

According to another embodiment of the present invention, it would be possible to incite the desired breathing response of a user, by stimulating, for example, the user's ear, the top of the head, or the scalp. The stimulation can be done by means of one or a plurality of holes, openings, or nozzles 1111, along the nasal tube 1110, in order to allow at least some of the stimulation to escape and stimulate the target area or areas.

According to another embodiment, one such opening 1155 is positioned in close proximity to the user's ear or ears, to generate an auditory stimulation, such as a high frequency pitch that causes the desired respiratory response. It would also be possible to pre-train the patient's automatic response to the auditory stimulation, to facilitate the desired response.

Figure 12:
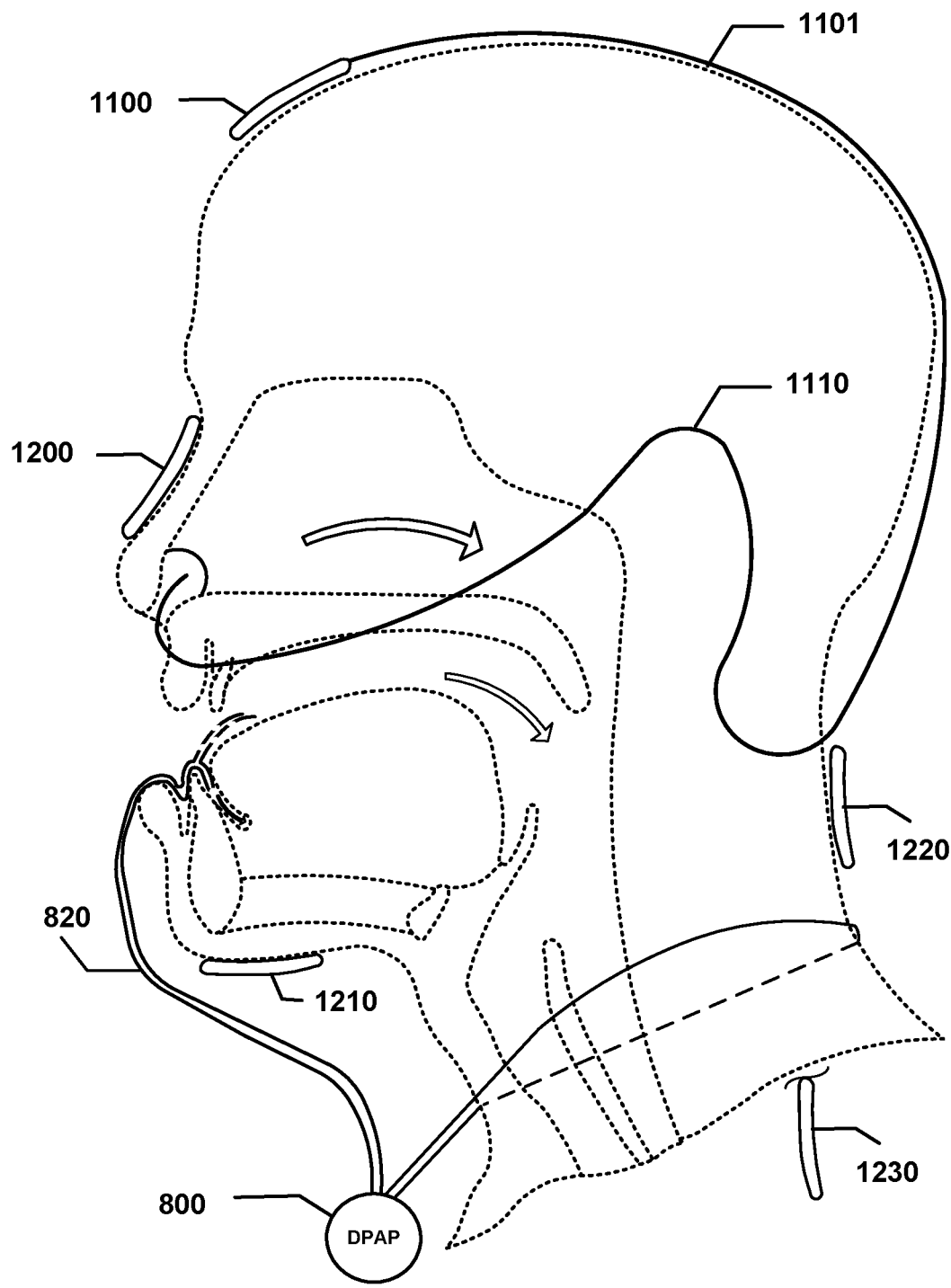
FIG. 12 illustrates a plurality of DPAP devices of FIG. 8, that can be selectively worn by the user.

FIG. 12 illustrates a plurality of DPAP devices of 800, 1100, 1200, 1210, 1220, 1230, that can be selectively worn (one or more) by the user, to effect the desired stimulation at different target areas or sites of the body. While only six exemplary DPAP devices are illustrated herein, it should be clear that a different number of DPAP devices as well as their associated target stimulation areas may be selected to best achieve the desired result. For illustration, the DPAP device 1230 may be worn in proximity to the user's armpit (or another part of the user's body) to provoke a change in the user's posture.

Figure 13:
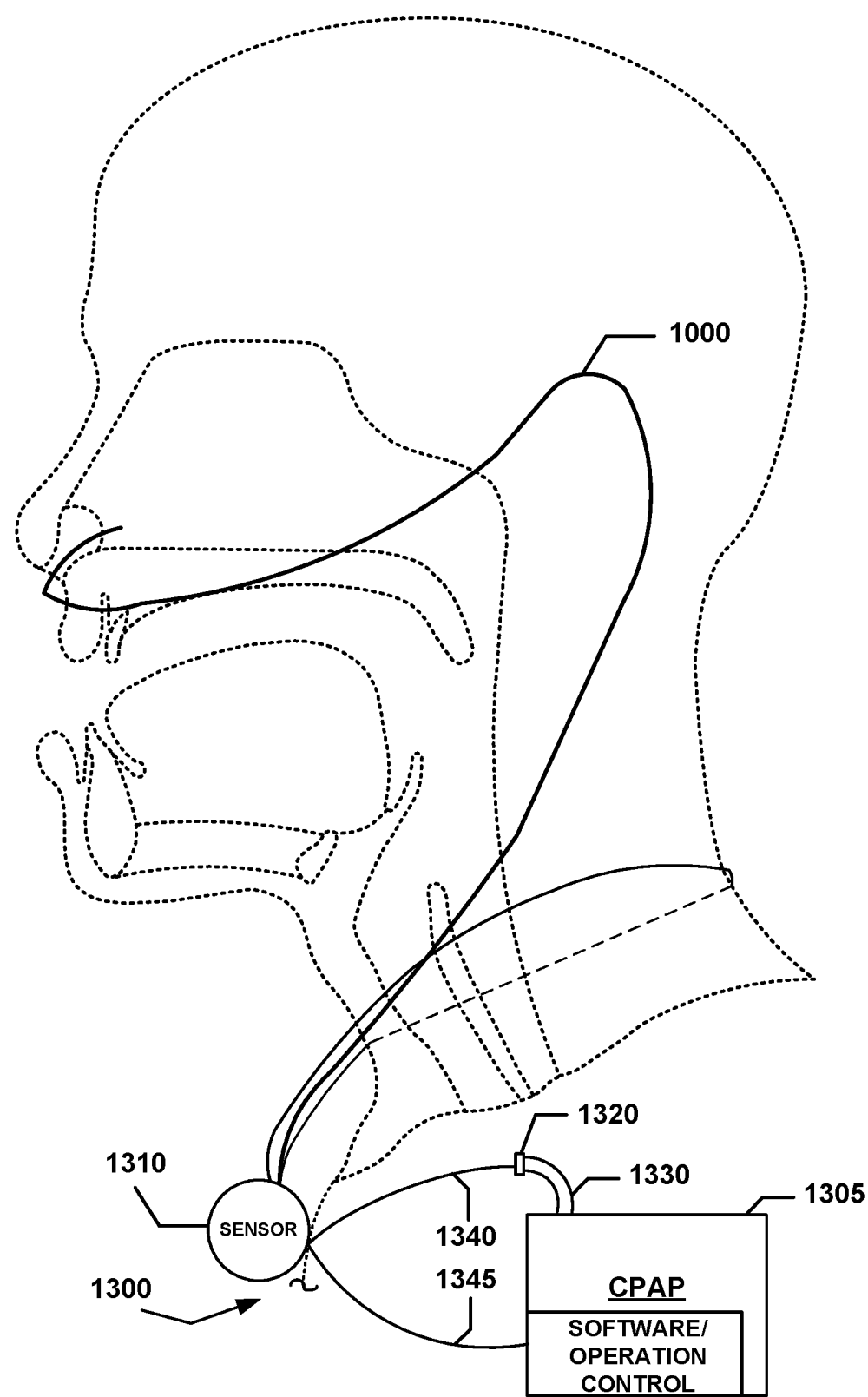
FIG. 13 illustrates another embodiment of the DPAP device according to the present invention, that can be used as a retrofit to an existing CPAP device.
Figure 14:
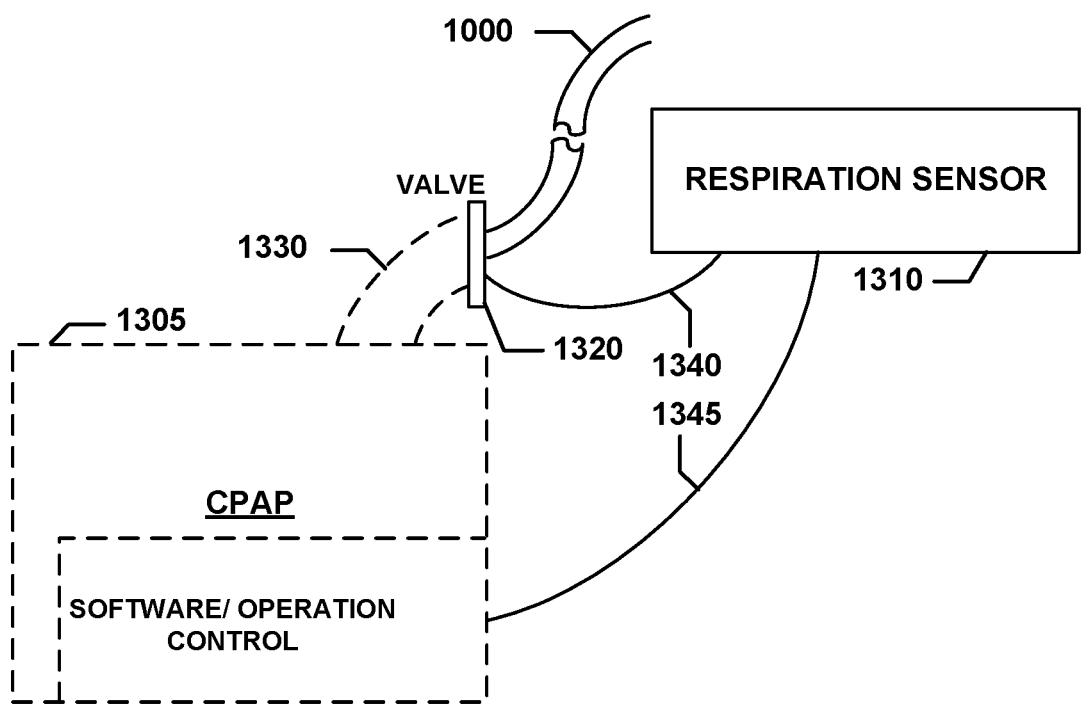
FIG. 14 is a block diagram of the DPAP device of FIG. 13, shown in use as a retrofit to the CPAP device.

FIGS. 13 and 14 illustrate another DPAP device 1300 according to an alternative embodiment of the present invention, which can be used as a retrofit to an existing CPAP device 1305. The operation of an exemplary conventional CPAP device 1305 can be regulated by a software application, with the continuous air being forced out of a hose 1330 that leads to a mask or some other respiration device.

The DPAP device 1300 makes use of the pumping force of the conventional CPAP device 1305. The DPAP device 1300 includes a respiration sensor 1310 that can be worn by the user like a necklace due to its miniaturized size, as explained earlier. The respiration sensor 1300 senses the onset of the exhalation stage and the approach of the stimulation point, E.

For example, the respiration sensor 1310 can measure the back pressure resulting from the user's exhalation (or the chest movement) to determine the onset of the exhalation stage and to monitor the exhalation stage, in order to determine (or to have the CPAP software determine) or calculate the optimal stimulation point, E.

To this end, the sensor 1310 is connected to the nasal tube 1000 and is also connected to a valve 1320 via a fluid tube 1340. The valve 1320 controls the flow of air from the CPAP device 1305 so that the DPAP device 1300 operates similarly to the DPAP 800, as explained earlier. The valve 1320 is connected at its other end, to the hose 1330. The valve 1320 can include a flow reducer that controls the rate of flow, the volume, and the pressure of the stimulation.

According to another design, the sensor 1310 is connected to the control circuitry of the CPAP device 1305 by means of wiring 1345 (or wirelessly by means of an interface). Alternatively, the operation of the CPAP device 1305 can be reprogrammed by the manufacturer (or a different authorized provider) to respond to the sensor 1310 and to operate the CPAP device 1305 according to the teachings of the present invention.

Figure 15A:
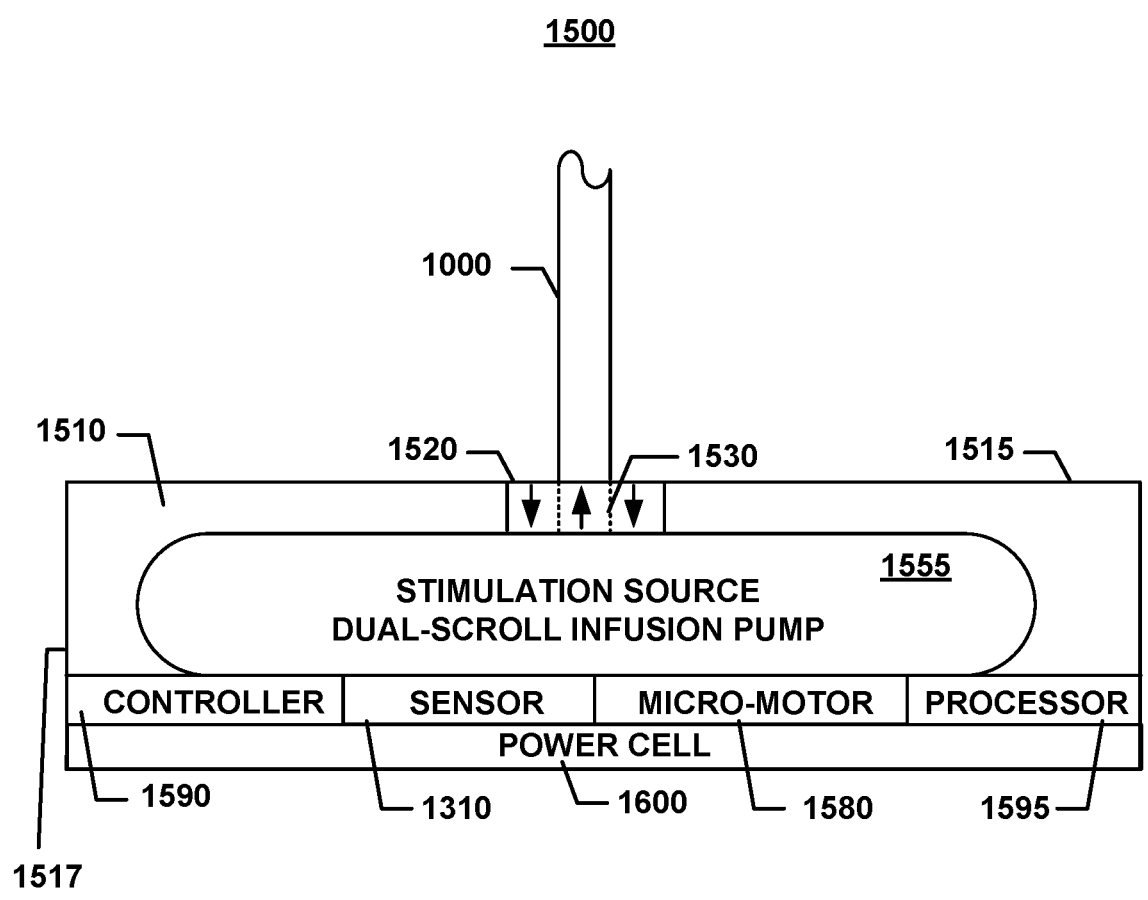
FIG. 15A is a block diagram architecture of a DPAP device according to a preferred embodiment of the present invention, shown using a dual-spiral infusion pump.

FIG. 15A is a block diagram architecture of a DPAP device 1500 (or of the DPAP device 800) according to a preferred embodiment of the present invention. The DPAP device 1500 generally includes a housing 1510 having a top side(or top cover) 1515. As used herein, the directional terms "top," "bottom," or other similar terms, are not intended to limit the use of the DPAP device e.g., 800, 1500 in a directional manner, but are rather used for illustration purposes, to facilitate the description of the present invention.

The DPAP device 1500 further includes an infusion pump 1555 with one or more inlet port 1520 and one or more outlet port 1530, that permit the exchange of fluid through the top side 1515. It should however be clear that while the inlet port 1520 and the outlet port 1530 are shown as being accessed from the top side 1515, other designs might be optimized by accessing the inlet port 1520 and the outlet port 1530 from the lateral side 1517 (or another side) of the housing 1510.

Figure 15B:
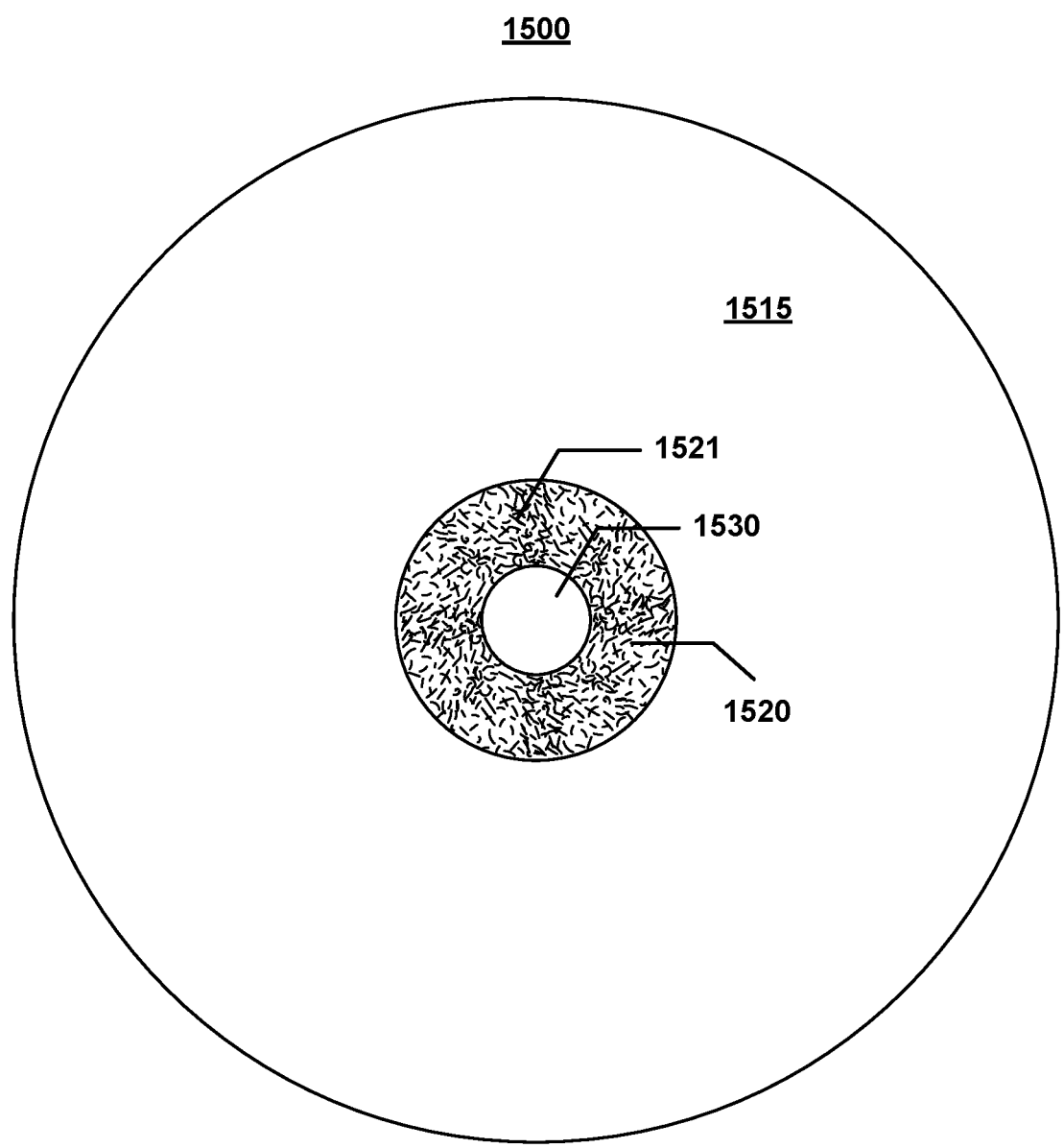
FIG. 15B is a top view of the DPAP device of FIG. 15A.

As further illustrated in FIG. 15B, the inlet port 1520 and the outlet port 1530 are concentric with a circular (or a different appropriate shape) cross-section. The inlet port 1520 may be covered by a filter 1521 that filters the incoming air or gas. The outlet port 1530 is connected to the nasal tube 1000.

In this particular embodiment, the infusion pump 1555 is the stimulation source that generates the stimulation, such as an air (a fluid, gas, or a combination of a gas and liquid) puff. The inlet port 1520 allows air (or gas) to be introduced into the infusion pump 1555, while the outlet port 1530 allows the pressurized air to be nozzled out of the infusion pump 1555 to provide the desired stimulation, as explained herein.

In one specific embodiment, the infusion pump 1555 is a dual-spiral infusion pump, as described in more detail in U.S. Pat. No. 5,578,077 to Kassatly. It should however be understood that different miniaturized pump may alternatively be used. The infusion pump 1555 is housed inside the housing 1510.

Another important feature of the DPAP device 1500 of the present invention, is the power cell 1600, which will be explained later in more detail. The power cell 1600 is preferably self rechargeable, and powers the various electrical and electronic components of the DPAP 1500, such as the respiration sensor 1310, a micro-motor 1580, a controller 1590, and a processor 1595.

The micro-motor 1580 is coupled to the infusion pump 1555 and causes its spiral-shaped scrolls to rotate. The controller 1590 regulates the flow of air and the delivery timing of the stimulation. The processor 1595 performs the necessary computations and is programmable. It should be understood that, in order to reduce the power consumption of the DPAP device 1500, the processor 1595 could be done externally or remotely, such as by means of a smart phone/processor 890 (FIG. 8).

Figure 16:
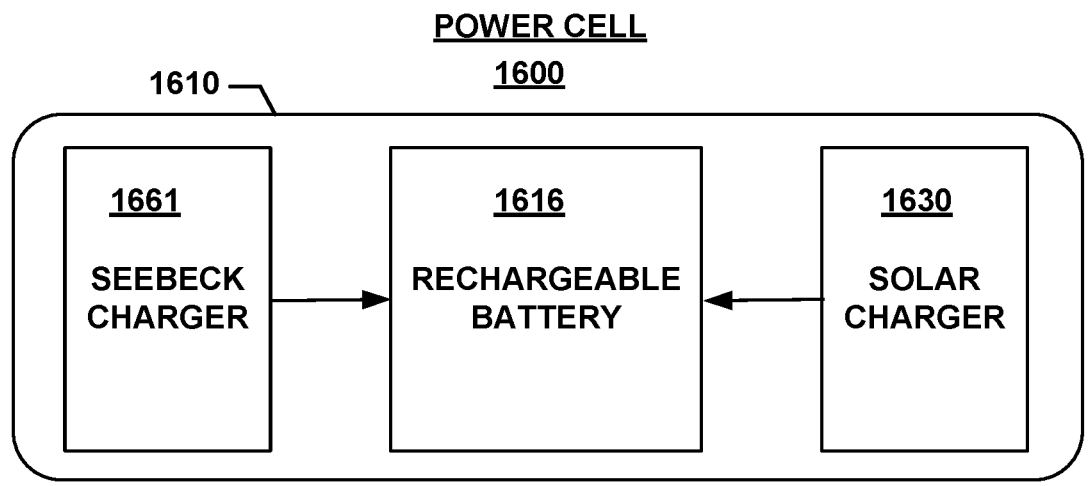
FIG. 16 is a block diagram of a power cell that forms part of the DPAP device of FIG. 15A.

FIG. 16 is a block diagram of the power cell 1600 that forms part of the DPAP device 1500 of FIG. 15A, according to a preferred embodiment of the present invention. The power cell 1600 generally includes a rechargeable battery 1616, of the type that is known or available. The rechargeable battery 1616 is automatically charged by one or more charging devices.

In the exemplary embodiment of FIG. 16, the rechargeable battery 1616 is shown as being charged by two charging devices, a Seebeck charger 1661 and a solar charger (or a light/photon charger) 1630. It should be understood that other chargers may alternatively be used, including but not limited to an external charger that charges the rechargeable battery 1616 directly.

In the embodiment illustrated in FIGS. 15A and 16, the micro-motor 1580 is preferably a thermoelectric micro-motor that is powered by the thermoelectric effect. The thermoelectric effect is also referred to as the Seebeck effect, and is used to generate electricity. Generally, the thermoelectric effect encompasses three separately identified effects: the Seebeck effect, the Peltier effect, and the Thomson effect.

In general, a thermoelectric device includes one or a series of p-type semiconductor elements and one or a series of n-type semiconductor elements that are electrically connected. When the two dissimilar elements are subjected to different temperatures, the Seebeck effect causes a voltage to be generated across the junctions between the p-type and n-type semiconductor elements.

The solar charger 1630 can further heat the Seebeck elements of the Seebeck charger 1661, to generate additional temperature differential that causes the Seebeck charger 1661 to generate electricity for charging the rechargeable battery 1616.

FIG. 15B shows the DPAP device 1500 as having a cylindrical shape with a circular top side 1515. This exemplary top side 1515 accommodates the inlet port 1520 and the outlet port 1530. The inlet port 1520 and the outlet port 1530 are concentric, but they can assume other positions and shapes. As illustrated in FIG. 15A, the outlet port 1530 is connected to the nasal tube 1000, while the inlet tube can preferably be capped with a filter 1521 that captures undesirable particles.

Figure 17:
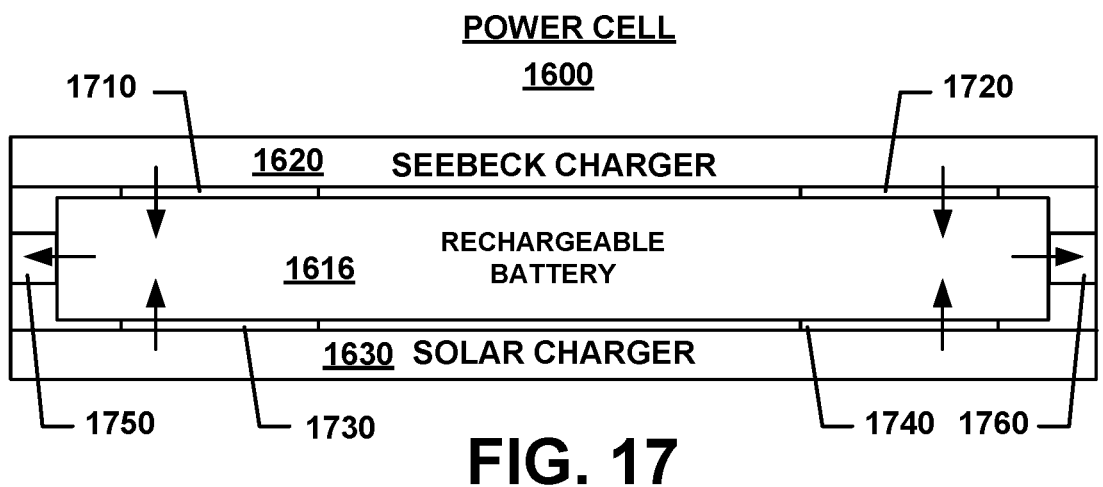
FIG. 17 is another block diagram of the power cell of FIG. 16, showing the layout of two different chargers and a rechargeable battery, wherein the power cell can be used as an accessory to the DPAP device of the present invention, or it can be used independently with a variety of other devices.

FIG. 17 is another block diagram of the power cell 1600 of FIG. 16, showing the layout of two different chargers 1620, 1630 and the rechargeable battery 1616. The power cell 1600 can be used as an accessory to the DPAP device 1500 of the present invention, or it can be used independently with a variety of other devices.

In this specific exemplary embodiment, the rechargeable battery 1616 of the power cell 1600 is placed centrally, and is electrically connected to the Seebeck charger 1620 by electrical contacts 1710, 1720. The rechargeable battery 1616 is also electrically connected to the solar charger 1630 by means of electrical contacts 1730, 1740. Additional electrical contacts, connect the rechargeable battery 1616 to other components of the DPAP device 1500, including but not limited to the controller 1590, the micro-motor 1580, and the processor 1595.

The power cell 1600 may be used independently of the DPAP devices of the present invention, and due to its miniaturized size and effectiveness, it can be used to power various electrical and electronic devices. As an example, the power cell 1600 can be miniaturized to power nano devices, whether or not they are implantable or introducible inside the body.

Figure 18:
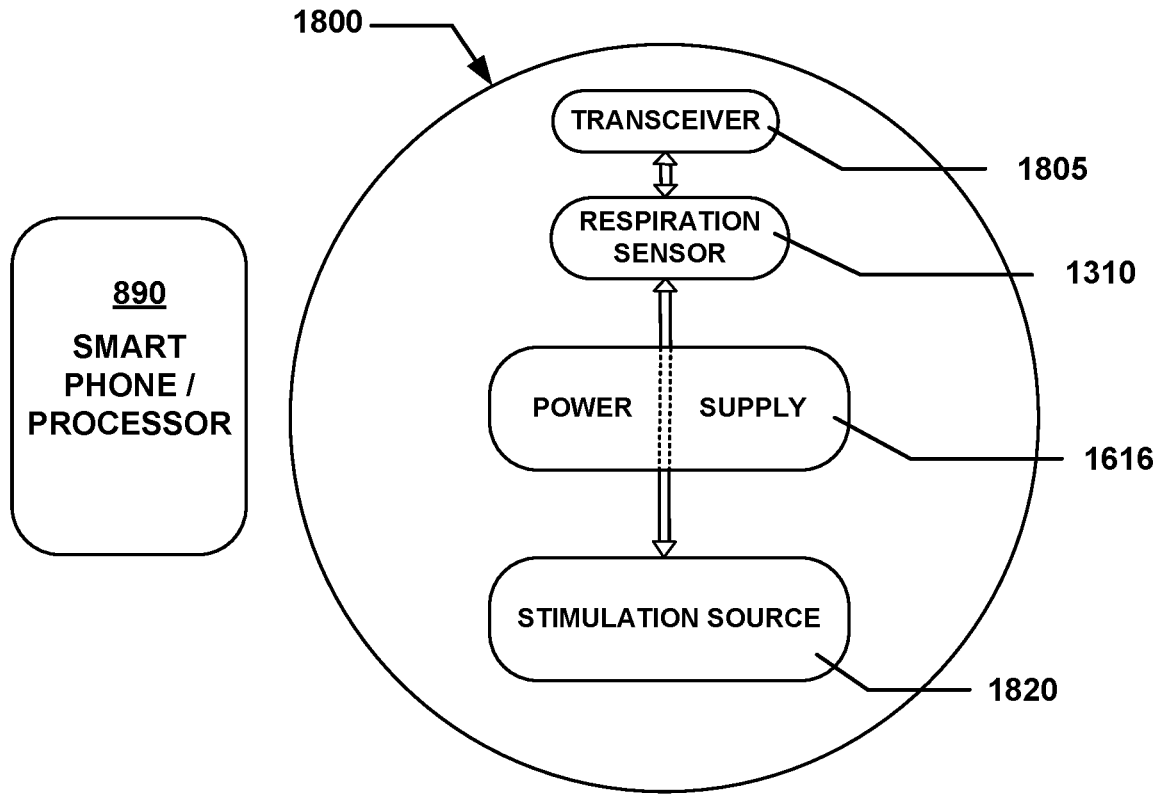
FIG. 18 is a high-level architecture of a DPAP device shown in use with a smart phone and/or an external processor, according to the present invention.

FIG. 18 illustrates a DPAP device 1800 in use with a smart phone and/or an external processor 890. To this end, the DPAP device 1800 includes the power supply 1616 that supplies the necessary power to a stimulation source 1820, a respiration sensor 1310, and a transceiver 1805.

Figure 19:
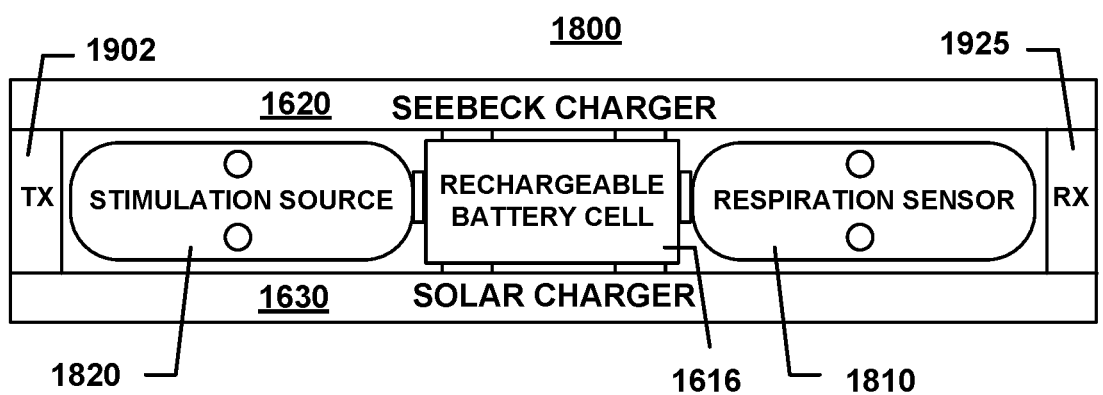
FIG. 19 is a more detailed architecture of the DPAP device of FIG. 14, illustrating two distinct power chargers.

As further illustrated in FIG. 19, the transceiver 1805 includes a transmitter 1902 and a receiver 1925. FIG. 19 further illustrates the stimulation source 1820 as including, for illustration purpose only, the Seebeck charger 1620 and the solar charger 1630.

In use, the DPAP device 1800 is worn by the user as a necklace, with the Seebeck charger 1620 in contact with the user's skin, whether with or without a electrolytic gel. The user's body temperature will raise and sustain the temperature of the Seebeck charger 1620 for generating charging power to the rechargeable battery 1616. The solar charger 1630 further supplements the charging of the rechargeable battery 1616.

When the DPAP device 1800 is not in use, it can be placed on a separate, external charging dock or station 2002, as it will now be described in connection with the DPAP device 2000 of FIG. 20.

Figure 20:
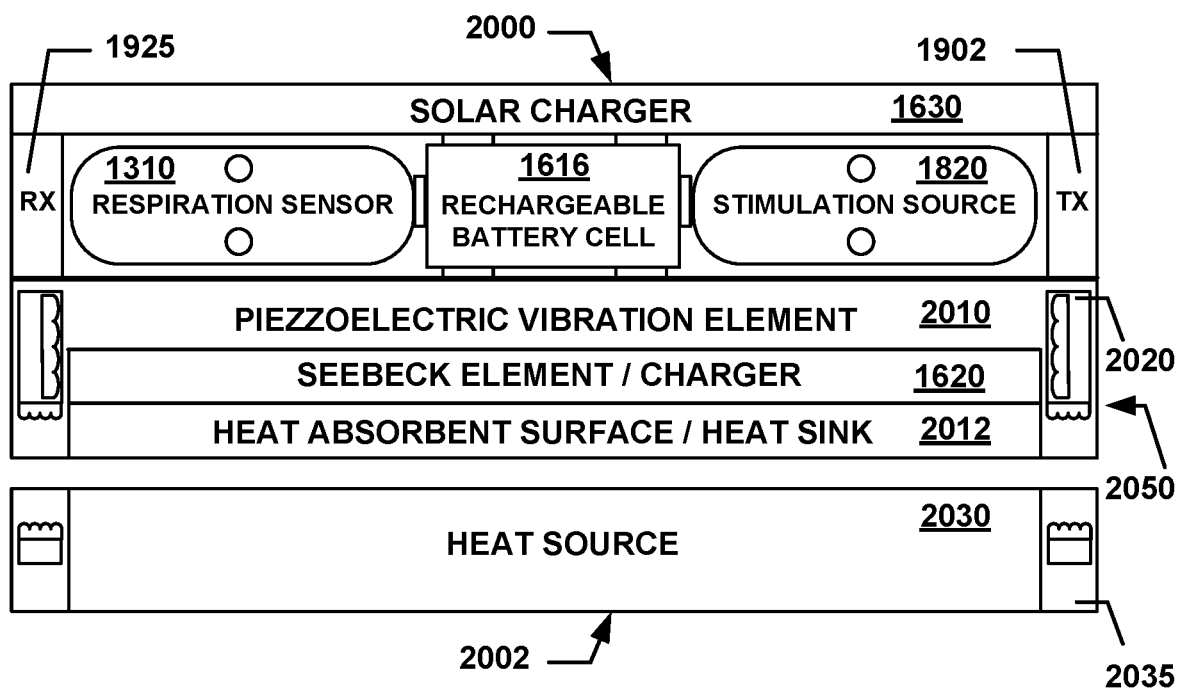
FIG. 20 is a block diagram of the DPAP of the present invention, which includes another embodiment of the power cell, shown docked on an external charging station.

FIG. 20 illustrates the DPAP device 2000 docked on the external charging station 2002. The external charging station 2002 may also be used with the DPAP device 1800 of FIGS. 18 and 19 and the other DPAP devices of the present invention.

The DPAP device 2000 is generally similar in function and design to the DPAP device 1800, but it further includes an additional charging element, namely the piezoelectric vibration element 2010. The piezoelectric vibration element 2010 converts the vibrations of the DPAP device 2000 into electrical current that further charges the rechargeable battery 1616. The vibration frequency of the piezoelectric vibration element 2010 can be set to a predetermined resonance frequency that maximizes the resonance, and thus maximizes the energy conversion from vibration to electrical (or vice versa as needed). As an example, the piezoelectric vibration element 2010 can be tuned to resonate at the user's heart rate, and therefore the piezoelectric vibration element 2010 becomes sensitive to, and captures the heart vibrations. In one embodiment, the piezoelectric vibration element 2010 can generate several milliwatts of power.

The DPAP device 2000 further includes a heat absorbent surface or heat sink 2012 that absorbs the heat from a heat source 2030 of the heat source 2002.

The DPAP device 2000 may further be provided with an inductive element 2020, that extends circumferentially, within and along the periphery of the DPAP device 2000. The inductive element 2020 inductively interacts with a similarly and generally oppositely situated inductive element 2035, to provide vibration to the piezoelectric vibration element 2010, heat to the Seebeck charger 1620, and wherein excess heat is absorbed by the heat absorbent surface 2012, thus minimizing energy loss.

In use, the DPAP device 2000 is placed atop the docking station 2002, such that the heat source 2030 faces the heat absorbent surface 2012, and the inductive element 2035 faces the inductive element 2020 of the DPAP device 2000. The docking station 2002 is generally cylindrically shaped with horizontal dimensions that substantially match those of the DPAP device 2000.

The piezoelectric vibration element 2010, the Seebeck element 1620, the heat absorbent surface 2012, the inductive element 202, and in certain designs, the solar charger 1630, are collectively referred to as power cell 2050.

Figure 21:
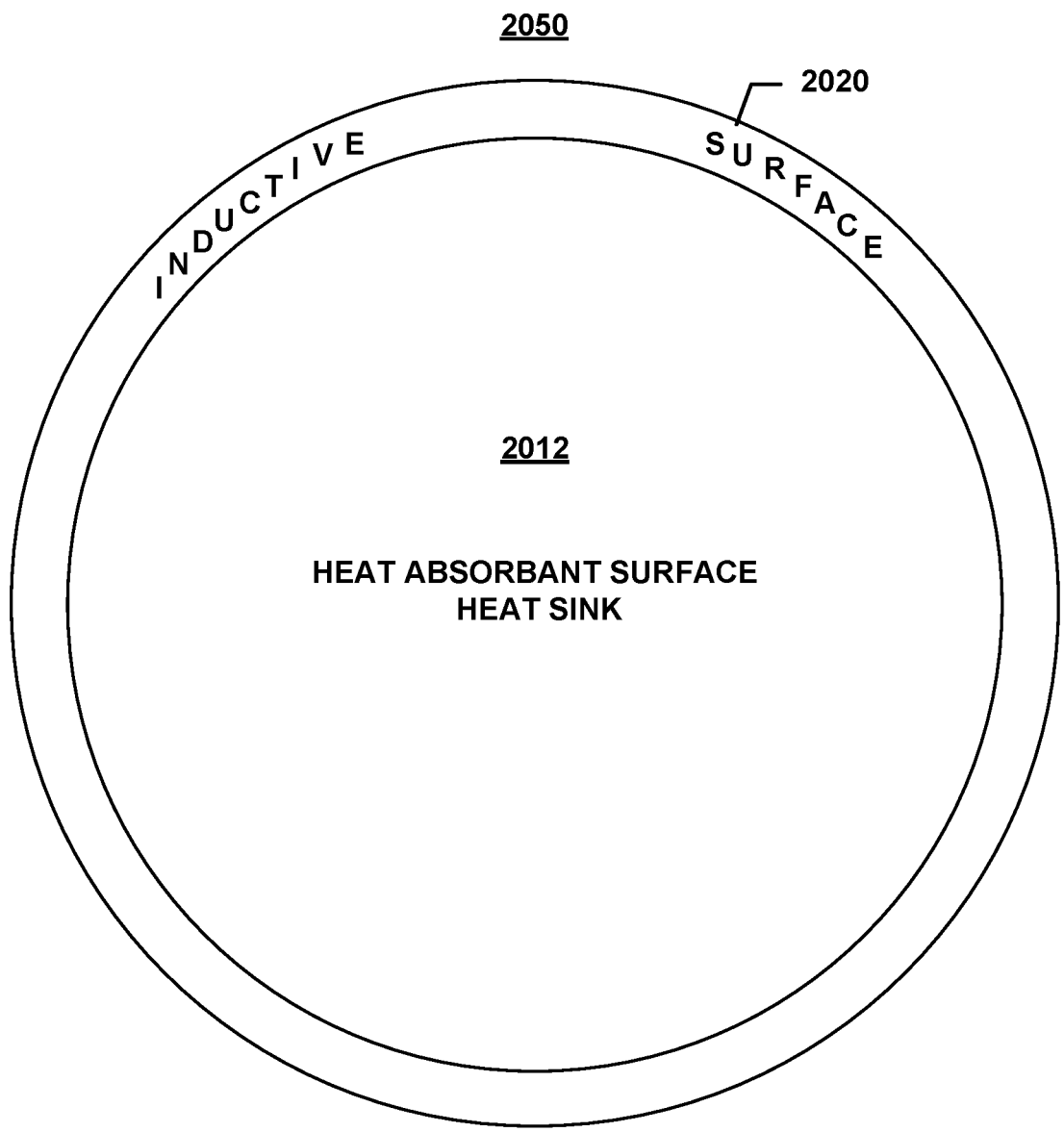
FIG. 21 is a bottom view of the power cell of the DPAP of FIG. 20.
Figure 22:
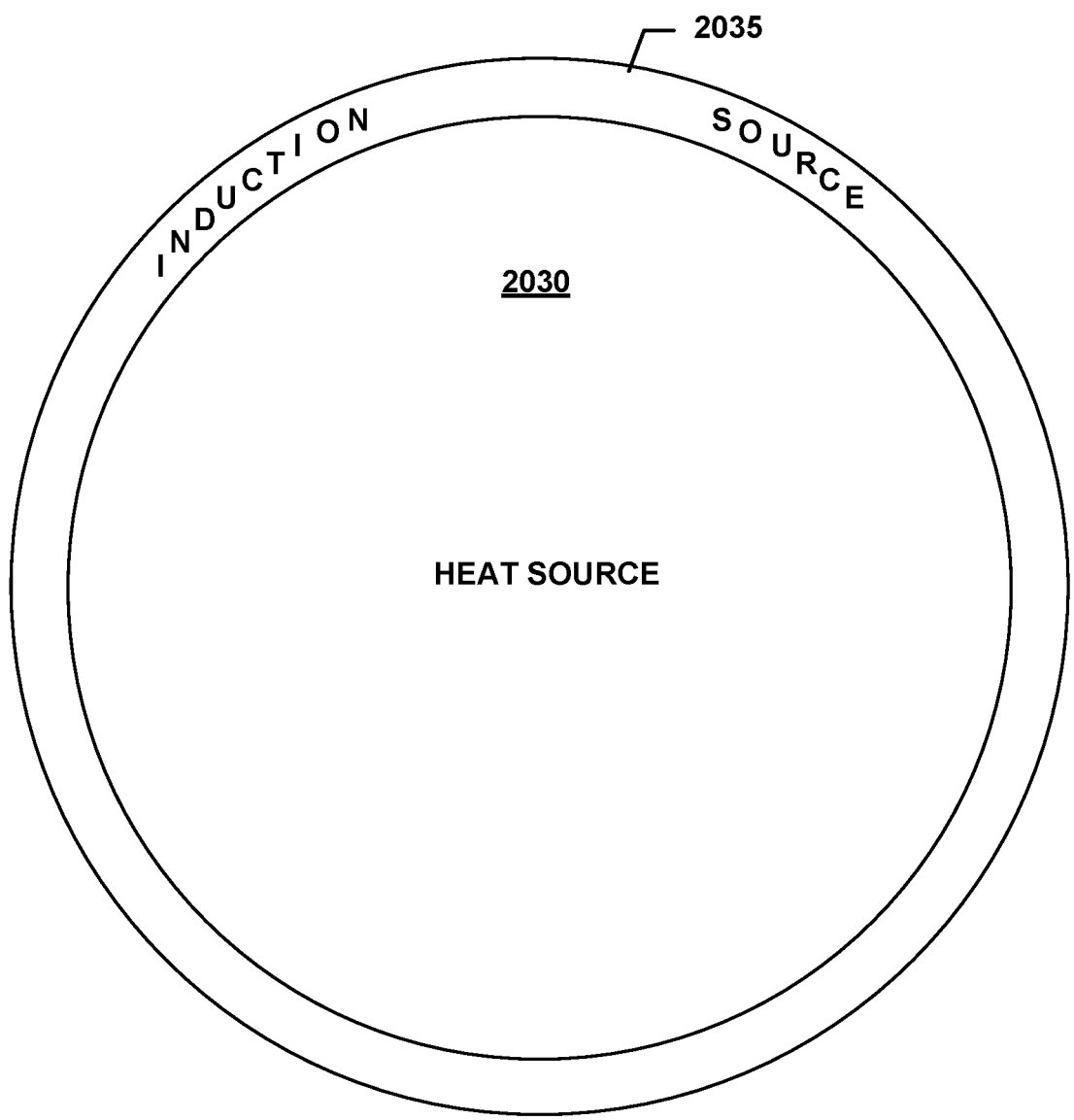
FIG. 22 is a top view of the external charging station of FIG. 20.

FIG. 21 is a bottom view of the power cell 2050 of the DPAP 2000 of FIG. 20. FIG. 22 is a top view of the external charging station 2002 of FIG. 20.

Figure 23:
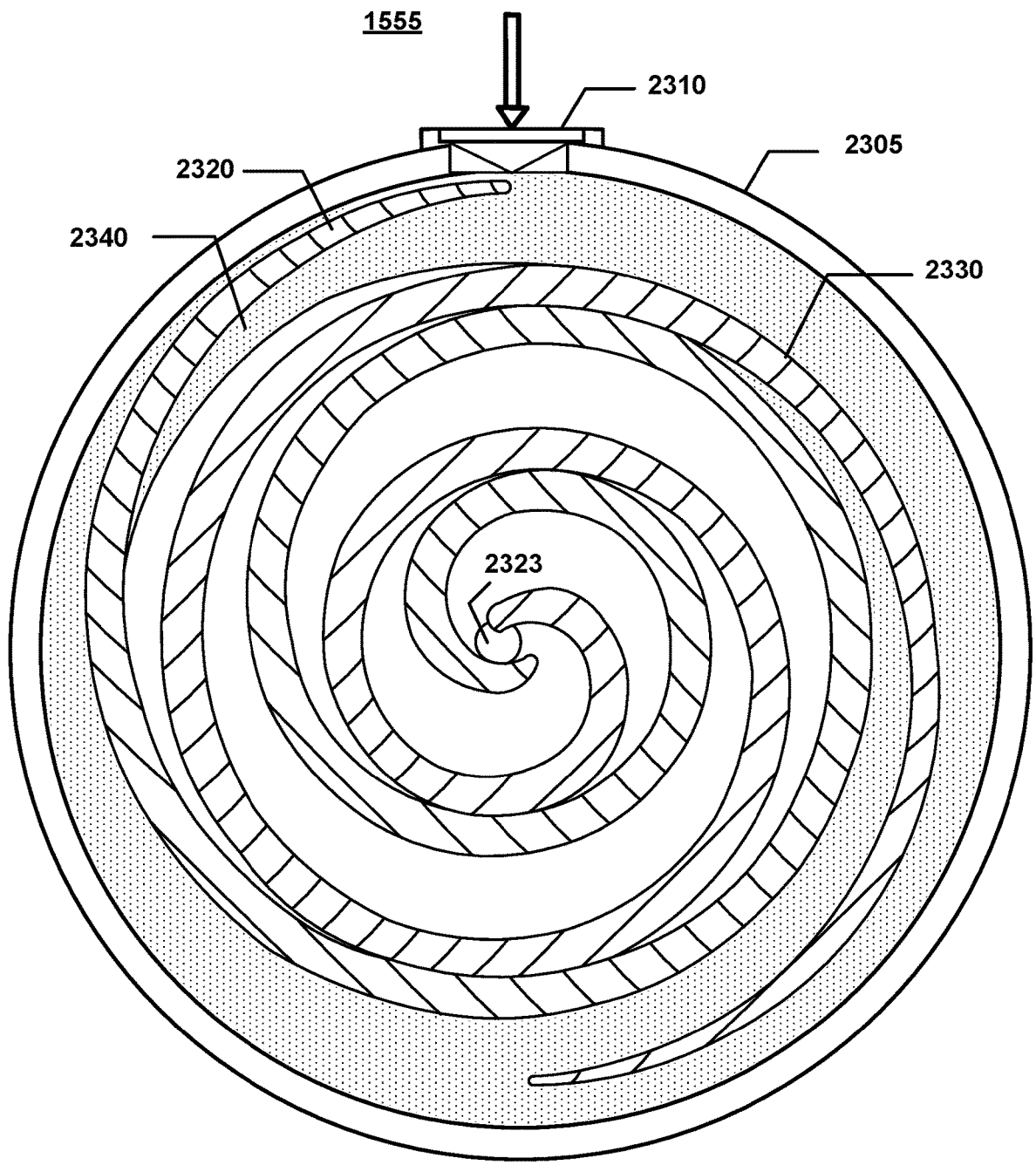
FIG. 23 is a cross-sectional view of the dual-spiral infusion pump of FIG. 15A, showing the air (or another gas) supply being pulled in between the two scrolls of the infusion pump.

FIG. 23 is a cross-sectional view of an exemplary stimulation device of FIG. 15A, which comprises a dual-spiral infusion pump 1555. The infusion pump 1555 intakes air (or another gas) supply through an intake port or valve 2310, inside a body 2305, through two scrolls 2320, 2330. As stated earlier, the operation of the dual-spiral infusion pump 2300 in compressing or expanding a fluid 2340 is explained in more detail in U.S. Pat. No. 5,578,077 to Kassatly, which is incorporated herein by reference in its entirety.

Figure 24:
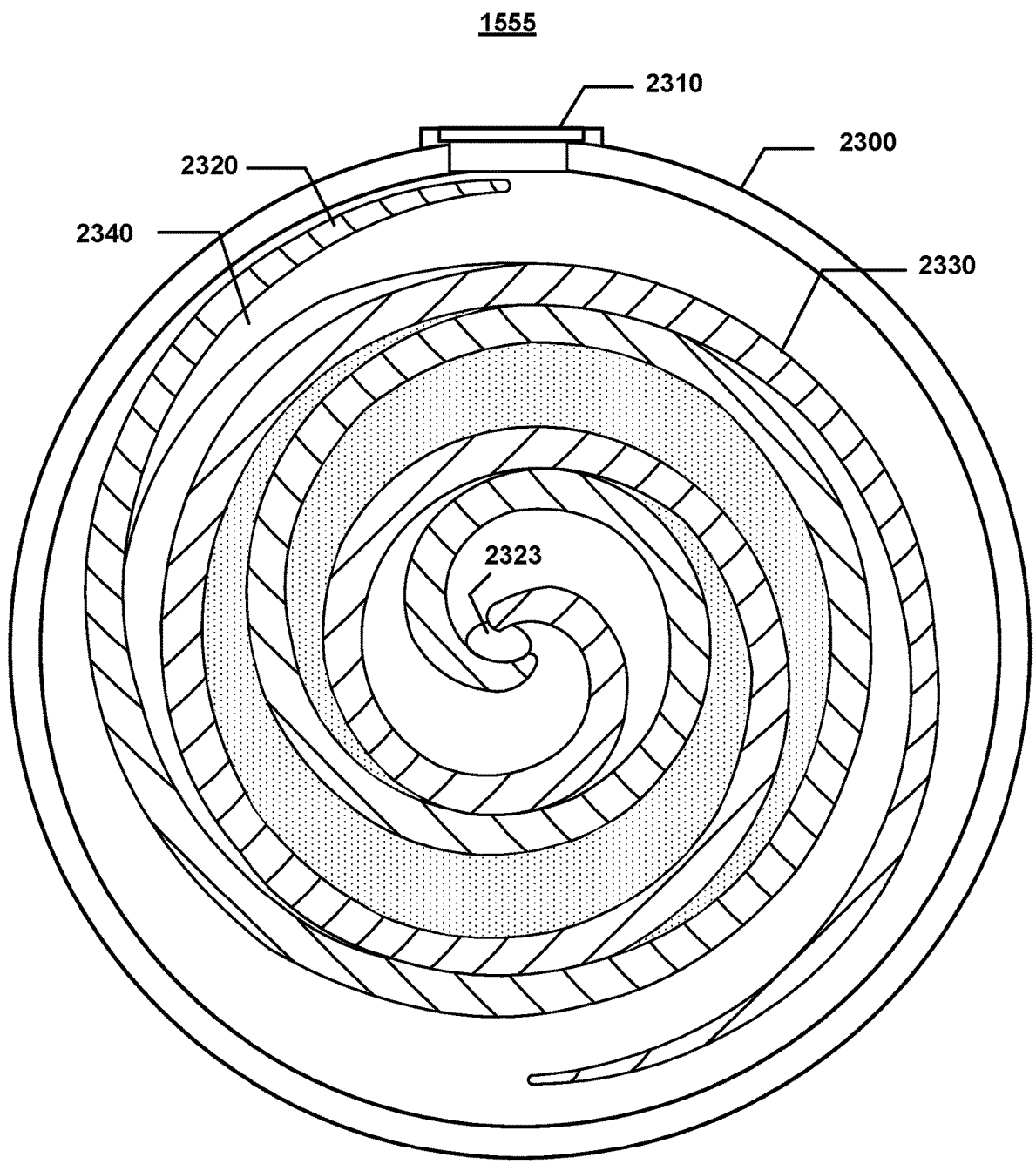
FIG. 24 is a cross-sectional view of the dual-spiral infusion pump of FIGS. 15 and 23, showing the air supply that has been previously introduced in FIG. 23 being compressed, in preparation for release as a stimulation (or excitation) at the excitation point, E.

FIG. 24 is another cross-sectional view of the dual-spiral infusion pump 1555 of FIG. 23, showing the air supply that has been previously introduced in FIG. 23 being compressed, in preparation for release as a stimulation (or excitation) at the excitation point, E, through an output port 2323. As shown in FIG. 15A, the output port 2323 is connected through port 1530, to the nasal tube 820.

Figure 25:
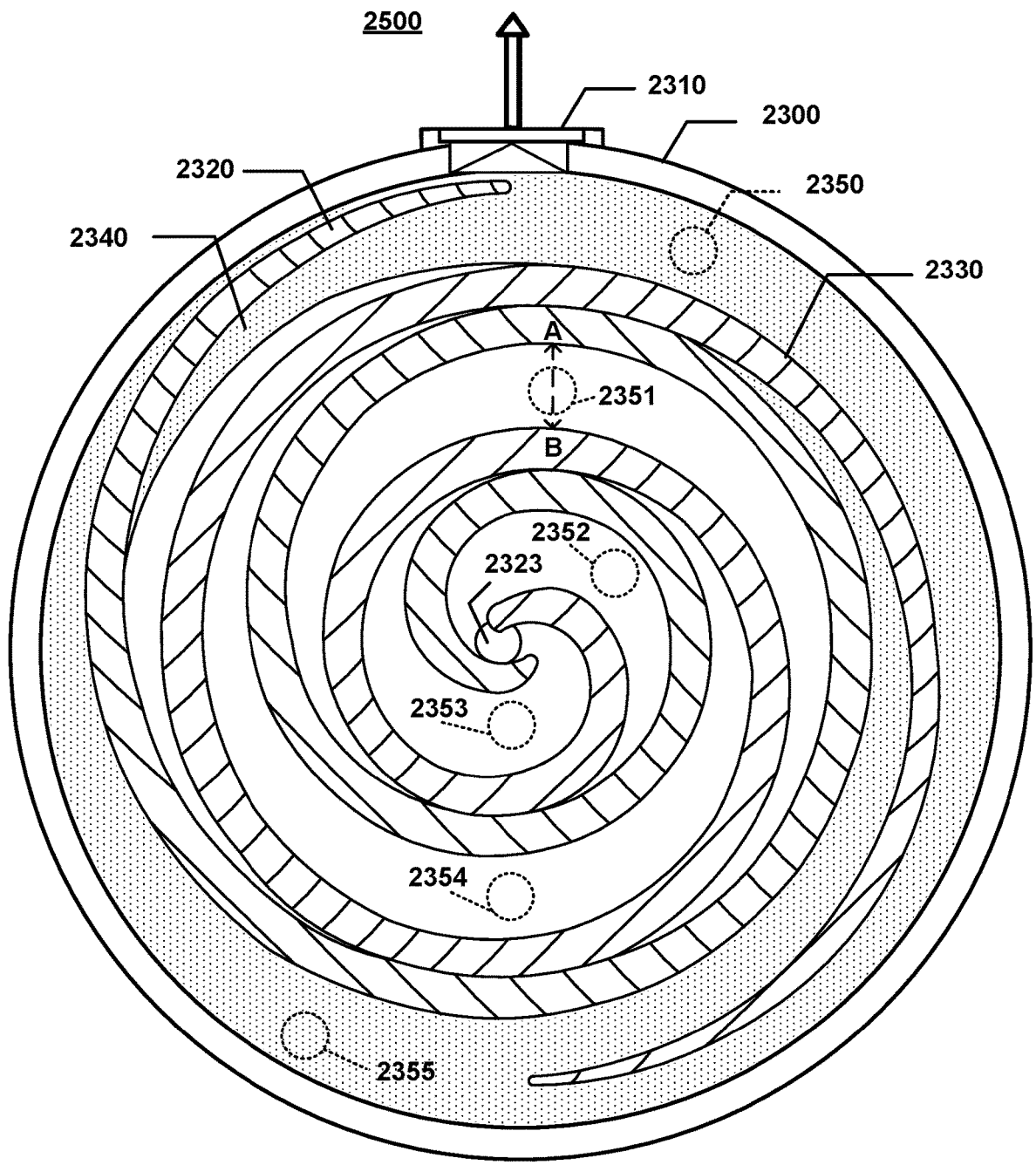
FIG. 25 is a cross-sectional view of an expansion pump comprising a plurality of exhaust ports or valves that allow the expanding fluid to be forced out of the expansion pump.

FIG. 25 is a cross-sectional view of an expansion pump 2500, having basically the same or similar components as those of the dual-spiral infusion pump 1555 of FIGS. 23 and 24, and further comprising a plurality of exhaust ports or valves 2350, 2351, 2352, 2353, 2354, 2355 that are distributed at predetermined locations so as to allow the expanding fluid 2340 to be forced out of the expansion pump 2500.

To this end, the fluid 2340 is inputted through the port 2323, and the relative motion of the scrolls 2320, 2330 is the reverse of that of the corresponding scrolls 2320, 2330 of the spiral infusion pump 1555 of FIGS. 23 and 24. Alternatively, the exhaust ports 2350, 2351, 2352, 2353, 2354, 2355 are omitted and the fluid 2340 is allowed to exhaust through the port or valve 2310. While only six exhaust ports 2350, 2351, 2352, 2353, 2354, 2355 are illustrated, it should be clear that a different number of exhaust ports may be selected.

In one embodiment, the positioning of the exhaust ports 2350, 2351, 2352, 2353, 2354, 2355 is such that they are located at the maximal distance between the two scrolls 2320, 2330, as shown by the double arrow "AB" relative to the exhaust port 2351.

Figure 26:
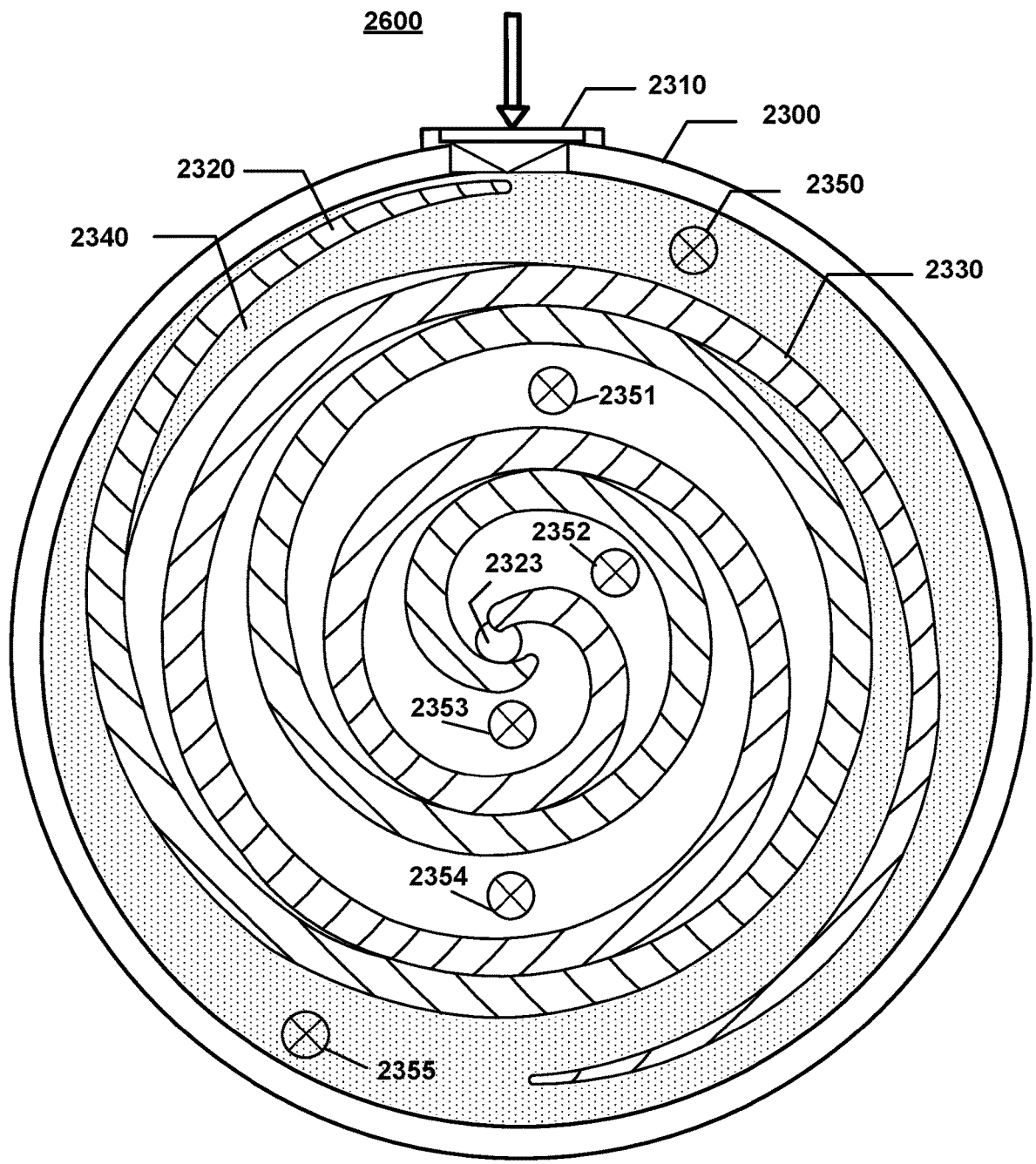
FIG. 26 is a cross-sectional view of a dual function infusion/expansion pump having basically the combined function of the dual-spiral infusion pump of FIGS. 23 and 24, and that of the expansion pump 2500 of FIG. 25, for use as a breathing assist device.

FIG. 26 is a cross-sectional view of a dual function infusion/expansion pump 2600, having basically the combined function of the dual-spiral infusion pump 1555 of FIGS. 23 and 24, and the expansion pump 2500 of FIG. 25, for use as a breathing assist device, including its use as a CPAP device, a DPAP device, a breathing apparatus for diving.

In operation, during the inhalation stage 502 of the respiratory cycle of FIG. 5, the pump 2600 intakes air, oxygen, or another breathing gas 2340 through the port 2310 and compresses the gas 2340 for exhaust through the port 2323, as explained earlier. During the inhalation stage 502, the exhaust ports 2350, 2351, 2352, 2353, 2354, 2355 are closed to prevent the escape of the gas and to ensure increase pressure.

During the expiration stage 505, the exhaled carbon dioxide is pulled into the pump 2600 through the port 2323, and expanded to exhaust through the exhaust ports 2350, 2351, 2352, 2353, 2354, 2355, with the port 2310 being closed, to ensure that the carbon dioxide is not breathed in by the user.

Figure 27:
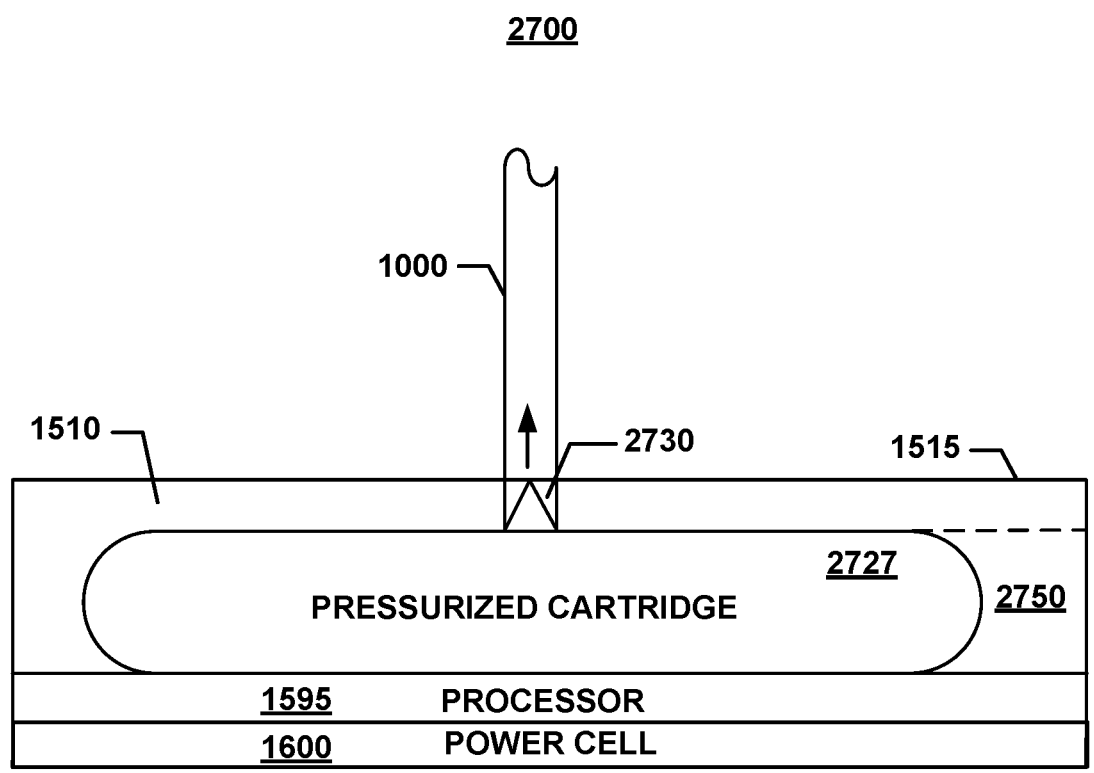
FIG. 27 is a block diagram of a DPAP device according to another embodiment of the present invention, shown using a pressurized cartridge as a stimulation source.

FIG. 27 represents a DPAP device 2700 according to another embodiment of the present invention, shown using a pressurized cartridge 2727 as a stimulation source. In this embodiment, the DPAP device 2700 uses the pressurized cartridge as its stimulation source, thus simplifying its operation and reducing its cost.

The DPAP device 2700 uses the processor 1595 to regulate the opening and closing of an outlet valve 2730, to deliver the stimulation, as described herein, via the nasal tube 1000. The pressurized cartridge 2727 can be filled with either air or another appropriate breathing gas, under pressure.

Since the use of the pressurized cartridge 2727 is limited during sleep, the size of the pressurized cartridge 2727 can be miniaturized. The pressurized cartridge 2727 can be replaced, as needed, by sliding it in and out of the body 1510 through an opening 2750.

Figure 28:
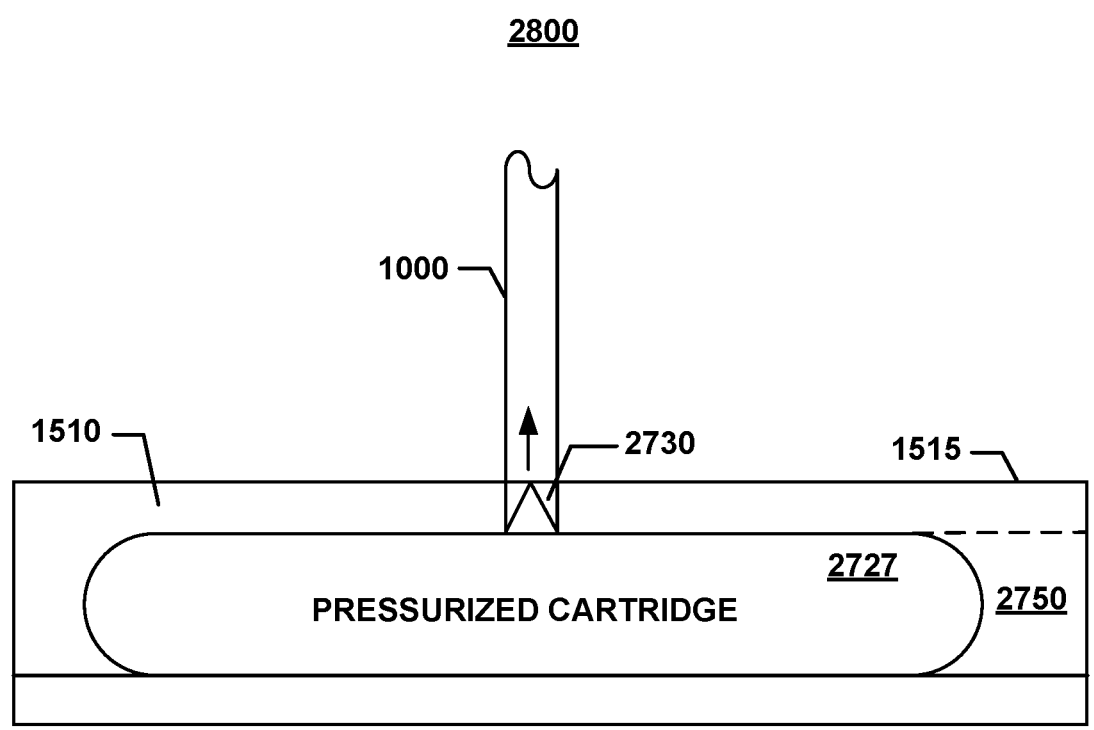
FIG. 28 is a block diagram of an alternative DPAP device, similar to that illustrated in FIG. 27, according to another embodiment of the present invention, shown using a pressurized cartridge as a stimulation source, but without a processor or a power cell.

FIG. 28 is a block diagram of an alternative DPAP device 2800 that is generally similar to the DPAP device 2700 of FIG. 27, according to another embodiment of the present invention, shown using a pressurized cartridge 2727 as a stimulation source, but without the processor or power cell of the DPAP device 2700. According to this embodiment, the outlet valve 2730 is regulated to open and close and thus to respectively release or block the flow of the gas or air, by, for example, the respiration sensor 126.

Figure 29:
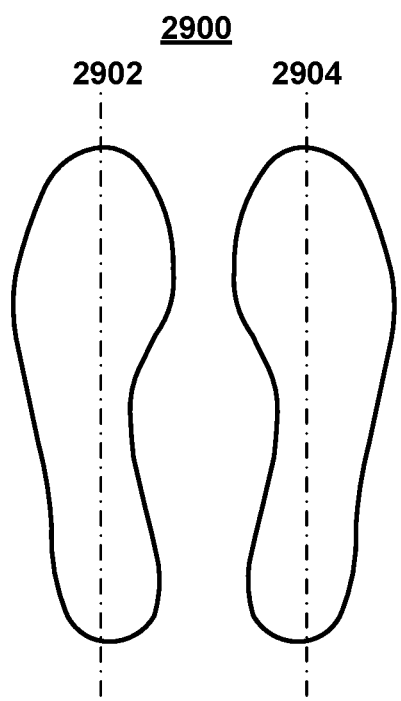
FIGS. 29, 30-, 31, 32, 33, 34, 35, 36 represent bottom views of shoe soles (or bottoms of the feet), that illustrated various resting feet positions relative to each other.

FIGS. 29 through 36 represent bottom views of shoe soles (or bottoms of the feet), that illustrated various resting feet positions relative to each other. FIG. 29 shows shoe soles 2900 positioned in a resting (i.e., non-moving) standing position, which represents an ideal position (also referred herein to as target or redress position), in which the soles (or feet) 2900 are aligned with two parallel, longitudinal axes 2902, 2904 (also referred to herein as target or redress axes).

Figure 30:
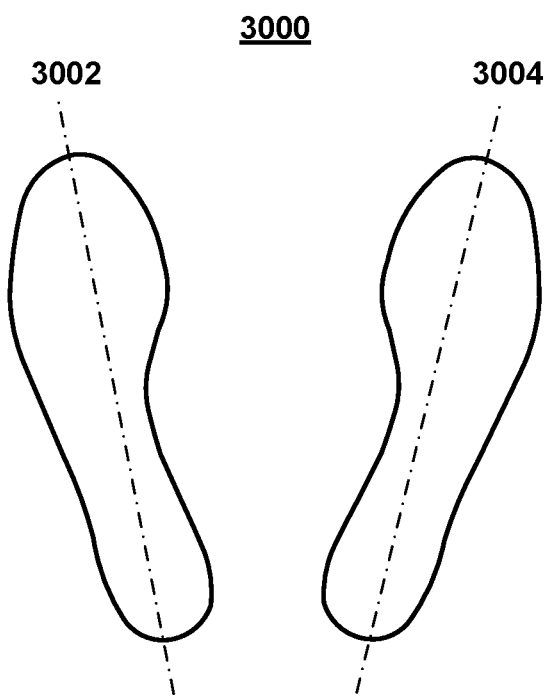

FIG. 30 shows shoe soles 3000 positioned in a resting (i.e., non-moving) standing position, which represents an undesirable position that requires redress according to one or more embodiments of the present disclosure. In this position, both longitudinal axes 3002, 3004 of the soles (or feet) 3000 diverge from the redress axes 2902, 2904 of FIG. 29.

Figure 31:
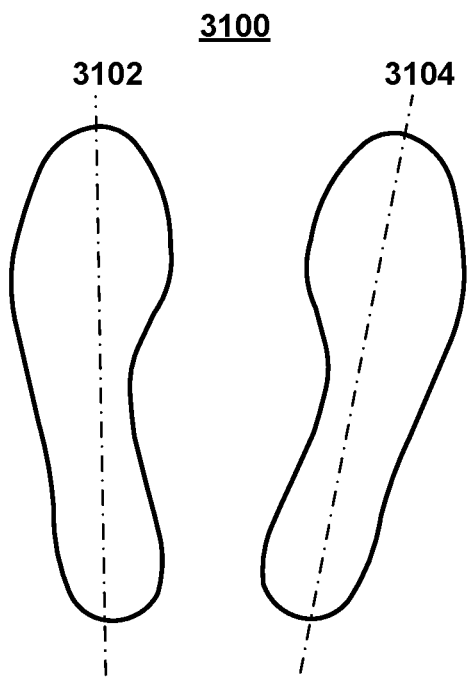

FIG. 31 shows shoe soles 3100 positioned in a resting (i.e., non-moving) standing position, which represents an undesirable position that requires redress according to one or more embodiments of the present disclosure. In this position, one of the longitudinal axes 3102, 3104 of the soles (or feet) 3100 diverges from the redress axes 2902, 2904 of FIG. 29.

Figure 32:
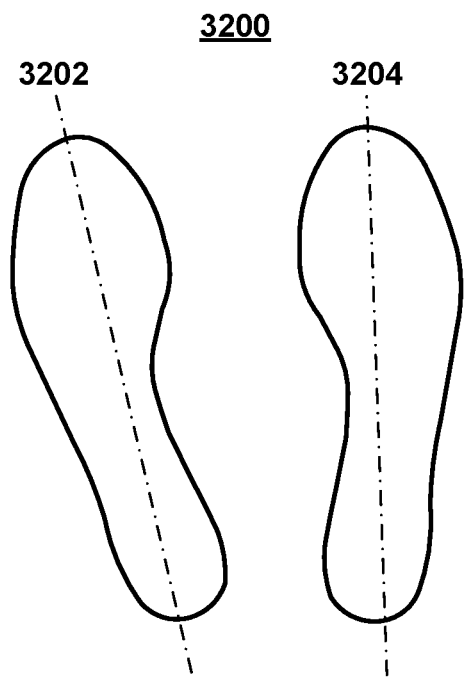

Similarly, FIG. 32 shows shoe soles 3200 positioned in a resting (i.e., non-moving) standing position, which represents an undesirable position that requires redress according to one or more embodiments of the present disclosure. In this position, one of the longitudinal axes 3202, 3204 of the soles (or feet) 3200 diverges from the redress axes 2902, 2904 of FIG. 29.

Figure 33:
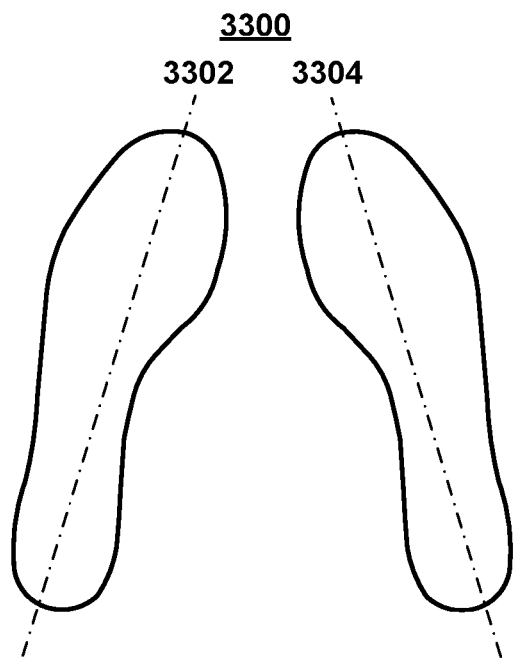

FIG. 33 shows shoe soles 3300 positioned in a resting (i.e., non-moving) standing position, which represents an undesirable position that requires redress according to one or more embodiments of the present disclosure. In this position, both longitudinal axes 3302, 3304 of the soles (or feet) 3300 converge relative to the redress axes 2902, 2904 of FIG. 29.

Figure 34:
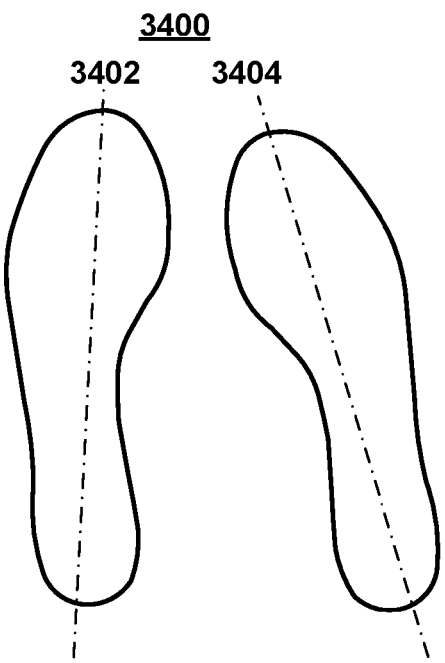

FIG. 34 shows shoe soles 3400 positioned in a resting (i.e., non-moving) standing position, which represents an undesirable position that requires redress according to one or more embodiments of the present disclosure. In this position, one of the longitudinal axes 3402, 3404 of the soles (or feet) 3400 converges relative to the redress axes 2902, 2904 of FIG. 29.

Figure 35:
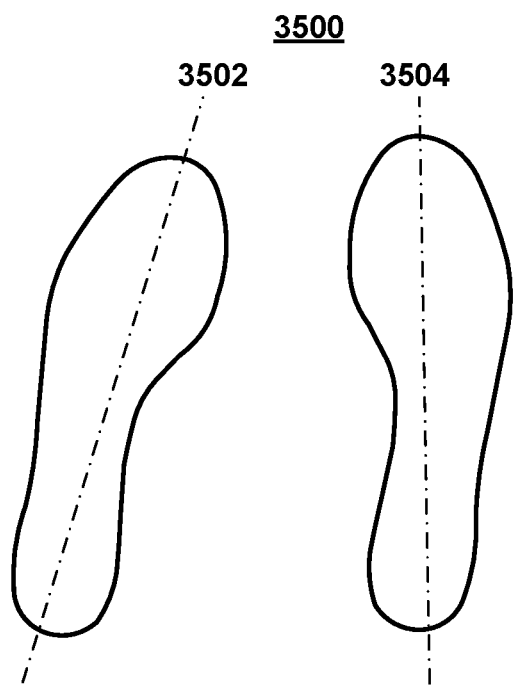

Similarly, FIG. 35 shows shoe soles 3500 positioned in a resting (i.e., non-moving) standing position, which represents an undesirable position that requires redress according to one or more embodiments of the present disclosure. In this position, one of the longitudinal axes 3502, 3504 of the soles (or feet) 3500 converges relative to the redress axes 2902, 2904 of FIG. 29.

Figure 36:
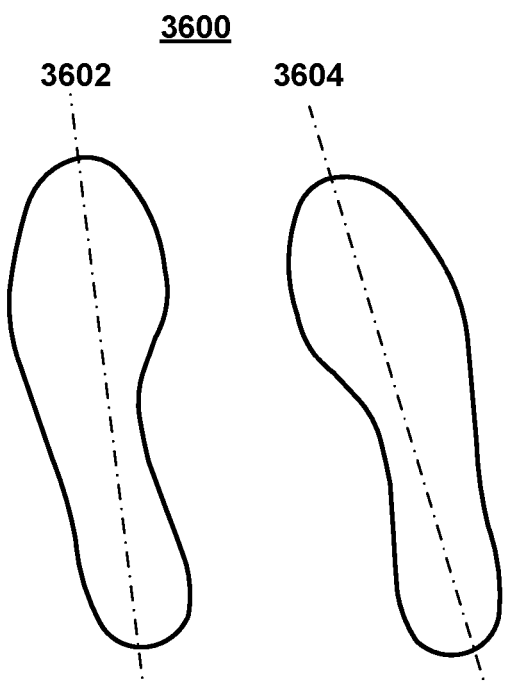

FIG. 36 shows shoe soles 3600 positioned in a resting (i.e., non-moving) standing position, which represents an undesirable position that requires redress according to one or more embodiments of the present disclosure. In this position, both longitudinal axes 3602, 3604 of the soles (or feet) 3600 deviate from the redress axes 2902, 2904 of FIG. 29.

Figure 37:
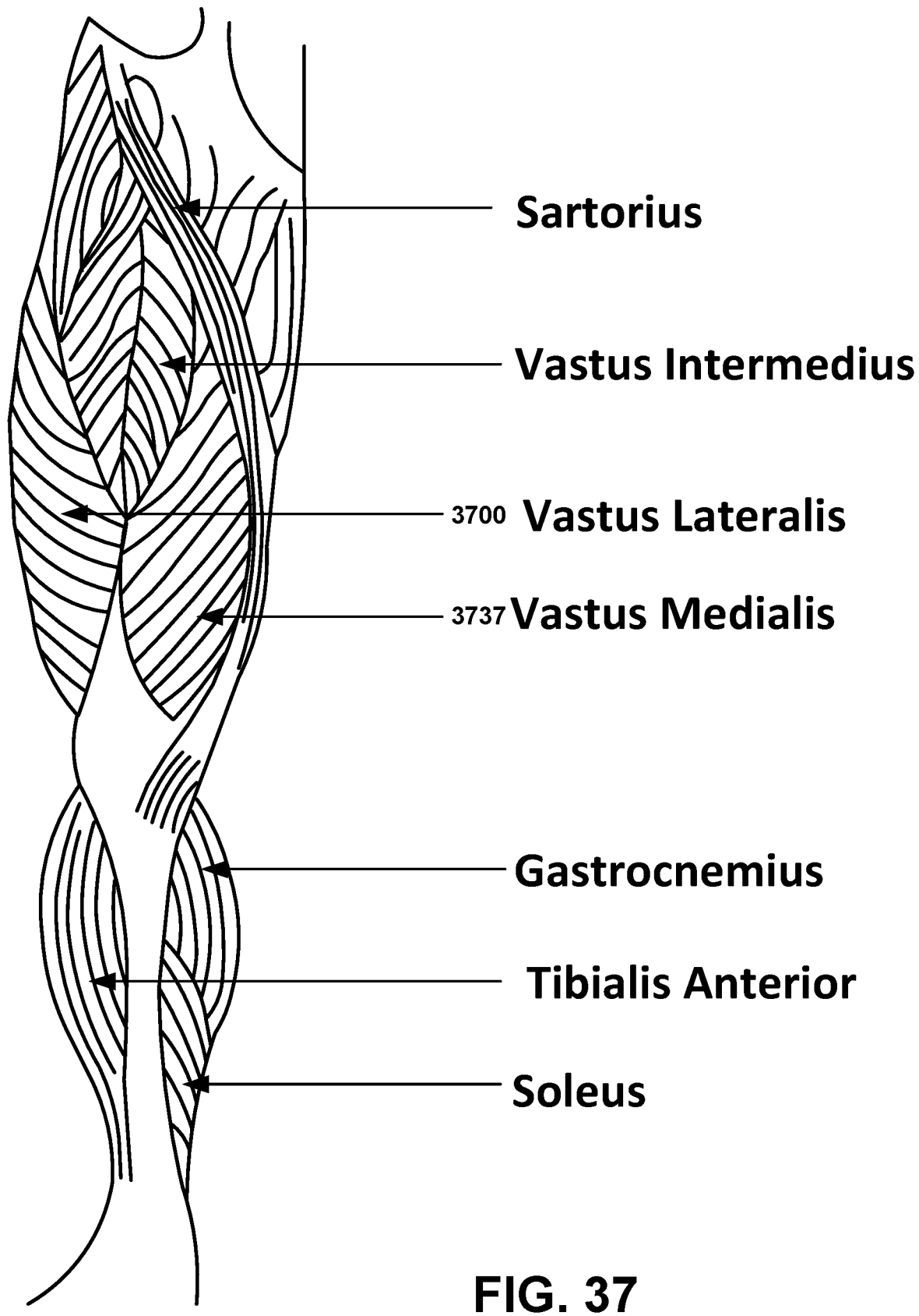
FIG. 37 is a general illustration of the right leg muscles showing complementary muscles, such as the vastus leteralis and the vastus medialis, that can be toned by the present invention.

While FIGS. 29 through 36 illustrate various resting feet positions, it should be understood that moving (i.e., running or walking) might carry over (i.e., translate) these positions and possibly exacerbate the disparity in the leg muscle development. FIG. 37 provides a general, visual illustration of such exemplary leg muscles that might be affected by unbalanced development.

As background information, the thigh has three sets of strong muscles: the hamstring muscles in the back of the thigh, the quadriceps muscles in the front, and the adductor muscles on the inside. The quadriceps muscles and hamstring muscles work together to straighten (extend) and bend (flex) the leg. The adductor muscles pull the legs together. The skeletal muscles are generally grouped together in pairs on the skeleton, and they interact and work together in opposition.

Skeletal muscles only pull in one direction. For this reason, they always come in pairs, wherefore these pairs of muscles will be referred to herein as "complementary muscles." When one muscle in a pair contracts, to bend a joint for example, its counterpart then contracts and pulls in the opposite direction to straighten the joint out again. Without this arrangement, a person would not be able to straighten the legs when walking or bending the fingers to grip something. As an example, when the biceps muscle in the upper arm contracts, it pulls the lower arm in towards the shoulder. However, when it relaxes, the biceps cannot push the arm back out. To do this, the triceps muscle, on the underside of the upper arm contracts and straightens the arm out. If the triceps muscle were not there, the arm would stay drawn in permanently.

Similarly, the skeletal muscles of the legs work in opposition. As an example, the vastus lateralis 3700, which is also called the "vastus externus" is the largest and most powerful part of the quadriceps femoris. It arises from a series of flat, broad tendons attached to the femur, and attaches to the outer border of the patella. It ultimately joins with the other muscles that make up the quadriceps in the quadriceps tendon, which travels over the knee to connect to the tibia.

The muscle that interact with the vastus lateralis 3700 is the vastus medialis 3737, which is also called the vastus internus is an extensor muscle located medially in the thigh that extends the knee. The vastus medialis 3737 is part of the quadriceps muscle group.

There exists a direct relationship between the two vastus lateralis 3700 and the two vastus medialis 3737 of both legs on one end, and the positioning of the feet on the other end. More specifically, If the vastus lateralis 3700 of one leg were more developed than the vastus medialis 3737, then the vastus lateralis 3700 will pull the associated foot outward. Similarly, if the vastus medialis 3737 of the leg were more developed than the vastus lateralis 3700, then the vastus medialis 3737 prevails, and will pull the associated foot inward.

More specifically, FIG. 29 shows shoe soles (or feet) 2900 positioned in an ideal position, indicating that the vastus lateralis 3700 and the vastus medialis 3737 are properly and symmetrically "toned" in that they tend to exert the appropriate balanced pull forces on the feet 2900, to keep them aligned with the longitudinal axes 2902, 2904.

On the other hand, FIG. 30 shows shoe soles (or feet) 3000 that are positioned in an undesirable position which requires redress according to one or more embodiments of the present disclosure. In this position, the vastus lateralis muscles 3700 of both legs is more developed than the corresponding vastus medialis muscles 3737, and thus these complementary muscles tend to exert asynchronous, unbalanced pull forces on the feet 3000, causing the latter to diverge outwardly from the redress axes 2902, 2904 of FIG. 29.

FIG. 31 shows shoe soles (or feet) 3100 that are positioned in an undesirable position which requires redress according to one or more embodiments of the present disclosure. In this position, the vastus lateralis muscles 3700 of the left leg (with a corresponding axis 3104) is more developed than the corresponding vastus medialis muscles 3737, and thus these complementary muscles tend to exert asynchronous, unbalanced pull forces on the feet 3100, causing the left foot to diverge outwardly from the redress axis 2904 of FIG. 29.

FIG. 32 shows shoe soles (or feet) 3200 that are positioned in an undesirable position which requires redress according to one or more embodiments of the present disclosure. In this position, the vastus lateralis muscles 3700 of the right leg (with a corresponding axis 3102) is more developed than the corresponding vastus medialis muscles 3737, and thus these complementary muscles tend to exert asynchronous, unbalanced pull forces on the feet 3200, causing the right foot to diverge outwardly from the redress axis 2902 of FIG. 29.

FIGS. 33 through 36 illustrate variations of feet positions as described above in connection with FIGS. 29 through 32.

Figure 38:
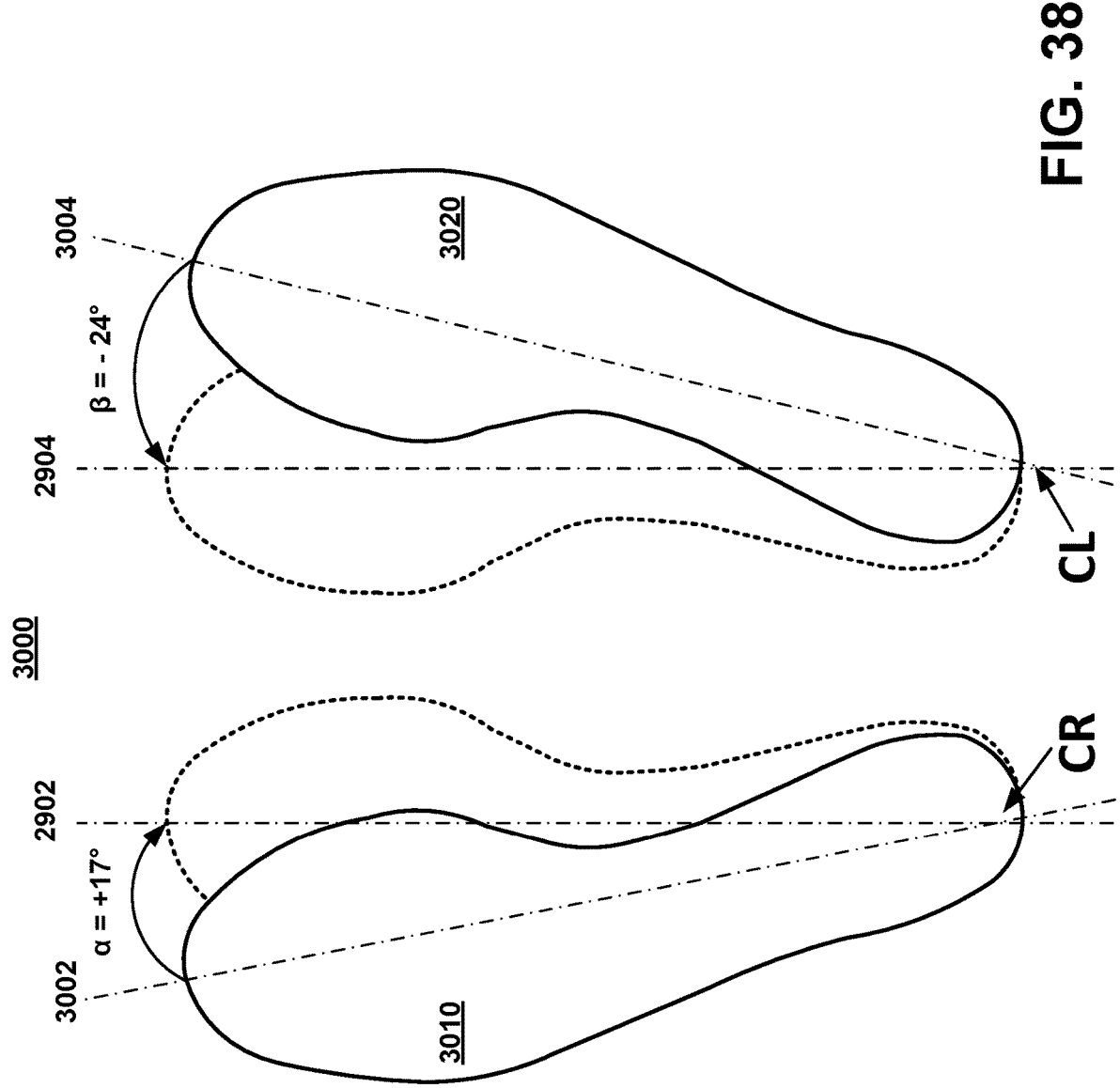
FIGS. 38 and 39 represent the bottoms of the feet (or shoe soles) in two common resting positions, as shown in FIGS. 30 and 33 respectively, and in redress positions.

FIG. 38 illustrates the soles (also referred to herein as "sole pair") 3000 that include a right sole 3010 and a left sole 3020. In this example, the axis 3002 of the right sole 3010 deviates by an angle $\alpha$ of approximately +17° from the corresponding redress axis 2902. Similarly, the axis 3004 of the left sole 3020 deviates by an angle $\beta$ of approximately −24° from the corresponding redress axis 2904. In other terms, both feet or soles 3010, 3020 need to be rotated in opposite directions toward the redress positions shown in FIG. 29, so that the axis 3002 corresponds with the redress axis 2902, and the axis 3004 corresponds with the redress axis 2904. In addition, the redress positions need to be maintained so that the vastus lateralis muscles 3700 and the vastus medialis muscles 3737 of both legs be trained and remain synchronously toned.

The center of rotation CR of the right sole (or foot) 3010 is defined herein as the intersection of the axis 3002 and the redress axis 2902. Similarly, the center of rotation LR of the left sole (or foot) 3020 is defined herein as the intersection of the axis 3004 and the redress axis 2904. It should be noted that while the center of rotation CR falls within the footprint of the sole 3010, the center of rotation LR falls outside the footprint of the sole 3021 and is thus referred to herein as a virtual center of rotation. It should also be noted in this example that the angles of rotations $\alpha$ and $\beta$ do not necessarily need to be equal and that each foot needs to be redressed differently.

Figure 39:
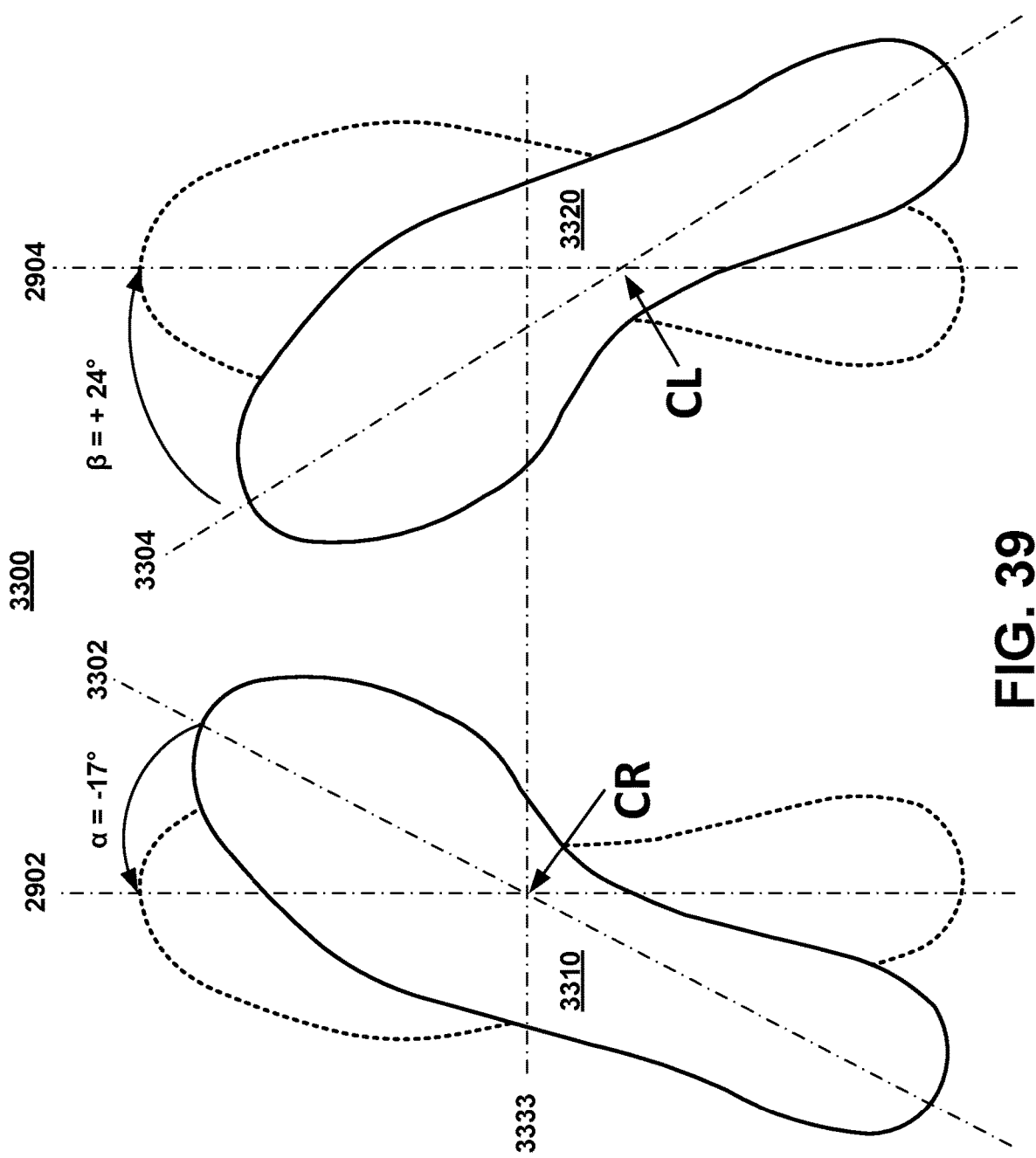

FIG. 39 illustrates the soles (also referred to herein as "sole pair") 3300 that include a right sole 3310 and a left sole 3320. In this example, the axis 3302 of the right sole 3310 deviates by an angle $\alpha$ of approximately −17° from the corresponding redress axis 2902. Similarly, the axis 3304 of the left sole 3320 deviates by an angle $\beta$ of approximately +24° from the corresponding redress axis 2904. In other terms, both feet or soles 3310, 3320 need to be rotated in opposite directions toward the redress positions shown in FIG. 29, so that the axis 3302 corresponds with the redress axis 2902, and the axis 3304 corresponds with the redress axis 2904. In addition, the redress positions need to be maintained so that the vastus lateralis muscles 3700 and the vastus medialis muscles 3737 of both legs be trained and remain synchronously toned.

This example illustrates the fact that the center of rotations CR and CL do not necessarily have to lie along axis 3333, which is perpendicular to the redress axes 2902, 2904.

Figure 40:
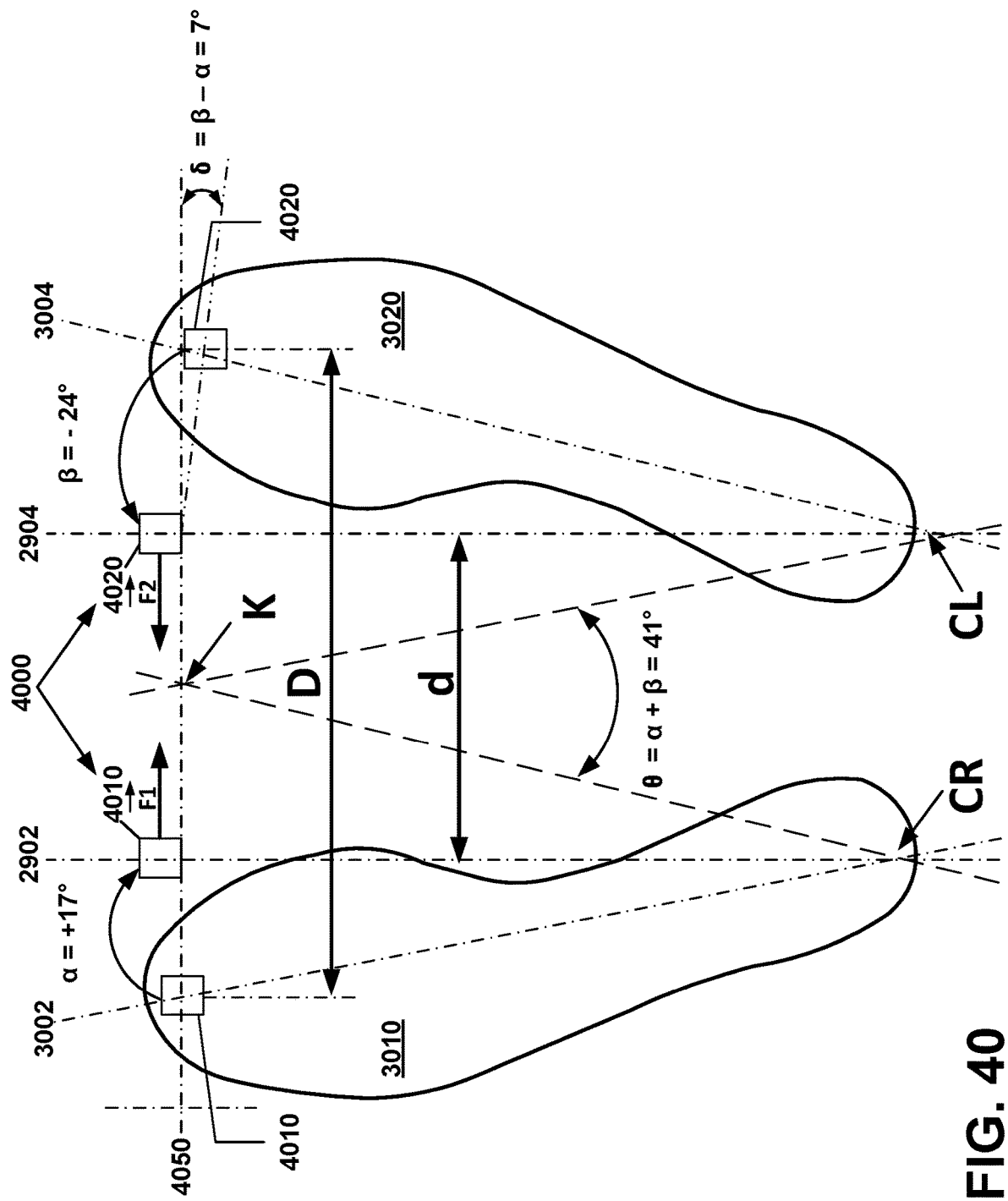
FIG. 40 represents the bottom view of the representative shoe soles of FIG. 38, shown provided with a mechanism for redressing the positions of the shoe soles, in order to adjust the corresponding feet positions, according to one embodiment of the present disclosure.
Figure 41:
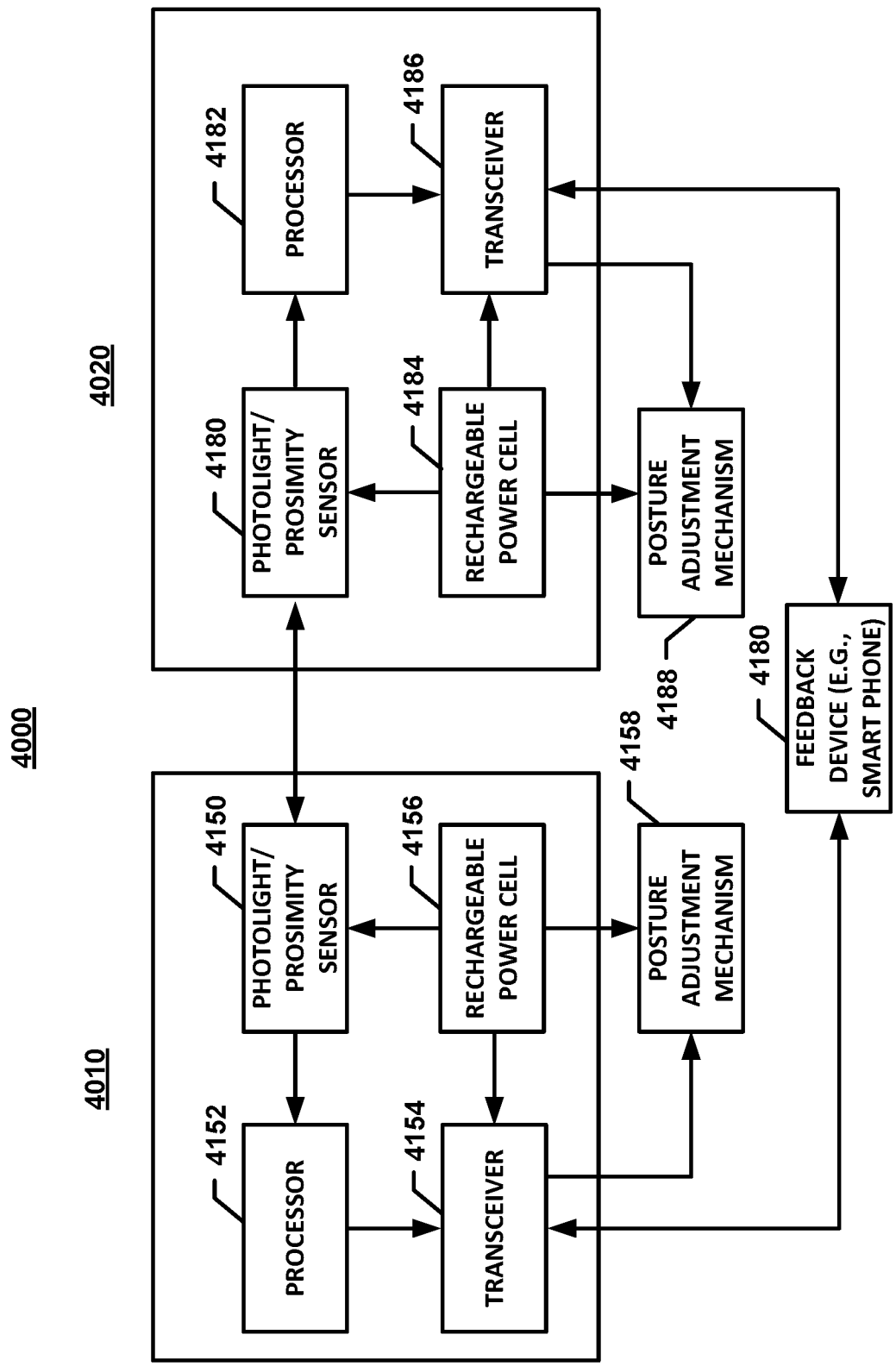
FIG. 41 is a block diagram of the redress mechanism of FIG. 40, according to one embodiment of the present disclosure.
Figure 42:
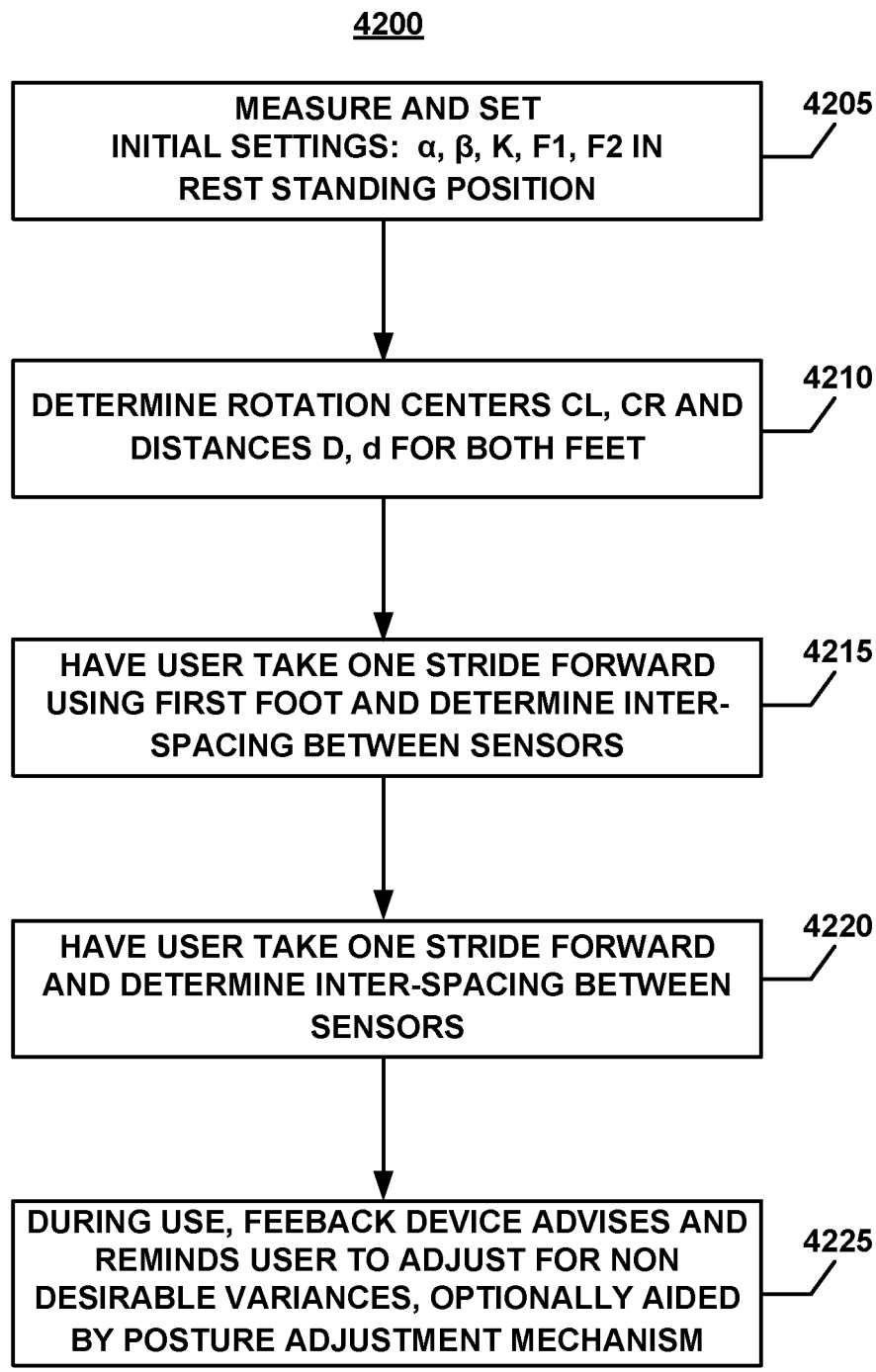
FIG. 42 is a flow chart illustrating a process for redressing the positions of the shoe soles in order to adjust the corresponding feet positions, according to one embodiment of the present disclosure.

Referring now to FIGS. 40, 41, 42, and starting with FIG. 40, it represents the bottom view of the representative shoe soles 3010, 3020 of FIG. 38, shown provided with a redress mechanism 4000 comprised of devices (or elements) 4010, 4020 for redressing the positions of the shoe soles 3010, 3020, respectively, in order to adjust the corresponding feet positions, according to one embodiment of the present disclosure.

FIG. 41 is a block diagram of the redress mechanism 4000 of FIG. 40, according to one embodiment of the present disclosure. FIG. 42 is a flow chart illustrating a process 4200 for redressing the positions of the shoe soles 3010, 3020 in order to adjust the corresponding feet positions, according to one embodiment of the present disclosure.

The redress mechanism 4000 aims at redressing the shoe soles 3010, 3020 along the respective redress axes 2902, 2904, and further at maintaining such redress over an extended period of time (e.g., ranging from minutes to hours), in order to cause the complimentary skeletal muscles to be toned and consequently assume the redress action (or process) on their own. To this end, the redress mechanism 4000 is comprised of devices (or elements) 4010, 4020 (FIGS. 40, 41) that are respectively secured to the shoe sole 3010, 3020.

While the present disclosure describes one embodiment of the present invention as securing the redress mechanism 4000 to the shoe soles 3010, 3020, it should be clear that the redress mechanism 4000 may alternatively be incorporated within insoles (also represented by the numeral references 3010, 3020) that can be inserted inside the shoe soles. Alternatively, the redress mechanism 4000 may be attached the lower legs, above the shoes. It should also be clear that while the present invention is described herein in connection with leg muscles and footwear, it is not limited to this particular application. Rather, the present invention may be used with other complementary muscles of the body for numerous purposes, including, without limitation: physical therapy, and exercises.

With reference to FIG. 40, one of the main goals of the redress mechanism 4000 is to cause the constituent elements 4010, 4020 to force the sole axes 3002, 3004 to rotate by appropriate angles, so that they become aligned with the respective redress axes 2902, 2904. In addition, the redress elements 4010, 4020 will exert the necessary attraction forces F1, F2, to maintain the shoe soles 3010, 3020 in the redress position, for an extended period of time. According to another embodiment, the redress mechanism does not provide the attraction forces, but rather provides the user with a feedback signal or message when the shoe soles 3010, 3020 become misaligned (within a certain range) relative to the redress axes 2902, 2904, to advise the user that an adjustment is needed.

According to the latter embodiment, and with reference to FIG. 41, the elements 4010 and 4020 of the redress mechanism 4000 include sensors 4150, 4180, respectively. These sensors 4150, 4180 work in conjunction with each other to generate a feedback signal whenever the two soles 3010, 3020 are not within the parameters of a predetermined redress position. Although the ideal redress position may be illustrated in FIG. 29, it should be understood that for certain users, such as patients, such ideal redress position might not be the desired position, and as such, acceptable parameters or ranges of positions may be set or individualized for each user.

One or more processors, such as the processors 4152 and 4182, may be integrated as part of the elements 4010 and 4020 to evaluate the feedback signals generated by the sensors 4150, 4180, and to forward the appropriate warning signal to a user feedback device 4190, via one or more transceiver 4154, 4184. In a more simplified design, only one processor and one transceiver may be used. In an alternative embodiment, the processors 4152, 4182 are eliminated altogether, and the raw signals are transmitted directly to the external feedback device 4180 for processing and determination of the proximity of the two elements 4010, 4020 relative to each other. These raw signals may be transmitted, wirelessly through one or more transceivers 4154, 4184 to either the user through the external feedback device 4180, or to one or more posture adjustment mechanisms 4158, 4188 that provide automatic redress, as it will be explained later in more detail.

The sensors 4150, 4180 may include a photo-light sensor or a proximity sensor that measures the proximity of the two elements 4010, 4020, and thus the two shoe soles 3010, 3020, relative to each other.

A rechargeable power cell 4156, 4186 may be used within each element 4010, 4020, to power the sensors 4150, 4180, the transceivers 4154, 4184, and the posture adjustment mechanisms 4158, 4188. A separate rechargeable power cell may be used to power the feedback device 4180. Some or all of the rechargeable power cells may be of the type described herein, using the body's own temperature heat, foot pressure, or any other source described herein.

With reference to steps 4205 and 4210, the redress process 4200 is initiated by measuring and setting the initial settings for each foot or sole of the user, in a rest standing position. To this end, and with further reference to FIG. 41, the axes 3002 and 2902 (described earlier) of the right sole 3010 are drawn or measured in order to determine the center of rotation CR, the angle of rotation a (which in this example is a=+17°, and the center reference point, K, which is the midpoint between the two redress axes 2902, 2904 along axis 4050 that virtually connects the elements 4010, 4020 and that is perpendicular (or normal) to the redress axes 2902, 2904.

Similarly, and with respect to the left sole 3020, the axes 3002 and 2902 (described earlier) are drawn or measured in order to determine the center of rotation CL, and the angle of rotation $\beta$ (which in this example is $\beta=-24°$. The weight, height, and pace size of the user are also measured, as well as the location of pressure (or contact) points of the soles with ground as the soles land on the ground while the user is walking (running, or performing another activity).

As shown in FIG. 40, the elements 4010, 4020 may, for example only, be disposed near the tip of the soles 3010, 3020, along the axes 3002, 3004, although other locations may alternatively be appropriate. At step 4210 of the process 4200 the distance, D, between the two elements 4010, 4020 in the resting position is measured or determined. Similarly, the distance, d, between the two elements 4010, 4020 in the redress position is also measured or determined.

Figure 44:
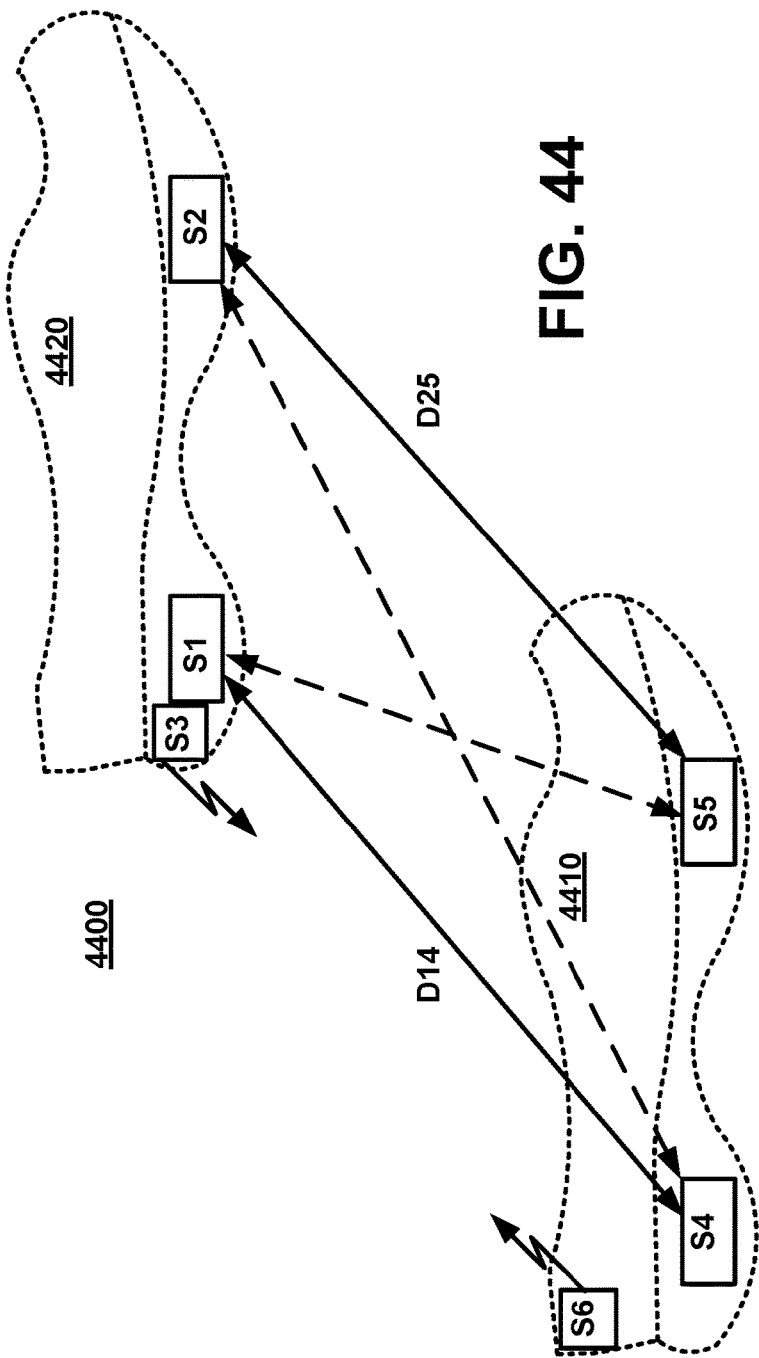
FIG. 44 is an elevational view of two shoes (footwear in dotted lines) illustrating yet another mechanism for redressing the positions of the shoe soles for adjusting the corresponding feet positions, according to one embodiment of the present disclosure.

At step 4220 of the process 4200, the user is requested to take one stride forward, as is shown in FIG. 44, and the distance between the two elements 4010, 4020 is measured. In FIG. 44, the two elements are designated by the references S2, S5, and the distance therebetween is designated by S25, which is measured or calculated.

Using the foregoing data points, the processors 4152, 4182 and/or the external feedback device 4180 estimates (or approximates) the forces F1, F2 that need to be exerted on each sole 3010, 3020, independently, to cause redress. It should be noted that the forces F1, F2 do not necessarily need to be equal, and that these forces F1, F2, whether they are attraction or repulsion forces, are calculated individually for each foot or sole.

At step 4225, and as explained earlier, during use, the feedback device 4180 advises or reminds the user to adjust for non-desirable variances, optionally aided by the posture adjustment mechanism 4158, 4188.

According to one embodiment of the present invention, the posture adjustment mechanism 4158, 4188 may include two electro-magnets that are polarized so that they are attracted to (or alternatively, for the position shown in FIG. 39, repulsed from) each other, thus forcing one or both soles or feet to also be rotated toward the desired redress position. It should be understood that while the present invention is described in more detail with regard to the generation of attraction forces F1, F2, it should be clear that repulsive forces may be generated using a similar concept.

Figure 43:
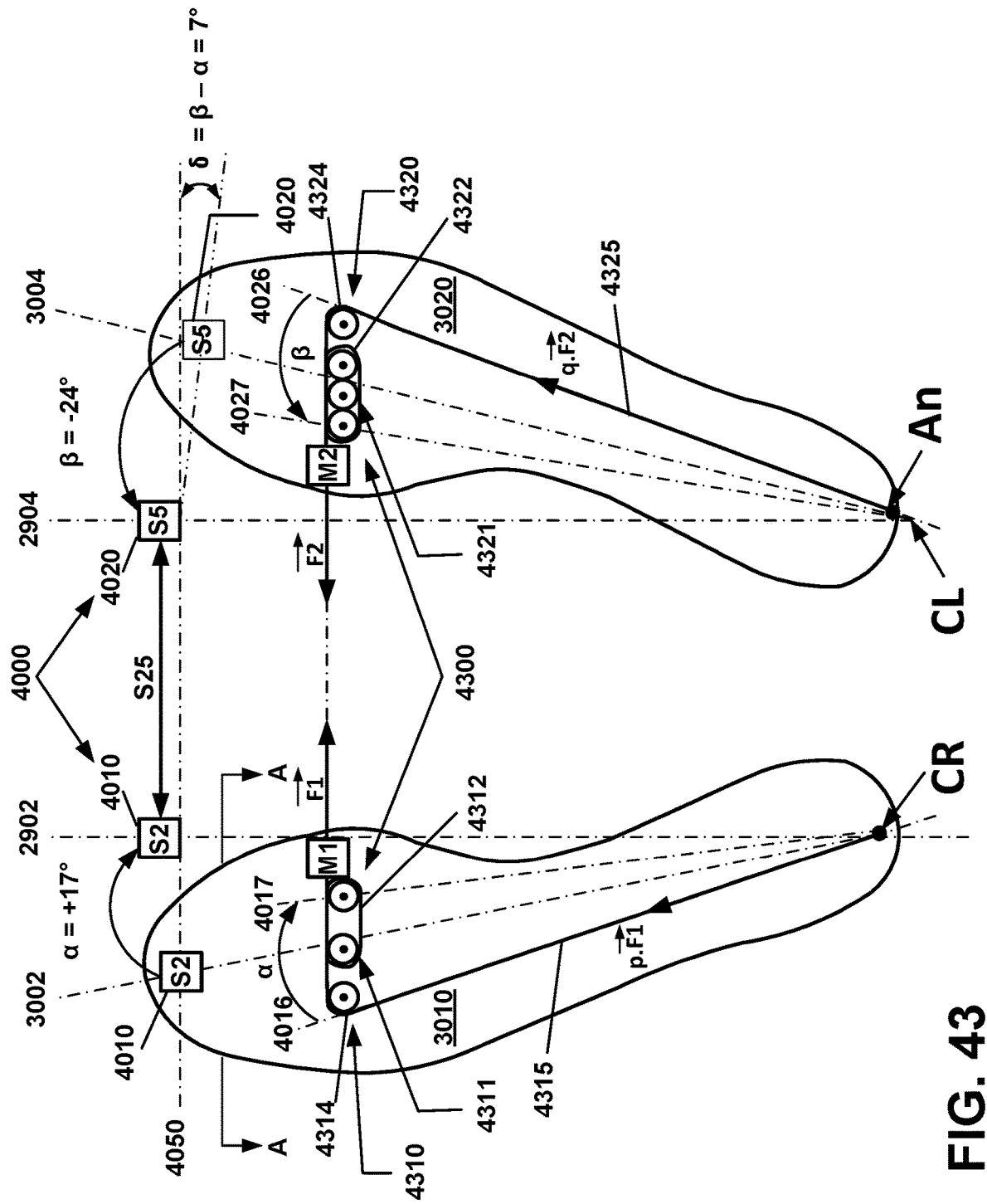
FIG. 43 represents the bottom view of the representative shoe soles of FIG. 40, shown provided with another mechanism for redressing the positions of the shoe soles, in order to redress the corresponding feet positions, according to one embodiment of the present disclosure.

FIG. 43 represents the bottom view of the representative shoe soles 3010, 3020 of FIG. 40, shown provided with the first redress mechanism 4000 and further provided with a second redress mechanism 4300 for redressing the positions of the shoe soles, in order to redress the corresponding feet positions, according to one embodiment of the present disclosure.

In this illustration, and as described earlier, the first redress mechanism 4000 includes two elements 4010, 4020. These elements 4010, 4020 may be sensors and/or electro-magnets; however, for the sake of this example, the two elements 4010, 4020, will be assumed to be sensors S2, S5, respectively, and that the second redress mechanism 4300 includes the two electro-magnets M1, M2.

The second redress mechanism 4300 will now be described in more detail. The second redress mechanism 4300 generally includes two pulley-driven mechanisms 4310, 4320, one for each sole 3010, 3020, respectively. These pulley-driven mechanisms 4310, 4320 can for example, be encapsulated within the shoe soles 3010, 3020. Starting with the right sole mechanism 4310, it generally includes a magnet M1 or a solenoid (FIGS. 56-59), such as an electro-magnet that generates a force F1. In this example, the force F1 is an attraction force. However, it should be clearly understood that the present invention is not limited to attraction forces, but the magnet M1 may be so polarized as to exert either an attraction or a repulsion force.

The right sole redress mechanism 4310 further includes a pulley mechanism 4311 that is secured to the magnet M1 (or the plunger of the solenoid). The pulley mechanism 4311 includes a pulley setup 4312 that amplifies the attraction force F1 by a factor "p" so that the effective pull or attraction force becomes pF1. The pulley mechanism 4311 further includes an additional pulley (or another mechanism) 4314 that changes the direction of the force to provide a lever effect.

To this end, the pulley mechanism 4311 further includes a cable 4315 that is secured to the magnet M1 and to the pulley setup 4312, and that further wraps around the pulley 4314, to be connected to the center of rotation CR that acts as an anchor. As a result, the right sole redress mechanism 4310 effectively exerts the force pF1 around the center of rotation CR.

In this illustration, the number of force amplifying pulleys is shown to be two; however, a different number of force amplifying pulleys may be selected dependent on the desired angle of rotation a and the amplification factor "p." In one embodiment, the angle of rotation a is set to be equal to the angle formed between axes 4016 and 4017. Axis 4016 may be the extension of the cable 4315, while axis 4017 may be formed by the center of rotation CR and the center of the first pulley, nearest the magnet M1.

Figure 43A:
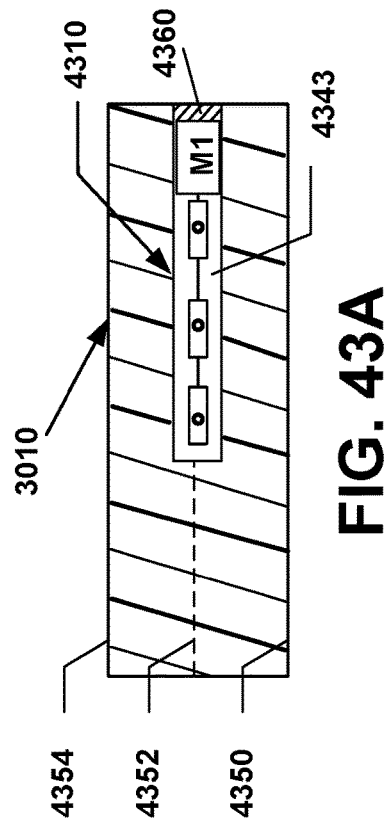
FIG. 43A is a cross-sectional view of the right shoe sole of FIG. 43, taken along line A-A thereof, according to one embodiment of the present disclosure.

FIG. 43A is a cross-sectional view of the right shoe sole 3010 of FIG. 43, taken along line A-A thereof, according to one embodiment of the present disclosure. FIG. 43A illustrates one exemplary way of encapsulating the right sole redress mechanism 4310 with the sole 3010. The right sole 3010 can be molded or manufactured integrally to incorporate the redress mechanism 4310.

Alternatively, the shoe sole 3010 can be formed of a bottom part 4350 that is molded to form the lower half of a spacing of chamber 4343 that houses the redress mechanism 4310 when the shoe sole 3010 is assembled. The individualized redress mechanism 4310 is then assembled within the chamber 4343. An upper part 4354 of the shoe sole 3010 is then formed and secured to the bottom part 4350 along the surface represented by a dashed line 4352. It should be noted that the chamber 4343 enables the pulley assembly to function freely therewithin, without obstruction.

A plug 4360 made of a suitable material may be formed to complete the encapsulation of the pulley assembly 4310 within the sole 3010. The plug 4360 may be made, for example, of a plastic material. Alternatively, the plug 4360 may be made of a material that is conductive to generated electro-magnetic field of the magnet M1. In the latter example, it would be desirable to include another plug on the opposite side to that of the plug 4360. The pulley assembly 4320 of the left sole 3020 may be made similarly to the assembly method described herein in connection with FIG. 43A.

Returning now to pully driven mechanism 4320 of FIG. 43, it generally includes a magnet M2 or a solenoid (FIGS. 56-59) that is generally similar to the magnet M1, for generating a force F2. In this example, the force F2 is an attraction force. However, it should be clearly understood that the present invention is not limited to attraction forces, but the magnet M2 may be so polarized as to exert either an attraction or a repulsion force.

The left sole redress mechanism 4320 further includes a pulley mechanism 4321 that is secured to the magnet M2 (or the plunger of the solenoid). The pulley mechanism 4321 includes a pulley setup 4322 that amplifies the attraction force F2 by an amplification factor "q" so that the effective pull or attraction force becomes qF2. The pulley mechanism 4311 further includes an additional pulley (or another mechanism) 4324 that changes the direction of the force to provide a lever effect.

To this end, the pulley mechanism 4321 further includes a cable 4325 that is secured to the magnet M2 and to the pulley setup 4322, and that further wraps around the pulley 4324, to be connected to a substitute center of rotation "An" that acts as an anchor. The reason for the selection of the substitute center of rotation "An" is that in this illustration, the actual center of rotation CL is virtual and thus the substitute center of rotation "An" is selected on the rearward or rearwardmost part of the sole 3020, in proximity (or in closest proximity) to the center of rotation CL. As a result, the left sole redress mechanism 4320 effectively exerts the force qF2 around the substitute center of rotation "An."

In this illustration, the number of force amplifying pulleys is shown to be three; however, a different number of force amplifying pulleys may be selected dependent on the desired angle of rotation β and the amplification factor "q." In one embodiment, the angle of rotation β is set to be equal to the angle formed between axes 4026 and 4027. Axis 4026 may be the extension of the cable 4325, while axis 4027 may be formed by the substitute center of rotation "An" and the center of the first pulley, nearest the magnet M2.

It should be noted that the amplification factors "p" and "q" are not necessarily equal, depending on the required attraction force by each sole 3010, 3020. In this illustration, the redress angle of rotation β (which in this example is β=−24° is greater than the redress angle of rotation a (which in this example is a=+17°, and thus requires a greater attraction or redress force qF2. As a result, the pulley mechanism 4321 is illustrated to include three pulleys, while the pulley mechanism 4312 is shown to include two pulleys. Alternatively, the two redress pulley assemblies 4311 and 4321 may be identical but the magnets M1, M2 may be selected to generate the required attraction forces F1, F2.

Figure 45:
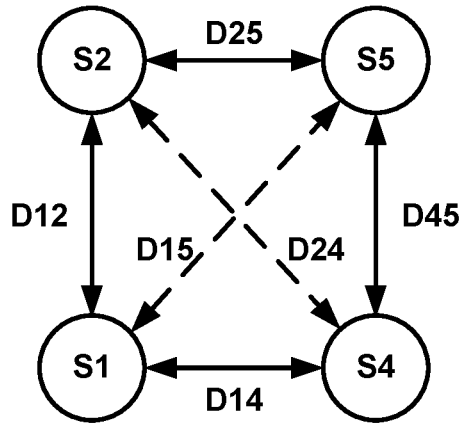
FIGS. 45, 46, 47 data points representations of the mechanism for redressing the positions of the shoe soles for adjusting the corresponding feet positions, according to one embodiment of the present disclosure.

FIG. 44 is an elevational view of two shoes (footwear in dotted lines), a right shoe 4410 and a left shoe 4420, and illustrates another mechanism 4400 for redressing the positions of the shoe soles in order to adjust the corresponding feet positions, according to one embodiment of the present disclosure. In addition to what has already been described earlier in connection with shoe soles, FIG. 44 illustrates a more elaborate data collection schemes of three-dimensionally positioned redress devices S1, S2, S3, S4, S5, S6 that acts as data points, as further illustrated in FIGS. 45, 46, 47.

Figure 46:
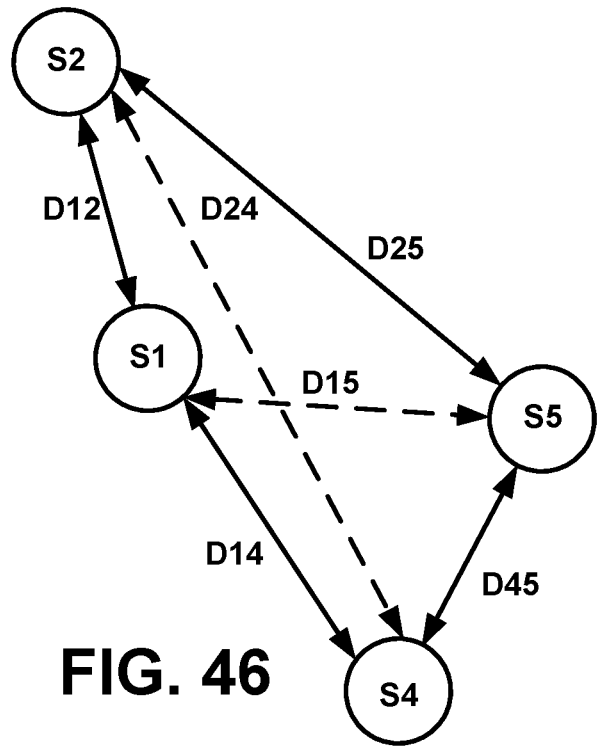
Figure 47:
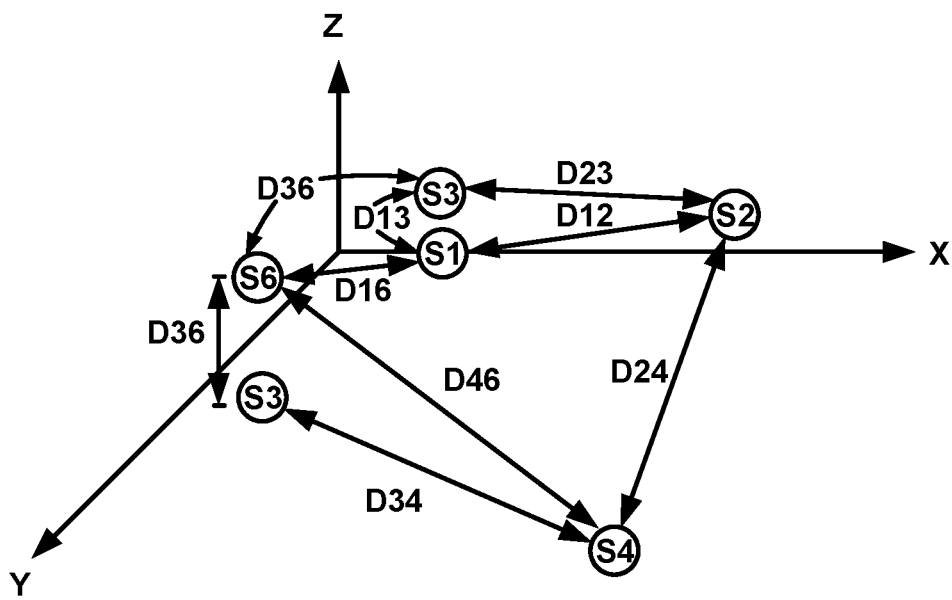

In these drawings, the designation "Dxy" refers to the distance between the redress devices Sx and Sy. For instance, D25 refers to the distance between the redress devices S2 and S5. To be noted that the redress devices S3 and S6 are secured to the upper part of the heels (along the Z-axis) so as to provide more accurate three-dimensional readings and redress adjustments. In FIGS. 44, 46, 47 the user is making a stride from the initial resting position of FIG. 45.

Figure 48:
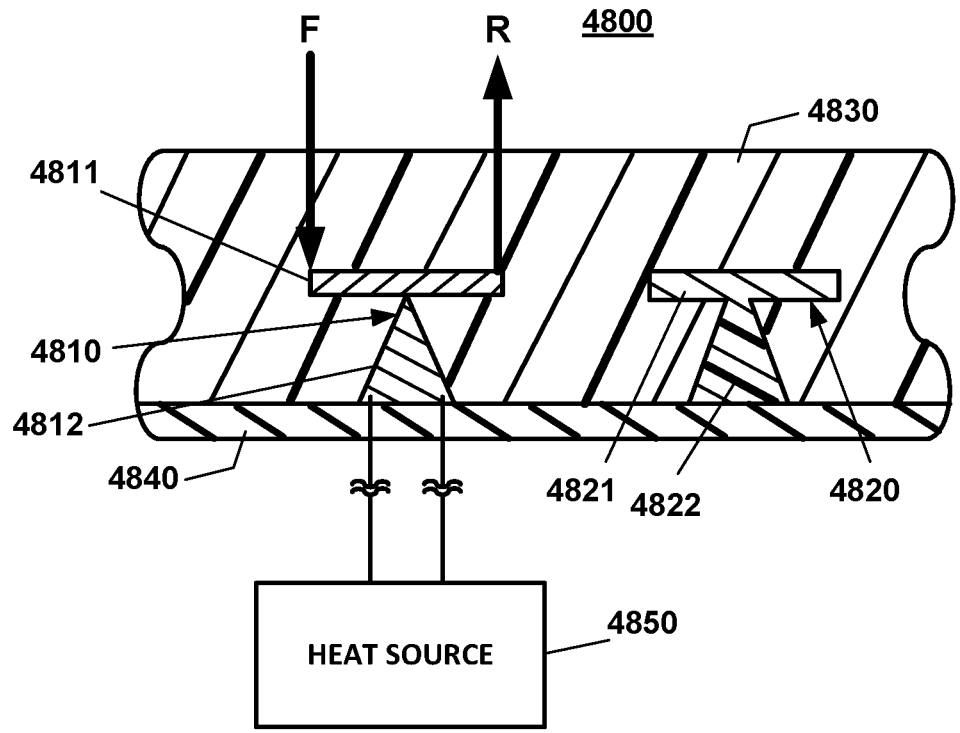
FIG. 48 is a cross-sectional, fragmentary view of a shoe sole (or fabric) that incorporates micro-levers according to one embodiment of the present disclosure.

FIG. 48 is a cross-sectional, fragmentary view of a shoe sole 4800 (fabric or any other suitable environment such as packaging, mattresses, etc.) that incorporates a plurality of micro-levers 4810, 4820, according to one embodiment of the present disclosure. In this example, the micro-levers 4810, 4820 are encapsulated within a synthetic resin or another suitable plastic, pliable material 4830 that is preferably but not necessarily formed on a base 4840 that may be formed for example, of rubber or hard plastic to provide solid support for the micro-levers 4810, 4820.

Considering now the micro-lever 4810, it is formed of a material that is stiffer or harder than the pliable material 4830, so that when a force is applied on the micro-lever 4810, it is capable of bending or plying in the direction of the applied force. Although two exemplary designs for the micro-levers 4810, 4820 are described herein, it should be understood that the inventive concept is applicable to differently shaped micro-levers.

The micro-lever 4810 is formed of two parts: an upper, balanced platform 4811; and a bottom support 4812. The upper platform 4811 is supported, in this example, on the apex of the bottom support, in order to form a lever, so that when force F is applied onto one end of the upper platform 4811, a reactive force R is generated on the other end of the upper platform 4811.

As a result, the micro-levers 4810, 4820 can be encapsulated within the sole or insole of a shoe to provide support and comfort. In this example, the micro-lever 4810 does not allow the force F to reach the ground, but rather selectively disperses, absorbs, redirects (i.e., changes the direction of) the force F, into the reactive force R that lifts the user's sole, thus aiding the user by providing added comfort during use.

A heat source 4850 may optionally be secured to the micro-lever 4810, heat it, so as to make the surrounding pliable material 4830 more compliant so as to allow the micro-lever 4810 to ply more easily. To this end, the micro-lever 4810 may be made of a metallic material that is conductive to heat. Although the heat source 4850 is shown as an external source, it should be clear that the heat source 4850 can be encapsulated within the base 4840, fed by friction, electricity, or any other suitable or known heat source that can be fitted within the base 4840.

The micro-lever 4810 is referred to herein as "micro" because of its ability to be miniaturized for use in compact places and for the dissemination of distribution over a large surface area. It should however be understood that the general concept of the present invention may be used in other applications, regardless of the size of the lever formed according to the teaching of the present invention. Such applications are anticipated and covered by the present disclosure.

The micro-lever 4820 is generally similar in design and function to the micro-lever 4810, with the exception that the micro-lever 4820 has a unitary construction so that the apex of the bottom support 4822 (having a generally triangular cross-section) is fused within the upper platform 4821.

Figure 49:
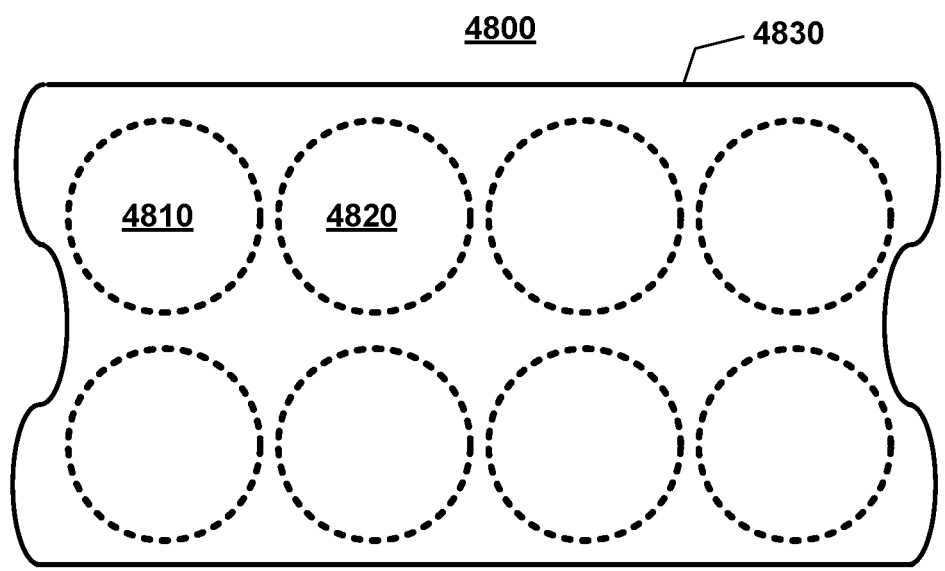
FIGS. 49, 50, 51 are top views of the sole (or fabric) of FIG. 48, showing the placements of various micro-levers (shown in dotted lines) within with sole, according to one embodiment of the present disclosure.
Figure 50:
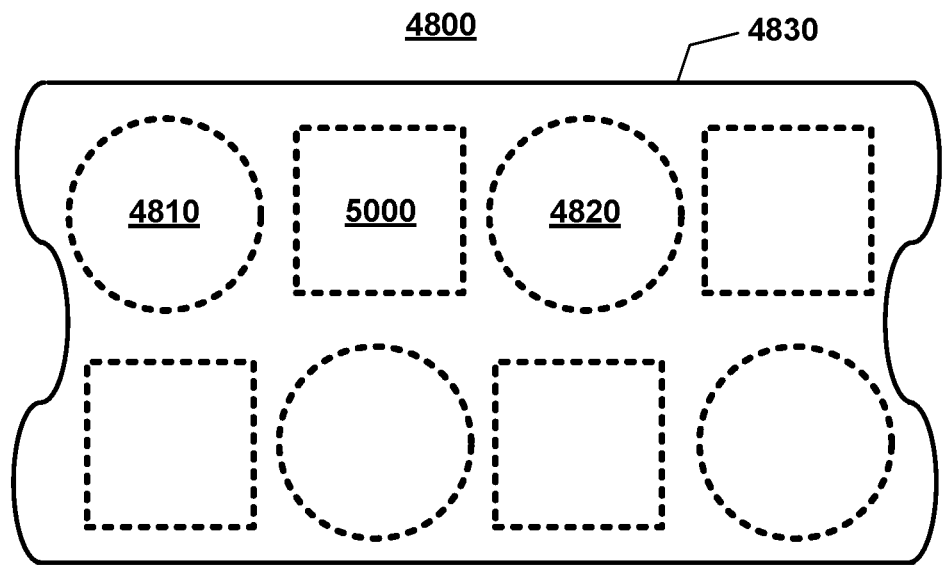
Figure 51:
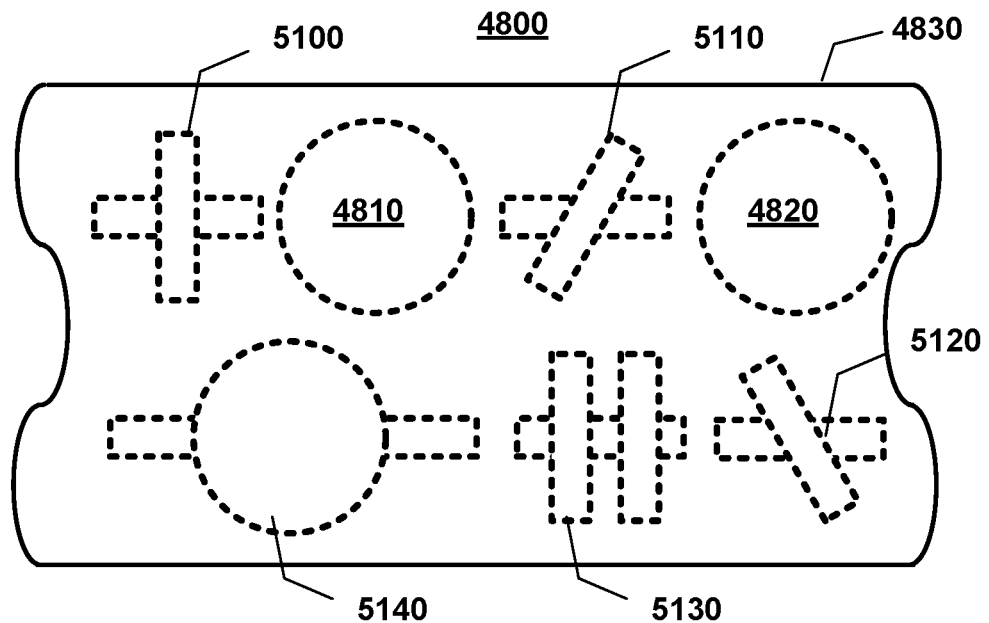

FIGS. 49, 50, 51 are top views of the sole (or fabric) 4800 of FIG. 48, showing the placements of various micro-levers 4810, 4820, 5000, 5100, 5110, 5120, 5130, 5140 (in dotted lines) within with the sole, according to one embodiment of the present disclosure. With reference to FIG. 49, the upper platforms 4811, 4821 of the micro-levers 4810, 4820 are shown to be circularly shaped. It should be understood that the shape of the upper platforms is not determinative or limiting to the general concept of the present invention, and that the embodiments shown in FIGS. 48 through 51 are for illustration purpose only.

FIG. 50 illustrates the rectangular (or square) shape of the upper platform of a micro-lever 5000. FIG. 51 illustrates other micro-levers 5100, 5110, 5120, 5130, 5140 having various shapes for the upper platform. For example, the upper platform of micro-lever 5100 is comprised of two superposed platforms that are disposed at right angle relative to each other. The upper platforms of micro-levers 5110, 5111 are generally similar to the upper platform of micro-lever 5100 with the exception that the superposed platforms form different angles relative to each other. The upper platform of micro-lever 5130 has three superposed platforms, while the upper platform of micro-lever has two superposed platforms of different shapes (circular and rectangular). The shapes and the superposition of the platforms depends on the desired redistribution of the reactive forces, in order to effect a predetermined result or application.

Figure 52:
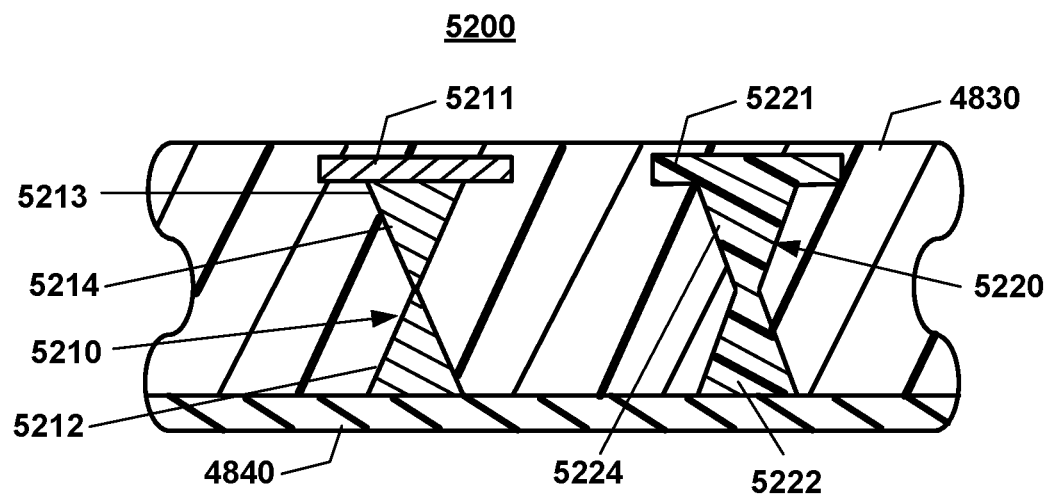
FIGS. 52, 53 are cross-sectional, fragmentary views of a shoe sole (or fabric) that incorporates micro-levers according to other embodiments of the present disclosure.
Figure 53:
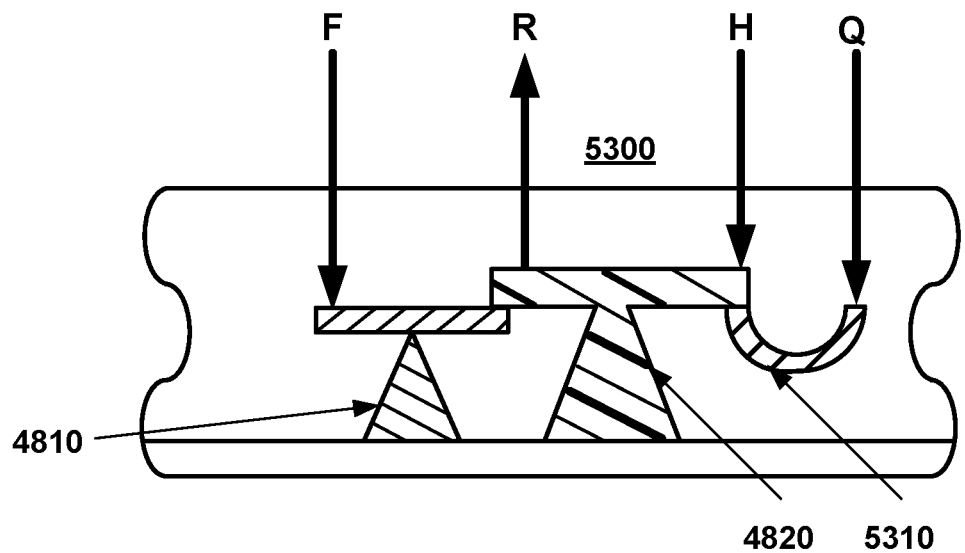
Figure 54:
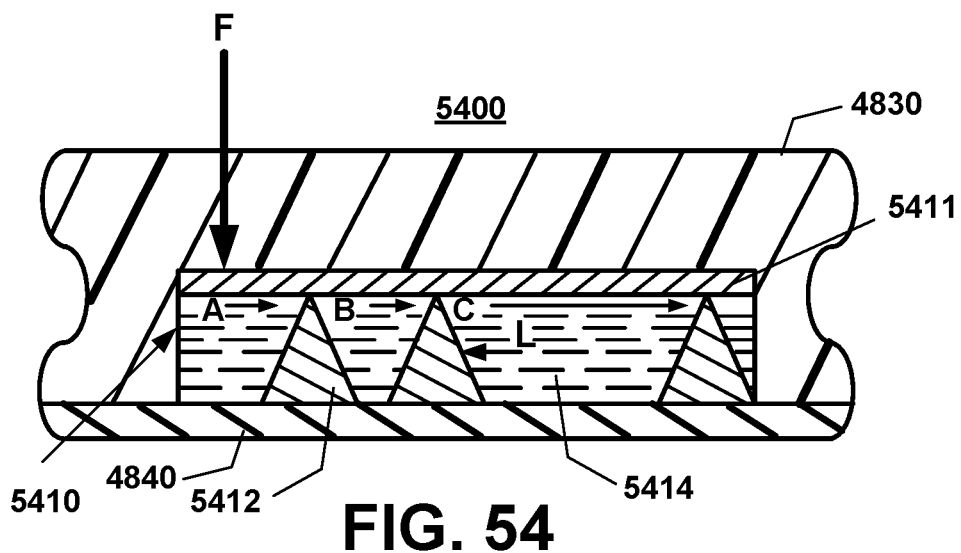
FIG. 54 is a cross-sectional, fragmentary view of a shoe sole (or fabric) that incorporates a dynamic micro-lever according to one embodiment of the present disclosure.

FIGS. 52, 53, 54 are cross-sectional, fragmentary views of a shoe sole (fabric, etc.) 5200, 5300, 5400 that incorporates micro-levers 5210, 5220, 4810, 4820, 5310, 5410, according to various embodiments of the present disclosure. Starting with FIG. 52, the micro-levers 5210, 5220 are generally similar in design and function to the micro-levers 4810, 4820 of FIG. 48, with some variations in the designs. More specifically, the micro-lever 5210 includes a bottom base 5212 that has its apex rotatably (or movably) connected to the apex of an inverted upper base 5214, which itself is secured to a platform 5211. The micro-lever 5220 is generally similar to the micro-lever 5210 with the exception that the micro-lever 5220 has its bottom base 5222 integrally formed with an inverter upper base 5224, which itself is secured to a platform 5221. In other terms, while the bottom and upper bases 5212, 5214 of the micro-lever 5210 form a minimal contact surface (i.e., point or line) at their apexes, the bottom and upper bases 5222, 5224 of the micro-lever 5220 form a larger contact surface than their respective apexes, while still be able to bend or ply under the effect of a force.

FIG. 53 illustrates a combination of exemplary micro-levers 4810, 4820, 5310 that work in conjunction with each other. The cross-hatching has been partially removed for clarity of illustration. In this particular embodiment, and although the representative micro-levers 4810, 4820 are illustrated, it should be clear that other micro-levers embodiments may be used, alternatively to, or in conjunction with the micro-levers 4810, 4820. The three (or more) micro-levers 4810, 4820 are so formed in close proximity to (or in contact with) each other, so that a force (e.g., F) applied to one micro-lever (e.g., 4810) may result in reactionary forces (e.g., R, H, Q) on at least some (or all) of the remaining micro-levers (e.g., 4820, 5310), resulting from the lever effect and the selective dispersal, absorption, redirection of forces.

The micro-lever 5310 is illustrated to have a generally semi-circular (or semi-cylindrical), though other embodiments or designs may be used instead. While one of the objectives of the micro-levers 4810, 4820 is to redirect (e.g., change of direction) the direction of the applied force (e.g., F to R, and R to H), one of the goals of the micro-lever 5310 is to translate the applied force and not necessarily to redirect its direction (e.g., H to Q). This design of the micro-levers may turn the encompassing sole or material 5300 into a programmable memory device (or programmable fabric), by regulating and controlling the transmission of the applied forces throughout the fabric or medium 5300.

FIG. 54 is a cross-sectional, fragmentary view of a medium 5400, such as a shoe sole, fabric, etc. that incorporates a dynamic micro-lever 5410 according to one embodiment of the present disclosure. The micro-lever 5410 is generally similar in function to the micro-levers described earlier, with the difference being that the micro-lever 5410 is dynamic.

To this end, the micro-lever 5410 includes a bottom base 5412 that is movable or slidable within a fluid medium 5414, and both the bottom base 5412 and the fluid medium 5414 are encapsulated within a chamber defined by a platform 5411 that is generally similar in function and design to the platform 4811 with the exception that the platform 5411 is longer (or wider) than the platform 4811, in order to allow a longer travel path to the bottom base 5412. In addition, while the bottom base 4812 is described as being secured to the platform 4811, the bottom base 5412 is not secured to the platform 5411, but is rather allowed to travel therealong, so as to change its lever action, that is to adjust the length of the lever arm between the force F and the apex of the bottom base 5412.

More specifically, when the force F is applied on one end of the platform 5411, it generates a force A that causes the bottom base 5412 to translate in the direction of the force A. However, the force A is countered with a resistance force L and is consequently reduced to force B and then to force C, until the bottom base reaches a rest point and stops its travel, allowing the lever action to affect the movement of the other (or opposite) end of the platform 5411, thus accomplishing dynamicity and self-adjustment.

Figure 55:
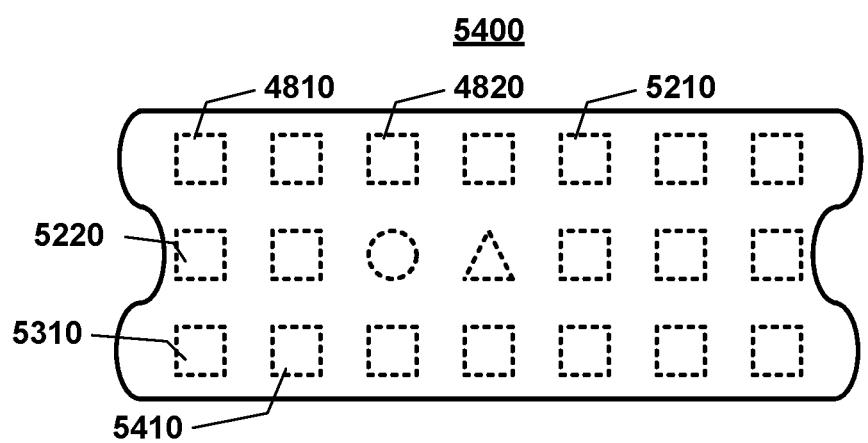
FIG. 55 is a top view of the medium of FIG. 54, showing the placements of various static and dynamic micro-levers (in dotted lines) within the medium, according to one embodiment of the present disclosure.

FIG. 55 is a top view of the medium 5400 of FIG. 54, showing the placements of various static and dynamic micro-levers (in dotted lines) within the medium 5400, according to one embodiment of the present disclosure.

While the present micro-levers are illustrated and described for use in various media, it should be clear that the present inventive concept may be used in numerous other applications, including but not limited to medical applications, such as sub-cutaneous implants, etc.

FIGS. 56, 57, 58, 59 illustrate shock absorbent mechanisms 5600, 5900 that can be incorporated or formed within the medium 5400 of FIG. 55, according to one embodiment of the present disclosure. Starting at FIG. 56, the mechanism 5600 generally includes a device or element that generates an electrical current (voltage or power), such as a piezoelectric element 5610. The mechanism 5600 further includes a solenoid 5620 that is electrically connected to the piezoelectric element 5610 by means of an electric cable (or a similar electrical connector, such as a metallic trace) 5630.

Although in this exemplary embodiment the piezoelectric element 5610 is shown mounted atop the solenoid 5620, it should be understood that alternative positions of the piezoelectric element 5610 relative to the solenoid 5620 are envisioned by the present disclosure.

Figure 56:
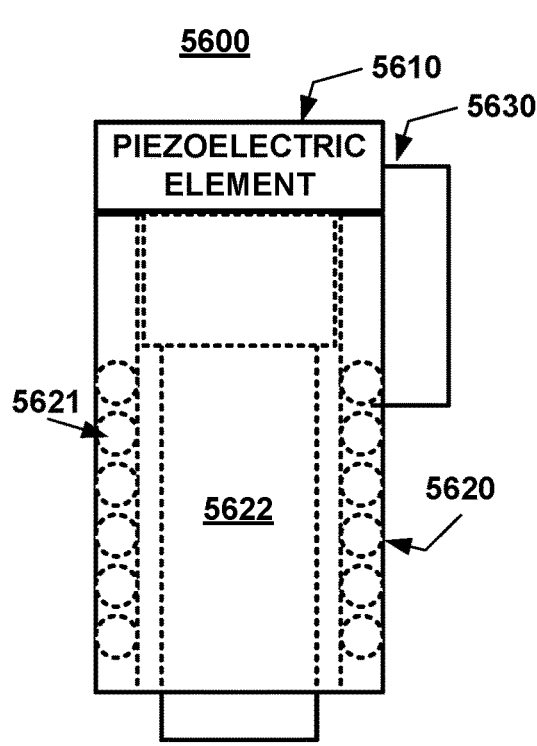
FIGS. 56, 57, 58, 59 illustrate various shock absorbent mechanisms that can be incorporated or formed within the sole of FIG. 55, according to one embodiment of the present disclosure.
Figure 57:
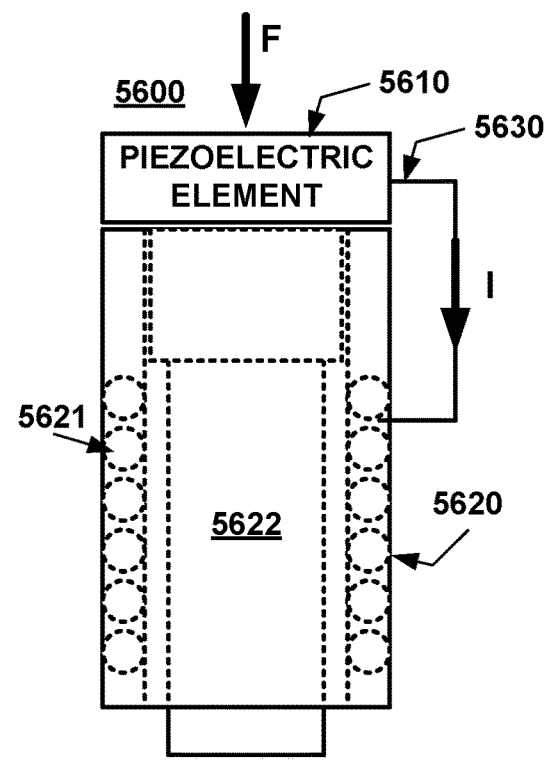

FIGS. 56, 57 illustrate the operation of the mechanism 5600 upon the application of a force F. As shown in FIG. 57, when a force F is applied to the piezoelectric element 5610, the latter generates a corresponding electrical current, I, that feeds the solenoid 5620. As further illustrated in FIG. 58, the solenoid 5620, which is generally formed of a coil 5621 and a plunger 5622, is activated by the applied current, I, to generate a reactive force, R. The reactive force, R, forces the plunger 5622 to move upward (or in the direction countering the applied force, F). In some applications, the current, I, is amplified by an amplifier to generate a sufficient reactive force, R, so that the plunger head 5625 is raised above its resting position.

Figure 58:
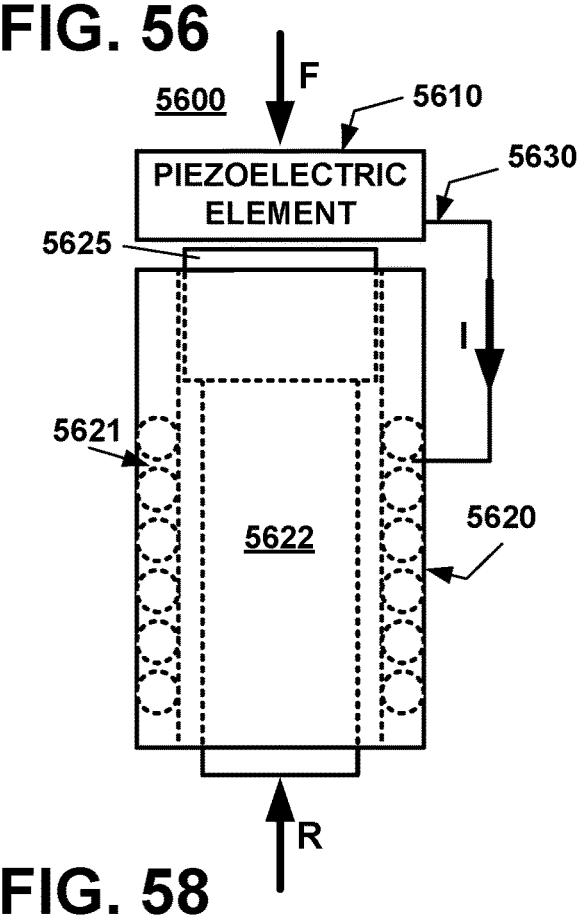
Figure 59:
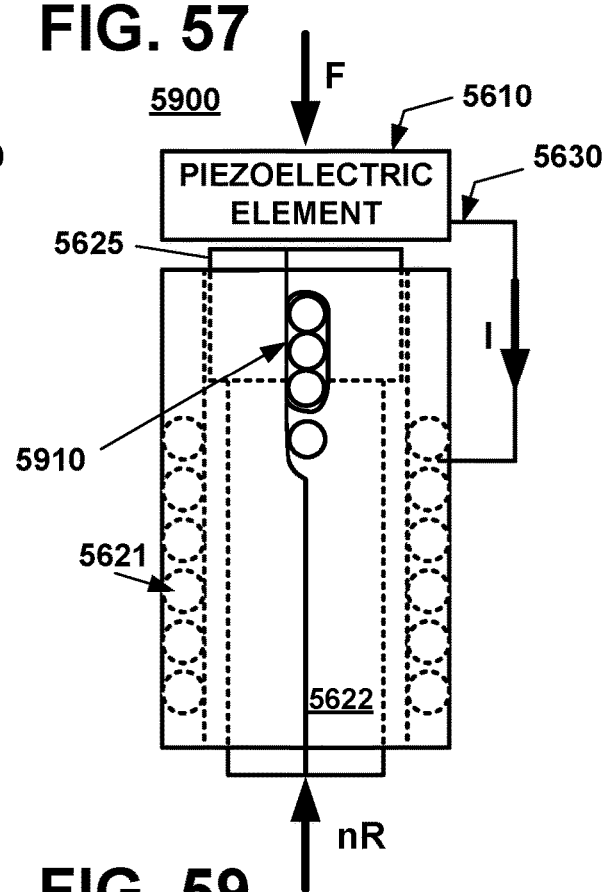

FIG. 59 illustrates an exemplary mechanical amplification device (or amplifier 5910. In one embodiment, the amplifier 5910 includes a lever mechanism that is similar in concept and design to the lever mechanisms 4310, 4320 of FIG. 43, as described in greater detail above, which description is incorporated herein by this reference. In this embodiment, if the piezoelectric element 5610 were to generate a force R (as is shown in FIGS. 56, 57, 58), the amplifier 5910 generates a force, nR, that is a multiple of the force, R, thus amplifying it. It should be noted that various control devices of the current, I, may be incorporated within the design of the embodiments of FIGS. 56 through 59, which control devices may be physically embedded within the medium 5400 alongside or proximity to the mechanism 5600, or alternatively, these control devices could be remotely incorporated within the posture adjustment mechanisms 4158, 4188 or the feedback device 4180 of FIG. 41.

FIGS. 60, 61, 62, 63, 64 illustrate alternative shock absorbent "pebbles" 6000 that can be incorporated or formed within medium 5400 of FIG. 55, according to one embodiment of the present disclosure. Starting with FIG. 60, the pebble 6000 is generally formed of a deformable (plastic or elastic) membrane 6010 that defines two chambers 6011 and 6012 that are connected with an air permeable (or compressible gas permeable) membrane 6015. The membrane 6015 is permeable to air (or gas) but not to water (liquid, fluid, or gel).

In a resting position, the first chamber 6011 is filled with a mixture of air (or gas) 6016 along with water (liquid, fluid, or gel) 6018. The second chamber 6012 is filled with the same (similar or dissimilar) gas 6019 as the gas 6016. Both chambers 6011, 6012 remain at equilibrium until an external force is applied to the first chamber 6011 (FIG. 61) or to the second chamber 6012 (FIG. 63). In one embodiment, the gel 6018 may be agrose gel.

With reference to FIG. 61, as the force F is applied to the first chamber 6011, the fluid 6018 contained therewithin may not be compressed, but the gas 6016 may be compressed. As a result, at least some of the gas molecules are forced into the second chamber 6012, inflating it until such time as the force F is balanced (or equalized) by the gas pressure in the second chamber 6012, at which time the flow of the gas molecules 6016 from the first chamber 6011 to the second chamber 6012 stops. In consequence, the force F is absorbed by the operation of the pebble 6000 as described. The pebbles 6000 may be micro-sized (as micro-capsules) for distribution over a large area, or sized according to the desired application. The pebbles 6000 may have various commercial applications as described herein, and further including but not limited to packaging of transported items or military arsenals.

FIGS. 62, 63 illustrate the pebble 6000 as described earlier in connection with FIGS. 60, 61. However, in this embodiment, the pebble 6000 is used in an inverted position, so that the force, F, is applied to the second chamber 6012. This application may be desirable in situations where the pebbles 6000 are disbursed or formed indiscriminately. The operation of the pebble 6000 of FIGS. 62, 63 is generally similar to that of the pebble 6000 of FIGS. 60, 61, with the variation that as the force F is applied to the second chamber 6012 and cause at least some of the molecules of the gas 6019 to traverse the intermediate membrane 6015 into the first chamber 6011, to counter or absorb the force F, as described earlier.

Figure 64:
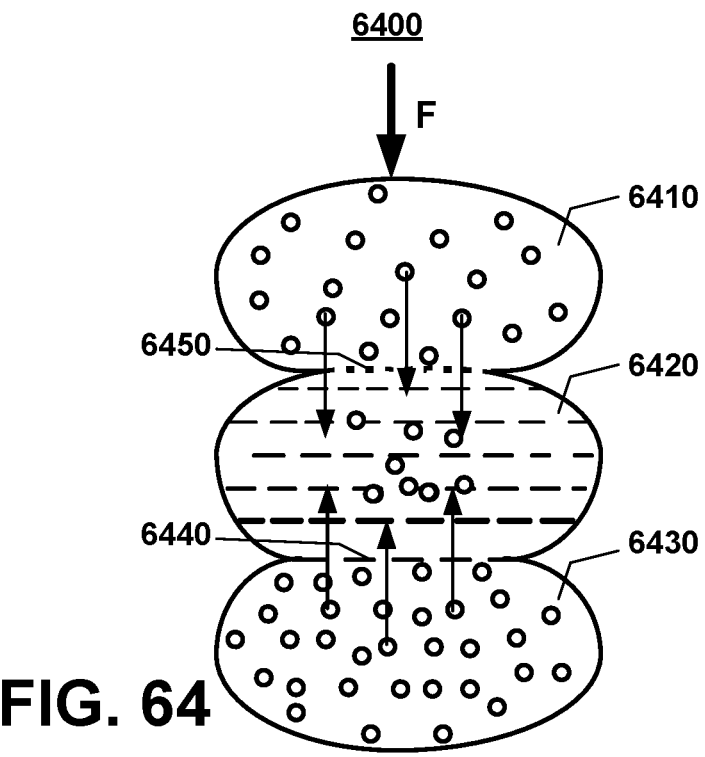
Figure 65:
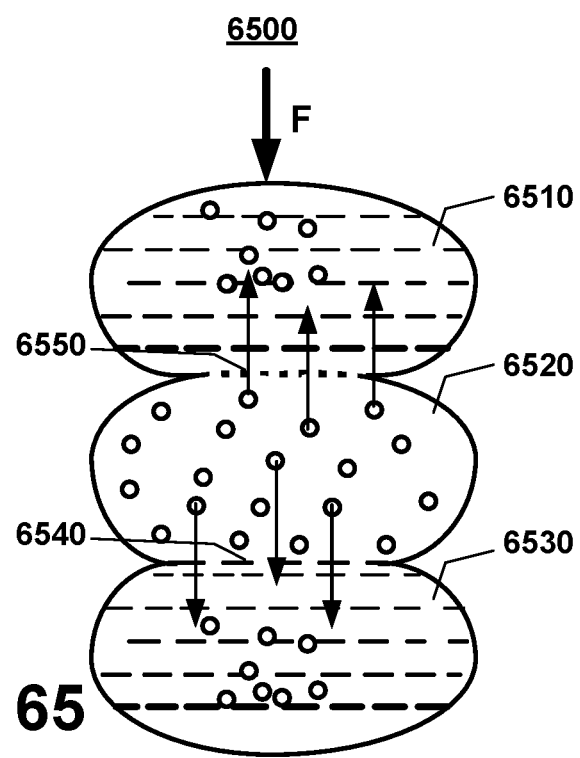

FIGS. 64, 65, illustrate two additional embodiments of the pebbles 6400, 6500, wherein the pebbles 6400, 6500 are formed of a membrane that defines more than just two chambers as described in connection with FIGS. 60 through 63. In the embodiment illustrated in FIG. 64, the pebble 6400 is formed of three chambers 6410, 6420, 6430. The upper chamber 6410 contains a gas, the intermediate chamber 6420 contains either a liquid or a combination of liquid/gas combination, and the bottom chamber 6430 contains gas. As a result, when force F is applied, the gas molecules in the upper chamber 6410 and the bottom chamber 6430 are precipitated, through the gas permeable membranes 6440, 6450 to the intermediate chamber 6420, as described earlier.

In the embodiment illustrated in FIG. 64, the pebble 6400 is formed of three chambers 6410, 6420, 6430. The upper chamber 6410 contains a gas, the intermediate chamber 6420 contains either a liquid or a combination of liquid and gas, and the bottom chamber 6430 contains gas. As a result, when force F is applied, the gas molecules in the upper chamber 6410 and the bottom chamber 6430 are precipitated, through the gas permeable membranes 6440, 6450 to the intermediate chamber 6420, as described earlier.

In the embodiment illustrated in FIG. 65, the pebble 6500 is formed of three chambers 6510, 6520, 6530. The upper chamber 6510 contains either a liquid or a combination of liquid and gas, the intermediate chamber 6520 contains a gas, and the bottom chamber 6530 contains either a liquid or a combination of liquid and gas. As a result, when force F is applied, the gas molecules in the intermediate chamber 6520 are precipitated, through the gas permeable membranes 6540, 6550 to the upper chamber 6510 and to the bottom chamber 6520, as described earlier.

It should be understood that various other combinations of chambers and gas or liquid contained therein, are contemplated by the present disclosure. In addition, while particular embodiments of the present invention have been disclosed, it is to be understood that various different modifications are possible and are contemplated within the scope of the specification, drawings, abstract and appended claims.

In each of the flow charts described herein, one or more of the methods may be embodied in a computer readable medium containing computer readable code such that a series of steps are performed when the computer readable code is executed on a computing device. In some implementations, certain steps of the methods are combined, performed simultaneously or in a different order, or perhaps omitted, without deviating from the spirit and scope of the invention. Thus, while the method steps are described and illustrated in a particular sequence, the use of a specific sequence of steps is not meant to imply any limitations on the invention. Changes may be made with regards to the sequence of steps without departing from the spirit or scope of the present invention. The use of a particular sequence is therefore, not to be taken in a limiting sense, and the scope of the present invention is defined only by the appended claims.

As it will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

As it will be further appreciated, the processes in embodiments of the present invention may be implemented using any combination of software, firmware or hardware. As a preparatory step to practicing the invention in software, the programming code (whether software or firmware) will typically be stored in one or more computer readable storage mediums for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The article of manufacture containing the programming code is used by either executing the code directly from the storage device, by copying the code from the storage device into another storage device such as a hard disk, RAM, etc., or by transmitting the code for remote execution using transmission type media such as digital and analog communication links. The methods of the invention may be practiced by combining one or more machine-readable storage devices containing the code according to the present invention with appropriate processing hardware to execute the code contained therein. An apparatus for practicing the invention could be one or more processing devices and storage systems containing or having network access to program(s) coded in accordance with the invention.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, R.F, etc., or any suitable combination of the foregoing. Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Thus, it is important that while illustrative embodiments of the present invention are described in the context of a fully functional computer (server) system with installed (or executed) software, those skilled in the art will appreciate that the software aspects of the illustrative embodiments of the present invention are capable of being distributed as a program product in a variety of forms, and that an illustrative embodiment of the present invention applies equally regardless of the particular type of media used to actually carry out the distribution.

In addition, while the present invention has been described with reference to exemplary embodiments, it will be understood by those skilled in the art that various changes may be made and equivalents may be substituted for elements thereof without departing from the scope of the invention. Furthermore, many modifications may be made to adapt a particular system, device or component thereof to the teachings of the invention without departing from the essential scope thereof. Therefore, it is intended that the invention not be limited to the particular embodiments disclosed for carrying out this invention, but that the invention will include all embodiments falling within the scope of the appended claims.

As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Moreover, the use of the terms first, second, etc. do not denote any order or importance, but rather the terms first, second, etc. are used to distinguish one element from another. In addition, listing terms such as "a", "b", c", "first", "second", and "third" are used herein and in the appended claims for purposes of description and are not intended to indicate or imply relative importance or significance.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A programmable medium for distributing at least part of a force or shock, F, applied onto the medium, the medium comprising:
   a programmable combination of levers that are selectively distributed within the medium to allow at least some of the levers to cooperate in order to selectively disperse, absorb, redirect, or translate at least part of the force or shock, F, in a customizable fashion;
   wherein the medium includes a pliable material that encapsulates at least part of said some of the levers;
   wherein said some of the levers are formed of a material that is stiffer than the pliable material of the medium, so that as the force or shock, F, is applied onto said some of the levers, said some of the levers enable a lever action or momentum by pivoting within the pliable material;
   wherein the pliable material is deformable, plastic, or elastic;
   wherein said some of the levers include at least a first lever and a second lever; and
   wherein the first lever and the second lever are disposed in close proximity relative to each other so that as at least part of the force or shock, F, is applied at least in part onto the first lever, the first lever pivots within the pliable material to engage the second lever, so as and to apply a reactionary force, R, to the second lever, effectively dispersing, absorbing, redirecting, or translating said at least part of the force or shock, F, within the medium, for regulating the distribution of said at least part of the force or shock, F, within the medium.

2. The programmable medium of claim 1, wherein the first lever includes a first platform that is pivotally secured to a first apex;
   wherein the second lever includes a second platform that is pivotally secured to a second apex;
   wherein as at least part of the force or shock, F, is applied at least in part on the first lever, the first platform pivots around the first apex and causes said at least part of the force or shock, F, to be reoriented by the first lever so that the first platform applies the reactionary force, R, to the second platform; and
   wherein the second lever reorients the reactionary force, R, into a force, H, effectively spatially distributing the force or shock, F, through the medium.

3. The programmable medium of claim 2, wherein said some of the levers further include a third lever that extends from the second platform and that further translates at least part of the force, H, through the medium.

4. The programmable medium of claim 3, wherein the third lever is semi-circularly shaped.

5. The programmable medium of claim 1, wherein the first lever pivots within the pliable material to push against the second lever and to apply the reactionary force, R, onto the second lever.

6. The programmable medium of claim 1, wherein the pliable material is made of a synthetic resin, and wherein the first lever and the second lever are made at least in part of hard plastic or rubber.

7. The programmable medium of claim 1, wherein the medium is part of any of: a shoe sole, a fabric, or packaging material.

8. The programmable medium of claim 1, wherein the programmable combination of levers includes a plurality of programmably interacting micro-levers that are distributed through the medium.

9. A programmable medium for distributing at least part of a force or shock, F, applied onto the medium, the medium comprising:
   a programmable combination of levers that are selectively distributed within the medium to allow at least some of the levers to cooperate in order to selectively disperse, absorb, redirect, or translate at least part of the force or shock, F, in a customizable fashion;
   wherein the medium includes a pliable material that encapsulates at least part of said some of the levers;
   wherein said some of the levers are formed of a material that is stiffer relative to the pliable material of the medium, so that as said at least part of the force or shock, F, is applied onto said some of the levers, said some of the levers enable a lever action or momentum by pivoting within the pliable material;
   wherein said at least some of the levers include at least a first lever and a second lever;
   wherein the first lever includes a first platform that is pivotally secured to a first apex; and wherein the first platform includes a first free end and a second free end that are disposed on opposite sides relative to the first apex, so that as said at least part of the force or shock, F, is applied onto the first free end of the first platform, the lever action or momentum causes the second free end of the first platform to pivot around the first apex and to apply a reactionary force or shock, R, to the second lever, effectively dispersing, absorbing, redirecting, or translating said at least part of the force or shock, F, within the medium, for regulating the distribution of said at least part of the force or shock, F, within the medium.

10. The programmable medium of claim 9, wherein the second lever includes a second platform that is pivotally secured to a second apex;

wherein the second platform includes a third free end and a fourth free end that are disposed on opposite sides relative to the second apex; and wherein the reactionary force or shock, R, is applied at least in part on the third free end of the second platform, causing the third free end and the fourth free end to pivot around the second apex.

11. The programmable medium of claim 10, wherein as said at least part of the reactionary force or shock, R, is applied onto the third free end of the second platform, the lever action or momentum generates a reoriented reactionary force or shock, H, onto the fourth free end of the second lever, effectively further dispersing, absorbing, redirecting, or translating said at least part of the force or shock, F, within the medium, for further regulating the distribution of said at least part of the force or shock, F, within the medium.

12. The programmable medium memory device of claim 9, wherein the programmable combination of levers includes a plurality of micro-levers that are distributed through the medium.

13. The programmable medium of claim 12, wherein the plurality of micro-levers include a dynamic micro-lever.

14. The programmable medium of claim 13, wherein the medium includes a fluid medium;

wherein the dynamic micro-lever includes a bottom base that is movable or slidable within the fluid medium; and wherein the bottom base and the fluid medium are encapsulated within a chamber defined by a movable platform.

15. The programmable medium of claim 14, wherein the bottom base is allowed to travel along the platform so as to change the lever action or momentum of the dynamic micro-lever by dynamically adjusting the length of a lever arm of the platform, between the force or shock, F, and the top portion of the bottom base.

16. The programmable medium of claim 12, further including a heat source that is connected to said at least one of the micro-levers.

17. The programmable medium of claim 12, further including a base that provides a common support to at least some of the plurality of micro-levers.

18. The programmable medium of claim 17, wherein the base is formed of rubber or hard plastic.

19. The programmable medium of claim 17, wherein said at least some of the plurality of micro-levers are affixed to the base.

20. The programmable medium of claim 17, wherein said at least some of the plurality of micro-levers are slidably supported by the base.

* * * * *